US009944951B2

(12) United States Patent
Ji et al.

(10) Patent No.: US 9,944,951 B2
(45) Date of Patent: *Apr. 17, 2018

(54) CHROMOSOME 3P21.3 GENES ARE TUMOR SUPPRESSORS

(75) Inventors: Lin Ji, Sugar Land, TX (US); John Dorrance Minna, Dallas, TX (US); Jack Roth, Houston, TX (US); Michael Lerman, Rockville, MD (US)

(73) Assignees: Board of Regents, The University of Texas System, Austin, TX (US); The United States of America as represented by the Secretary of the Department of Health and Human Services, Washington, DC (US)

( * ) Notice: Subject to any disclaimer, the term of this patent is extended or adjusted under 35 U.S.C. 154(b) by 301 days.

This patent is subject to a terminal disclaimer.

(21) Appl. No.: 13/114,921

(22) Filed: May 24, 2011

(65) Prior Publication Data

US 2012/0076851 A1    Mar. 29, 2012

Related U.S. Application Data

(60) Continuation of application No. 11/932,724, filed on Oct. 31, 2007, now Pat. No. 7,977,468, which is a continuation of application No. 10/445,718, filed on May 27, 2003, now Pat. No. 7,902,441, which is a division of application No. 09/902,003, filed on Jul. 10, 2001, now abandoned.

(60) Provisional application No. 60/217,112, filed on Jul. 10, 2000.

(51) Int. Cl.
*C12N 15/86* (2006.01)
*A61K 48/00* (2006.01)
*A01K 67/027* (2006.01)
*C07K 14/47* (2006.01)
*C12N 15/85* (2006.01)
*C12Q 1/68* (2018.01)

(52) U.S. Cl.
CPC .......... *C12N 15/86* (2013.01); *A01K 67/0271* (2013.01); *A01K 67/0275* (2013.01); *A61K 48/00* (2013.01); *C07K 14/4703* (2013.01); *C12N 15/8509* (2013.01); *C12Q 1/6886* (2013.01); *A01K 2217/05* (2013.01); *A01K 2217/075* (2013.01); *A01K 2217/20* (2013.01); *A01K 2227/105* (2013.01); *A01K 2267/0331* (2013.01); *C12N 2710/10343* (2013.01); *C12N 2830/006* (2013.01); *C12Q 2600/118* (2013.01); *C12Q 2600/136* (2013.01); *C12Q 2600/154* (2013.01); *Y10S 977/916* (2013.01)

(58) Field of Classification Search
None
See application file for complete search history.

(56) References Cited

U.S. PATENT DOCUMENTS 7,144,711 B2    12/2006  Cismowski et al. ............ 435/29
2011/0123484 A1    5/2011  Lerman et al.

FOREIGN PATENT DOCUMENTS

| CA | 2342470 | 9/2002 |
| WO | WO 1998/016655 | 4/1998 |
| WO | WO 2000/061626 | 10/2000 |
| WO | WO 2002/076454 | 10/2002 |

OTHER PUBLICATIONS

Lin et al. Regulation of tumor suppressor gene FUS1 expression by the untranslated regions of mRNA in human lung cancer cells. Biochem Biophys Res Commun. Jul. 1, 2011;410(2):235-41.*
"Adeno-X™ Tet-Off™ Gene Expression System," located at http://clontech.takara-bio.co.jp/archive/200004/pdf/200004_12.pdf, dated Apr. 2000.
Anderson et al., "A simple method for the rapid generation of recombinant adenovirus vectors," *Gene Therapy*, 7:1034-1038, 2000.
Bernues et al., "Analysis of 3p allelic losses in renal cell carcinomas: Comparison with cytogenetic results," *Cancer Genet Cytogenet*; 107:121-124, 1998.
Brand et al., "Targeted gene expression as a means of altering cell fates and generating dominant phenotypes," *Development*, 118:401-415, 1993.
Buchhagen et al., "Two regions of homozygosity on chromosome 3p in squamous cell carcinoma of the head and neck: comparison with cytogenetic analysis," *Head & Neck*, 18:529-537, 1996.
Burbee et al., "Epigenetic inactivation of RASSF1A in lung and breast cancers and malignant phenotype suppression," *J. Natl Cancer Inst.*, 93:691-699, 2001.
Clark et al., "Polycations and cationic lipids enhance adenovirus transduction and transgene expression in tumor cells," *Cancer Gene Ther.*, 6(5):437-446, 1999.
Daigo et al., "Molecular cloning of a candidate tumor suppressor gene, DLC1, from chromosome 3p21.3 [1]," *Canc. Research*, 59:1966-1972, 1999.
Daly et al., "A homozygous deletion on chromosome 3 in small cell lung cancer cell line correlates with a region of tumor suppressive activity", *Oncogene* 8:1721-1729, 1993.
Dammann et al., "Epigenetic inactivation of a RAS association domain family protein from the lung tumour suppressor locus 3p21.3," *Nat Genet*, 25:315-319, 2000.

(Continued)

Primary Examiner — Anne M. Gussow
(74) Attorney, Agent, or Firm — Parker Highlander PLLC

(57) ABSTRACT

Tumor suppressor genes play a major role in the pathogenesis of human lung cancer and other cancers. Cytogenetic and allelotyping studies of fresh tumor and tumor-derived cell lines showed that cytogenetic changes and allele loss on the short arm of chromosome 3 (3p) are most frequently involved in about 90% of small cell lung cancers and greater than 50% of non-small cell lung cancers. A group of recessive oncogenes, Fus1, 101F6, Gene 21 (NPRL2), Gene 26 (CACNA2D2), Luca 1 (HYAL1), Luca 2 (HYAL2), PL6, 123F2 (RaSSFI), SEM A3 and Beta* (BLU), as defined by homozygous deletions in lung cancers, have been located and isolated at 3p21.3.

4 Claims, 46 Drawing Sheets

(56) References Cited

OTHER PUBLICATIONS

Deng et al., "Synergistic tumor suppression by coexpression of FUS1 and p53 is associated with down-regulation of murine double minute-2 and activation of the apoptotic protease-activating factor 1-dependent apoptotic pathway in human non-small cell lung cancer cells," *Cancer Res.*, 67:709-717, 2007.
Dermer "Another anniversary for the war on cancer," Bio/Technol., 12:320, 1994.
Dow et al., "Lipid-DNA complexes induce potent activation of innate immune responses and antitumor activity when administered intravenously," *J. Immunol.*, 163(3):1552-1561, 1999.
Duh et al., "A novel gene (Blu) that resides in the lung cancer region on chromosome 3p21.3 has the MYND Zn finger-like module-Human Blu protein (Blu) mRNA, completed cds," Abstract, Database EMBL Sequence Library, Database Accession No. U70824, XP002207890, 1998.
Duh et al., "A novel gene (Blu) that resides in the lung cancer region on chromosome 3p21.3 has the MYND Zn finger-like module-Human Blu protein testis isoform (Blu) mRNA, complete cds," Abstract, Database EMBL Sequence Library, Database Accession No. U70880, XP002207891, 1998.
European Search Report issued in European Application No. 01 952 604.5, dated Nov. 26, 2008.
Forgacs et al., "Mutation analysis of the PTEN/MMAC1 gene in lung cancer," *Oncogene*, 17:1557-1565, 1998.
Gazdar et al., "Characterization of paired tumor and non-tumor cell lines established from patients with breast cancer," *Internatl J Cancer*, 78:766-774, 1998.
Gazdar et al., "Molecular genetic changes found in human lung cancer and its precursor lesions," *Cold Spring Harbor Sym Quant Biol*, 59:565-572, 1994.
Gorunova et al., "Cytogenetic analysis of pancreatic carcinomas: Intratumor heterogeneity and nonrandom pattern of chromosome aberrations," *Genes Chrom Cancer*, 23:81-99, 1998.
Gromeier et al., "Viruses for the treatment of malignant glioma," *Curr. Opin. Mol. Ther.*, 3:503-508, 2001.
Gura, "Sytems for identifying new drugs are often faulty," *Science*, 278:1041-1042, 1997.
Hibi et al., "Three distinct regions involved in 3p deletion in human lung cancer," *Oncogene*, 7:445-449, 1992.
Hsieh et al., "Differential effects on growth, cell cycle arrest, and induction of apoptosis by resveratrol in human prostate cancer cell lines," *Exp. Cell Res.*, 249:109-115, 1999.
Hughson et al., "Clear-cell and papillary carcinoma of the kidney: An analysis of chromosome 3, 7, and 17 abnormalities by microsatellite amplification, cytogenetics, and fluorescence in situ hybridization," *Cancer Genet Cytogenet*, 106:93-104, 1998.
Hung et al., "Allele-specific chromosome 3p deletions occur at an early stage in the pathogenesis of lung carcinoma," *JAMA*, 273:558-563, 1995, Correction: *JAMA*, 273:1908, 1995.
Janmaat et al., "Response to epidermal growth factor receptor inhibitors in non-small cell lung cancer cells: limited antiproliferative effects and absence of apoptosis associated with persistent activity of extracellular signal-regulated kinase or Akt kinase pathways," *Clin. Cancer Res.*, 9:2316-2326, 2003.
Ji et al., "3p21.3 tumor suppressor cluster: prospects for translational applications," *Future Oncol.*, 1:79-92, 2005.
Kersemaekers et al., "Allelic loss and prognosis in carcinoma of the uterine cervix," *Internatl J Cancer*, 79:411-417, 1998.
Killary and Fournier, "Microcell fusion," *Methods in Enzymology*, 254:133-152, 1995.
Killary et al., "Definition of a tumor suppressor locus within a human chromosome 3p21-p22," *Proc. Natl. Acad. Sci.*, 89:10877-10881, 1992.
Kohno et al., "p53 mutation and allelic loss of chromosome 3p, 9p of preneoplastic lesions in patients with nonsmall cell lung carcinoma," *Cancer*, 85:341-347, 1999.

Kok et al., "A homozygous deletion in a small cell lung cancer cell line involving a 3p21 region with a marked instability in yeast artificial chromosomes", *Cancer Res.*, 54:4183-4187, 1994.
Kok et al., "Deletion of a DNA sequence at the chromosomal region 3p21 in all major types of lung cancer," *Nature*, 330:578-581, 1987.
Kok et al., "Deletions of the short arm of chromosome 3 in solid tumors and the search for suppressor genes," *Adv Cancer Res*, 71:27-92, 1997.
Kondo et al., "Overexpression of candidate tumor suppressor gene FUS1 isolated from the 3p21.3 homozyogous deletion region leads to G1 arrest and growth inhibition of lung cancer cells," *Oncogene*, 20:6258-6262, 2001.
Latif et al., "FUS1, a highly conserved gene, is located in the smalletst lung cancer region on 3p21.3—*Homo sapiens* lung cancer candidate FUS1 (FUS1) mRNA, complete cds," GenBank Accession No. AF055479, 1998.
Lerman and Minna, "The 630-kb lung cancer homozygous deletion region on human chromosome 3p21.3: identification and evaluation of the resident candidate tumor suppressor genes," *Cancer Res*, 60:6116-6133, 2000.
Lin et al., "Expression of several genes in the human chromosome 3p21.3 homozygous deletion region by an adenovirus vector results in tumor suppressor activities in vitro and in vivo," *Cancer Research*, 62:2715-2720, 2002.
Lu et al., "Systemic therapy with tumor suppressor FUS1-nanoparticles for stage IV lung cancer," 2007 AACR Annual Meeting, Apr. 14-18, 2007 (Abstract No. LB-348).
Minna et al., "Cancer of the Lung: Section 1: Molecular Biology of Lung Cancer," In: DeVita Jr., et al., (editors.) *Cancer: Principles and Practice of Oncology*. 5 ed. Philadelphia: Lippincott-Raven Publishers, 849-857, 1997.
Mizuguchi and Kay, "Efficient construction of a recombinant adenovirus vector by an improved in vitro ligation method," *Hum. Gene Therap.*, 9:2577-2583, 1998.
Naylor et al., "Loss of heterozygosity of chromosome 3p markers in small-cell lung cancer," *Nature*, 329:451-454, 1987.
Neubauer et al., "Cure of Helicobacter pylori infection and duration of remission of low-grade gastric mucosa-associated lymphoid tissue lymphoma," *J. Natl. Cancer Inst.*, 89:1350-1355, 1997.
Office Action issued in Australian Application No. 200127337, dated Apr. 6, 2005.
Office Action issued in Australian Application No. 200127337, dated Jan. 27, 2006.
Office Action issued in Australian Application No. 2006222760, dated Nov. 24, 2008.
Office Action issued in Australian Application No. 2006222760, dated Jun. 25, 2010.
Office Action issued in Canadian Application No. 2,415,422, dated Apr. 22, 2009.
Office Action issued in Canadian Application No. 2,415,422, dated Jan. 31, 2011.
Office Action issued in European Application No. 01 952 604.5, dated Sep. 23, 2011.
Office Action issued in Japanese Application No. 2002-509374, dated Jan. 6, 2011.
Office Action issued in Japanese Application No. 2002-509374, dated May 20, 2011.
Office Action issued in U.S. Appl. No. 09/902,003, dated Sep. 30, 2002.
Office Action issued in U.S. Appl. No. 09/902,003, dated Feb. 24, 2003.
Office Action issued in U.S. Appl. No. 10/445,718, dated Jan. 9, 2006.
Office Action issued in U.S. Appl. No. 10/445,718, dated May 30, 2006.
Office Action issued in U.S. Appl. No. 10/445,718, dated Apr. 4, 2007.
Office Action issued in U.S. Appl. No. 10/445,718, dated Oct. 9, 2007.
Office Action issued in U.S. Appl. No. 10/445,718, dated Jun. 16, 2008.
Office Action issued in U.S. Appl. No. 11/932,724, dated Nov. 19, 2009.

(56) References Cited

OTHER PUBLICATIONS

Office Action issued in U.S. Appl. No. 11/932,724, dated Aug. 3, 2010.
Pakula and Sauer, "Genetic analysis of protein stability and function," *Annu. Rev. Genet.*, 23:289-310, 1989.
PCT International Preliminary Examination Report issued in International Application No. PCT/US2001/021781, dated Apr. 2, 2003.
PCT International Search Report issued in International Application No. PCT/US2001/021781, dated Nov. 18, 2002.
Petersen et al., "Small-cell lung cancer is characterized by a high incidence of deletions on chromosomes 3p, 4q, 5q, 13q, and 17p," *Brit. J. Cancer* 75:79-86, 1997.
Richards, "Protein stability: still an unsolved problem," *Cell Mol. Life Sci.*, 53:790-802, 1997.
Roche et al., "Distinct 3p21.3 deletions in lung cancer and identification of a new human semaphorin," *Oncogene*, 12:1289-1297, 1996.
Sanchez et al., "A tumor suppressor locus within 3p14-p12 mediates rapid cell death of renal cell carcinoma in vivo," *Proc Natl Acad Sci,U.S.A*, 91:3383-3387, 1994.
Satoh et al., "Suppression of tumorigenicity of A549 lung adenocarcinoma cells by human chromosomes 3 and 11 introduced via microcell-mediated chromosome transfer," *Mol Carcinogenesis*, 7:157-164, 1993.
Sekido et al., "Cloning of a breast cancer homozygous deletion junction narrows the region of search for a 3p21.3 tumor suppressor gene," *Oncogene* 16:3151-3157, 1998.
Sekido et al., "Human semaphorins A(V) and IV reside in the 3p21.3 small cell lung cancer deletion region and demonstrate distinct expression patterns," *Proc Natl Acad Sci, U.S.A*, 93:4120-4125, 1996.
Sekido et al., "Progress in understanding the molecular pathogenesis of human lung cancer," *Biochimica Biophysica Acta*, 1378:F21-F59, 1998.
Shafer et al., "Non-small and small cell lung carcinoma cell lines exhibit cell type-specific sensitivity to edelfosine-induced cell death and different cell line-specific responses to edelfosine treatment," *Int. J. Oncol.*, 23(2):389-400, 2003.
Shay, "Telomerase in cancer: diagnostic, prognostic, and therapeutic implications," *Cancer J Sci American*, 4 Suppl 1:S26-S34, 1998.
Shay, "Telomerase in human development and cancer," *J Cell Physiol*, 173:266-270, 1997.
Todd et al., "An 80 Kb P1 from chromosome 3p21.3 suppresses tumor growth in vivo," *Oncogene*, 13:2387-2396, 1996.
Tomizawa et al., "Inhibition of lung cancer cell growth and induction of apoptosis after reexpression of 3p21.3 candidate tumor suppressor gene DEMA3B," *Proc. Natl. Acad.*, 98:13954-13959, 2001.
Trueheart et al., "Two Genes Required for Cell Fusion during Yeast Conjugation: Evidence for a Pheromone-Induced Surface Protein," *Molecular and Cellular Biology*, 7(7): 2316-2328, 1987.
Uzawa et al., "Functional evidence for involvement of multiple putative tumor suppressor genes on the short arm of chromosome 3 in human oral squamous cell carcinogenesis," *Cancer Genet Cytogenet* 107:125-131, 1998.
van den Berg et al., "Analysis of multiple renal cell adenomas and carcinomas suggests allelic loss at 3p21 to be a prerequisite for malignant development," *Genes Chrom Cancer*, 19:228-232, 1997.
Wagener, "Molecular Oncology: prospects for cancer diagnosis and therapy," published online at http://www.roche.com/pages/downloads/company/pdf/rtpenzberg01e.pdf.
Wei et al., "Construction of a 600-kilobase cosmid clone contig and generation of a transcriptional map surrounding the lung cancer tumor suppressor gene (TSG) locus on human chromosome 3p21.3: progress toward the isolation of a lung cancer TSG", *Cancer Res.* 56:1487-1492, 1996.

Whang-Peng et al., "A nonrandom chromosomal abnormality, del 3p(14-23), in human small cell lung cancer (SCLC)," *Cancer Genet Cytogenet*, 6:119-134, 1982.
Wistuba et al., "Allelic losses at chromosome 8p21-23 are early and frequent events in the pathogenesis of lung cancer," *Cancer Res*, 59:1973-1979, 1999.
Wistuba et al., "Deletions of chromosome 3p are frequent and early events in the pathogenesis of uterine cervical carcinoma," *Cancer Res*, 57:3154-3158, 1997.
Wistuba et al., "High resolution chromosome 3p allelotyping of human lung cancer and preneoplastic/preinvasive bronchial epithelium reveals multiple, discontinuous sites of 3p allele loss and three regions of frequent breakpoints," *Cancer Res*, 60:1949-1960, 2000.
Wistuba et al., "Molecular damage in the bronchial epithelium of current and former smokers," *J Natl Cancer Inst*, 89:1366-1373, 1997.
Wistuba et al., "Sequential molecular abnormalities are involved in the multistage development of squamous cell lung carcinoma," *Oncogene* 18:643-650, 1999.
Wu et al., "Benzo[a]pyrene diol epoxide-induced 3p21.3 aberrations and genetic predisposition to lung cancer," *Cancer Res*, 58:1605-1608, 1998.
Xie WK et al., "Immunization of Mice with Plasmid DNA against malaria and regulation of antigen expression by tetracycline-controlled promoter," *Sheng Wu Gong Cheng Xue Bao*, 16(1): 13-16, 2000. (Article in Chinese; Only English Abstract provided).
Zbar et al., "Loss of alleles of loci on the short arm of chromosome 3 in renal cell carcinoma," *Nature*, 327:721-724, 1987.
da Costa Prando et al., "Evidence of epigenetic regulation of the tumor suppressor gene cluster flanking RASSF1 in breast cancer cell lines," *Epigenetics*, 6(12):1413-1424, 2011.
Edfeldt et al., "Different gene expression profiles in metastasizing midgut carcinoid tumors," *Endocrine-Related Cancer*, 18:479-489, 2011.
Ivanova et al., "Autoimmunity, spontaneous tumourigenesis, and IL-15 insufficiency in mice with a targeted disruption of the tumour suppressor gene Fus1," *J. Pathol.*, 211(5):591-601, 2007. Abstract only.
Ivanova et al., "Mechanisms of FUS1/TUSC2 deficiency in mesothelioma and its tumorigenic transcriptional effects," *Molecular Cancer*, 8:91, 2009.
Li et al., "Frequent absence of tumor suppressor FUS1 protein expression in human bone and soft tissue sarcomas," *Anticancer Research*, 31(1):11-21, 2011. Abstract only.
Dai et al., "Genome-wide transcriptional profiling analysis of all trans retinoic acid-treated tongue carcinoma SCC-9 cells," *J. Surg. Oncol.*, Abstract only, 104(7):830-835, 2011.
Hu et al., "Effect of recombinant plasmid pEGFP-N1-NPRL2 on the biological characteristics of human gastric cancer cells," *Xi Bao Yu Fen Zi Mian Yi Yue Za Zhi*, Article in Chinese, English Abstract only, 28(10):1020-1024, 2012.
Kurata et al., "TUSC4/NPRL2, a novel PDK1-interacting protein, inhibits PDK1 tyrosine phosphorylation and its downstream signaling," *Cancer Sci.*, 99(9):1827-1834, 2008.
Li et al., "Functional characterization of the candidate tumor suppressor gene NPRL2/G21 located in 3p21.3c," *Cancer Res.*, 64(18):6438-6443, 2004.
Office Action issued in U.S. Appl. No. 13/346,528, dated Apr. 19, 2013.
Office Action issued in U.S. Appl. No. 13/346,528, dated May 18, 2012.
Office Action issued in U.S. Appl. No. 13/346,528, dated Sep. 28, 2012.
Otani et al., "The tumor suppressor NPRL2 in hepatocellular carcinoma plays an important role in progression and can be served as an independent prognostic factor," *J. Surg. Oncol.*, Abstract only, 100(5):358-363, 2009.

\* cited by examiner

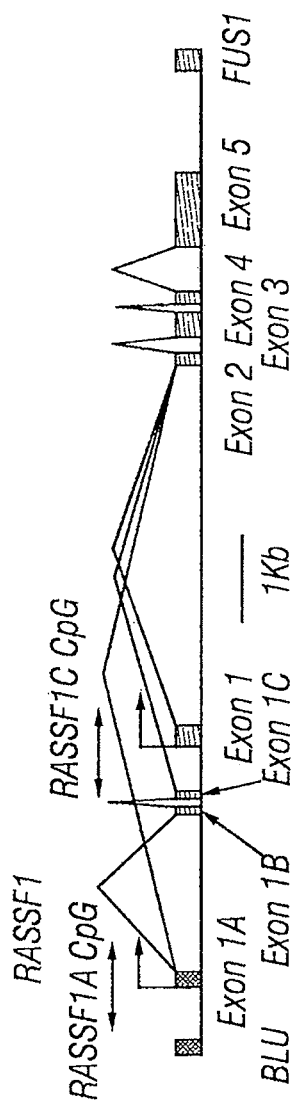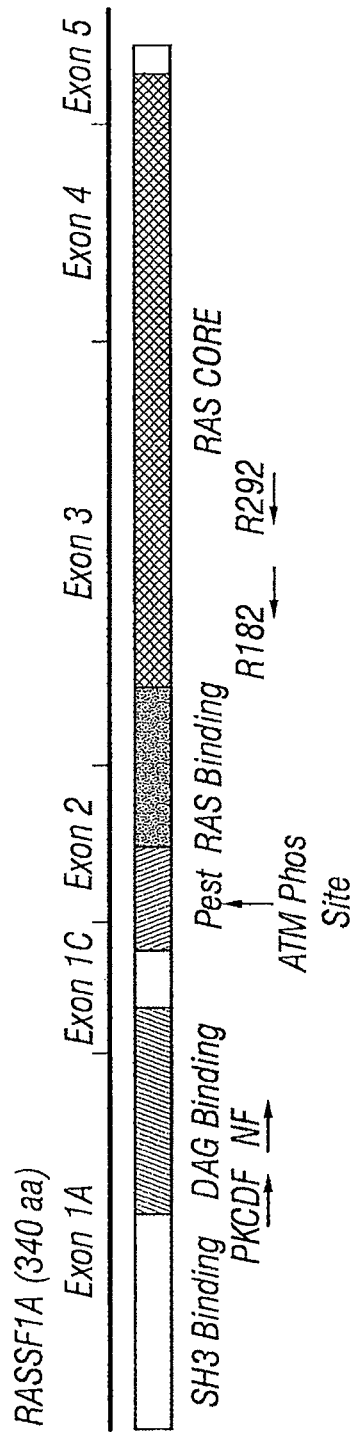
FIG. 12A
FIG. 12B

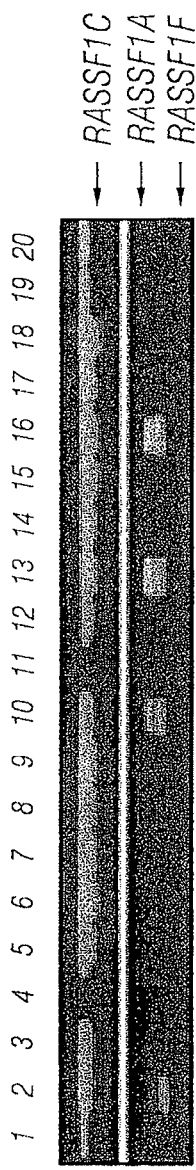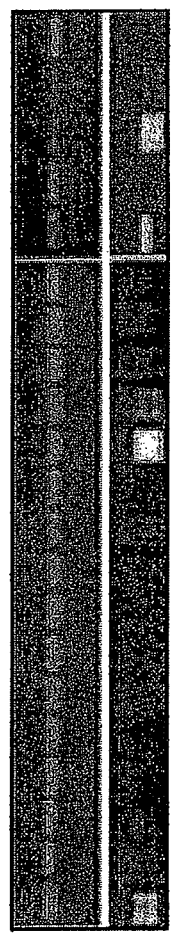
FIG. 13A
FIG. 13B
FIG. 13C

CHROMOSOME 3P21.3 GENES ARE TUMOR SUPPRESSORS

This is a continuation of co-pending application U.S. Ser. No. 11/932,724, filed Oct. 31, 2007, now U.S. Pat. No. 7,977,468 which is a continuation of application U.S. Ser. No. 10/445,718, filed May 27, 2003, now U.S. Pat. No. 7,902,441 which is a divisional of U.S. Ser. No. 09/902,003 filed Jul. 10, 2001, now abandoned, which claims the benefit of U.S. Provisional Application No. 60/217,112, filed Jul. 10, 2000.

This invention was made with government support under Grant No. P50-CA70907 awarded by National Institutes of Health. The government has certain rights in the invention.

BACKGROUND OF THE INVENTION

I. Field of the Invention

The invention generally relates to the fields of molecular biology and oncology.

II. Related Art

Cancer is the result in the occurrence of multiple factors. Mutations may occur in proto-oncogenes that cause cellular proliferation to increase. Mutations also may occur in tumor suppressors whose normal function is to regulate cellular proliferation. Mutations in DNA repair enzymes impair the ability of the cell to repair damage before proliferating. Tumor suppressor genes are normal genes whose absence (loss or inactivation) can lead to cancer. Tumor suppressor genes encode proteins that slow cell growth and division. Cancer arises when there is a mutation in both alleles.

Tumor suppressor genes (TSGs) play a major role in the pathogenesis of human lung cancer and other cancers. Lung cancer cells harbor mutations and deletions in multiple known dominant and recessive oncogenes[6,7]. Known TSGs such as Rb, p53, and putative TSGs have been found at chromosome regions 3p, 5q, 6p, 8p, 9p, and 11p as well as other sites[6-8,10]. Cytogenetic and allelotyping studies of fresh lung tumors and tumor cells showed tumor-cell allele loss at multiple sites, suggesting the existence of one or more such TSGs[6-8,10]. However, cytogenetic changes and allele loss on the short arm of chromosome 3 (3p) have been shown to be most frequently involved in about 90% of small cell lung cancers (SCLCs) and >50% of non-small cell lung cancers (NSCLCs)[6,8,10,11]. SCLC and NSCLC are the two treatment groups of lung tumors and are made up of four histological types. Squamous cell-, adeno-, and large cell carcinomas are in the NSCLC group. Small cell lung cancer is in the SCLC group. Approximately 75% of lung tumors are NSCLCs. Metastases occur later with NSCLC than with SCLC. SCLC is one of the most metastatic of solid tumors[52]. In addition, similar 3p changes have been seen in several other cancers in addition to lung, such as renal[12,13], breast[14,15], head and neck[16], pancreatic[17], kidney[18], oral[19], and uterine cervical cancers[20,21]. Furthermore, a group of TSGs, as defined by homozygous deletions in lung cancers, have been located and isolated at 3p21.3 in a 450-kb region[6,10,22-24]. Studies of lung cancer preneoplasia indicate that 3p21 allele loss is the earliest genetic abnormality in lung cancer detected so far, occurring in hyperplastic lesions; this shows that one or more 3p-recessive oncogenes function as "gatekeepers" in the molecular pathogenesis of many human cancers, including lung cancer, where it is likely to be involved in >50% of all cases[6,10,22-26].

Recently, human chromosome band 3p21.3 has been shown to undergo overlapping homozygous deletions in several SCLC and NSCLC lines; candidates of TSGs have been located in this critical region in several human cancers, further defining a TSG region[6,10,24,27]. The evidence shows that genes in this 3p21 critical region are involved in regulation of the telomerase-mediated cellular immortality pathway in lung, renal, and breast cancer cells[28,29]. It has also been shown that 3p deletion occurs more frequently in the lung tumor tissues of patients who smoke. In addition, elevated sensitivity to the carcinogen benzo[a]pyrene diol epoxide at 3p21.3 has been associated with an increased risk of lung cancer, suggesting that 3p21.3 is a molecular target of carcinogens in lung cancer[31]. Despite those studies, there remains a need to further identify the functions of these genes and demonstrate their involvement with cancer.

SUMMARY OF THE INVENTION

The tumor suppressor genes at 3p21.3 are now disclosed: Gene 26 (CACNA2D2)[3,40], PL6, Beta* (BLU), LUCA-1 (HYAL1), LUCA-2 (HYAL2), 123F2 (RASSF1), Fus1, 101F6, Gene 21 (NPRL2), and SEM A3. The function of the individual 3p genes in suppression of tumor growth and tumor progression, induction of apoptosis, alteration of cell cycle kinetics, and repression of telomerase activity has been characterized by the liposome- and recombinant adenoviral vector-mediated transfer of 3p genes in vitro and in vivo. This also is the initial disclosure of the Beta* gene.

Therefore, it is an objective of the present invention to provide methods of using tumor suppressors having a chromosomal location of 3p21.3. It is also an objective to provide a tumor suppressor, Beta*. Further, it is an objective to provide methods of constructing recombinant adenovirus in which these tumor suppressors may be inserted.

An embodiment of the present invention is an isolated polynucleotide encoding a polypeptide comprising an amino acid sequence of SEQ ID NO:2. There is also provided a nucleic acid with the sequence of SEQ ID NO:1. Further provided is an isolated polypeptide comprising the amino acid sequence of SEQ ID NO:2. Another embodiment is a nucleic acid of 15 to about 100 base pairs comprising from 15 contiguous base pairs of SEQ ID NO:1, or the complement thereof. A further embodiment includes from about 20, 25, 30, 40, 50 or 100 contiguous base pairs of SEQ ID NO:1, or the complement thereof.

Another embodiment of the invention is an isolated peptide having between 10 and about 50 consecutive residues of SEQ ID NO:2. Further, the peptide may comprise 15, 20, 25, or 30 consecutive residues of SEQ ID NO:2. In this application, "about" is defined as within + or −2 amino acids.

Yet another embodiment is an expression cassette comprising a polynucleotide encoding a polypeptide having the sequence of SEQ ID NO:2, wherein said polynucleotide is under the control of a promoter operable in eukaryotic cells. In another embodiment, the promoter of this expression cassette is heterologous to the coding sequence. The promoter may be a tissue specific and inducible promoter. In another embodiment, the expression cassette may be contained in a viral vector. The viral vector may be a retroviral vector, an adenoviral vector, and adeno-associated viral vector, a vaccinia viral vector, or a herpesviral vector. In a further embodiment the expression cassette may comprise a polyadenylation signal.

Another embodiment is a cell comprising an expression cassette comprising a polynucleotide encoding a polypeptide having the sequence of SEQ ID NO:2, wherein said polynucleotide is under the control of a promoter operable in eukaryotic cells, said promoter being heterologous to said polynucleotide.

Yet another embodiment of the invention is a monoclonal antibody that binds immunologically to a polypeptide comprising SEQ ID NO:2, or an immunologic fragment thereof. Also provided is a monoclonal antibody with a detectable label. The label may be a fluorescent label, a chemiluminescent label, a radiolabel and an enzyme. Another embodiment of the invention is a hybridoma cell that produces a monoclonal antibody that binds immunologically to a polypeptide comprising SEQ ID NO:2, or an immunologic fragment thereof. A further embodiment is a polyclonal antisera, antibodies of which bind immunologically to a polypeptide comprising SEQ ID NO:2, or an immunologic fragment thereof.

Yet another embodiment is a isolated and purified nucleic acid that hybridizes, under high stringency conditions, to a DNA segment comprising SEQ ID NO:1, or the complement thereof. In a further embodiment the nucleic acid is about 15, 17, 20 or 25 bases in length.

Another embodiment of the invention is a method for constructing a recombinant adenovirus comprising: (a) providing a shuttle vector, said shuttle vector comprising an adenoviral inverted terminal repeat (ITR) sequence, an expression cassette comprising a promoter and a poly-A sequence, a transgene under the control of said promoter, and unique restriction sites at the 5'- and 3'-ends of the ITR-promoter-transgene-poly-A segment; (b) cutting at said restriction enzyme sites; (c) ligating the released segment into an adenoviral vector lacking the entire E1 and E3 regions and transforming the resulting vector a bacterial host cell; (d) obtaining vector from said bacterial host cell and digesting the vector to release the E1/E3-deleted adenovirus genome; and (e) transfecting the adenovirus genome into E1-expressing host cells. In a further embodiment, the transgene is Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3. In another embodiment, the promoter may be a cytomegalovirus (CMV) promoter and said poly A sequence is bovine growth hormone (BGH) poly A sequence.

Yet another embodiment of the invention is a method for constructing a recombinant adenovirus comprising: (a) providing a shuttle vector comprising an adenoviral inverted terminal repeat (ITR) sequence, an expression cassette comprising a promoter and poly-A signal sequence, a transgene under the control of said promoter, a tetracycline resistance-off responsive element, and unique restriction sites at the 5' and 3' ends of the IRT-promoter-transgene-poly-A segment; (b) cutting at said restriction enzyme sites; (c) ligating the released segment into an adenoviral vector comprising a tetracyclin resistant-off transactivator gene and lacking the entire E1 and E3 regions, and transforming the resulting vector a bacterial host cell; (d) obtaining vector from said bacterial host cell and digesting the vector to release the E1/E3-deleted adenovirus genome; and (e) transfecting the adenovirus genome into E1-expressing host cells. In a further embodiment, the transgene is Gene 26, PL6, Beta*, LUCA-1, LUCA-2, 123F2, Fus1, 101F6, Gene 21 or SEM A3. In another embodiment, the promoter may be a cytomegalovirus (CMV) promoter and said poly A sequence is bovine growth hormone (BGH) poly A sequence.

In yet another embodiment, also provided is a shuttle vector comprising an adenoviral inverted terminal repeat (ITR) sequence, an expression cassette comprising a promoter and poly-A sequence, a TetR-Off responsive element, and unique restriction sites at the 5'- and 3'-ends of the ITR-promoter-poly-A segment. In another embodiment of the invention the promoter is a cytomegalovirus (CMV) promoter and said poly A sequence is bovine growth hormone (BGH) poly A sequence. Also provided is a multipurpose cloning site in said segment, positioned between said promoter and said poly-A sequence.

Yet another embodiment is an adenoviral vector comprising a tetracycline resistant-off transactivator gene and lacking the entire E1 and E3-regions.

Another embodiment of the invention is a method of diagnosing cancer in a subject comprising the steps of: (i) obtaining a biological sample from said subject; and (ii) assessing the expression of a functional Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 product in sample. In a further embodiment the sample is a tissue sample. The tissue sample may be brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow or blood tissue. In another embodiment, the assessing comprises detecting a nucleic acid encoding Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3. Detecting may comprise amplification said nucleic acid, nucleic acid hybridization, or sequencing. In another embodiment, assessing comprises detecting a Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 polypeptide. The detecting of a Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 polypeptide may comprise ELISA or immunohistochemistry. In yet another embodiment, the assessing may comprise wild-type or mutant oligonucleotide hybridization, with said oligonucleotide configured in an array on a chip or wafer. In another embodiment of the invention, the expression of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 is compared with the expression of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 in normal samples. In another embodiment, the comparison involves evaluating the level of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), SEM A3 expression.

Another embodiment is a non-human transgenic animal lacking one or both functional alleles of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), SEM A3. Also provided is a non-human transgenic animal that overexpresses Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 0.26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 as compared to a similar non-transgenic animal. In a further embodiment is a non-human transgenic animal, the genome of which comprises an expression cassette comprising a Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 under the control of an inducible promoter.

An embodiment of the invention is a method for suppressing growth of a tumor cell comprising contacting said cell with an expression cassette comprising: (a) a nucleic acid encoding Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3; and (b) a promoter active in said tumor cell, under conditions permitting the uptake of said nucleic acid by said tumor cell. In another embodiment, the tumor cell is derived from a brain tumor, lung tumor, liver tumor, spleen tumor, kidney tumor, lymph node tumor, small intestine tumor, blood cell tumor; pancreatic tumor, colon tumor, stomach tumor, cervix tumor, breast tumor, endometrial tumor; prostate tumor, testicle tumor, ovarian tumor, skin tumor, head and neck tumor, esophageal tumor, oral tissue tumor, or bone marrow tumor. In a further embodiment, the nucleic acid is contained in a viral vector. The viral vector may be a retroviral vector, an adenoviral vector, and adeno-associated viral vector, a vaccinia viral vector, and a herpesviral vector. In yet another embodiment, the nucleic acid is contained in a liposome.

Another embodiment of the invention is a method of altering the phenotype of a tumor cell comprising contacting said cell with an expression cassette comprising: (a) a nucleic acid encoding Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 26 (CACNA2D2), PL6, Beta* (BLU), Luca-1 (HYAL1), Luca-2 (HYAL2), 123F2 (RASSF1), Fus1, 101F6, Gene 21 (NPRL2), SEM A3; and (b) a promoter active in said tumor cell, under conditions permitting the uptake of said nucleic acid by said tumor cell. In another embodiment, the phenotype is selected from the group consisting of proliferation, migration, contact inhibition, soft agar growth, cell cycling, invasiveness, tumorigenesis, and metastatic potential. In yet another embodiment, the promoter is a cytomegalovirus (CMV) promoter.

Another embodiment is a method of inhibiting cancer in a subject suffering therefrom comprising administering to said subject an expression cassette comprising: (a) a nucleic acid encoding Gene 26 (CACNA2D2), PL6, Beta* (BLU), Luca-1 (HYAL1), Luca-2 (HYAL2), 123F2 (RASSF1), Fus1, 101F6, Gene 21 (NPRL2), Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 polypeptide; and (b) a promoter active in tumor cells of said subject, whereby expression of said polypeptide inhibits said cancer. In a further embodiment, the subject is a human. In other embodiments, the nucleic acid encodes Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3. In another embodiment, the cancer is a selected from the group consisting of brain cancer, lung cancer, liver cancer, spleen cancer, kidney cancer, lymph node cancer, small intestine cancer, blood cell cancer, pancreatic cancer, colon cancer, stomach cancer, cervix cancer, breast cancer, endometrial cancer, prostate cancer, testicle cancer, ovarian cancer, skin cancer, head and neck cancer, esophageal cancer, oral tissue cancer, and bone marrow cancer. In yet another embodiment, the expression cassette is contained in a viral vector. The viral vector may be a retroviral vector, an adenoviral vector, and adeno-associated viral vector, a vaccinia viral vector, and a herpesviral vector. In another embodiment, the expression cassette is contained in a lipsome. In another embodiment, the expression cassette further comprises a poly-A sequence. The poly-A sequence may be a bovine growth hormone (BGH) poly-A sequence. In a further embodiment, the expression cassette is administered intratumorally, in the tumor vasculature, local to the tumor, regional to the tumor, or systemically.

Also provided in the method of inhibiting cancer is the administering of a chemotherapuetic agent to said subject. In another embodiment, the chemotherapeutic comprises cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate. Also provided is the administering radiation to said subject. In another embodiment, the radiation is delivered local to a cancer site or is whole body radiation. The radiation may comprise γ-rays, X-rays, accelerated protons, microwave radiation, UV radiation or the directed delivery of radioisotopes to tumor cells. In yet another embodiment, a second anticancer gene may be administered to said subject. The second anticancer gene may be a tumor suppressor. The second anticancer gene may be an inhibitor of apoptosis. In another embodiment, the second anticancer gene is an oncogene antisense construct.

An embodiment of the invention is a method of treating a subject with cancer, comprising the step of administering to said subject a Gene 26 (CACNA2D2), PL6, Beta* (BLU), Luca-1 (HYAL1), Luca-2 (HYAL2), 123F2 (RASSF1), Fus1, 101F6, Gene 21 (NPRL2), SEM A3 polypeptide. In another embodiment, the cancer is a selected from the group consisting of brain cancer, lung cancer, liver cancer, spleen cancer, kidney cancer, lymph node cancer, small intestine cancer, blood cell cancer, pancreatic cancer, colon cancer, stomach cancer, cervix cancer, breast cancer, endometrial cancer, prostate cancer, testicle cancer, ovarian cancer, skin cancer, head and neck cancer, esophageal cancer, oral tissue cancer, and bone marrow cancer. In a further embodiment, the polypeptide is contained within a liposome. the liposome may be comprised of N-(1-[2,3-Dioleoyloxy]propyl)-N,N, N-trimethylammonium (DOTAP) and cholesterol. In another embodiment, the subject is human.

Another embodiment of the invention is a method of screening a candidate substance for anti-tumor activity comprising the steps of: (i) providing a cell lacking a functional Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 polypeptide; (ii) contacting said cell with said candidate substance; and (iii) determining the effect of said candidate substance on said cell. In another embodiment, the cell is a tumor cell. In another embodiment, the determining may comprises comparing one or more characteristics of the cell in the presence of said candidate substance with the same one or more characteristics of a similar cell in the absence of said candidate substance. In a further embodiment, the characteristic is selected from the group consisting of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), SEM A3 expression, phosphatase activity, proliferation, metastasis, contact inhibition, soft agar growth, cell cycle regulation, tumor formation, tumor progression, metastasis and tissue invasion. In another embodiment, the candidate substance is a chemotherapeutic or radiotherapeutic agent. Also provided is a candidate substance selected from a small molecule library. In further embodiments, the cell is contacted in vitro or in vivo.

An embodiment of the invention is a method of screening a candidate substance for anti-tumor activity comprising the steps of (i) providing a cell; (ii) contacting said cell with said candidate substance; and (iii) determining the effect of said candidate substance on expression of a Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3 polypeptide.

Another embodiment is a method of producing a Beta* polypeptide in a host cell comprising: (a) providing an expression cassette comprising a nucleic acid encoding Beta* operably linked to an promoter active in said host cell; (b) transferring said expression cassette into said host cell; and (c) culturing said host cell under conditions permitting expression of said Beta* polypeptide.

Yet another embodiment of the invention is a method of diagnosing cancer in a subject comprising the steps of: (i) obtaining a biological sample from said subject; and (ii) detecting hypermethylation of the promoter region of Gene 26 (CACNA2D2), PL6, Beta* (BLU), Luca-1 (HYAL1), Luca-2 (HYAL2), 123F2 (RASSF1), Fus1, 101F6, Gene 21 (NPRL2), or SEM A3.

Other objects, features and advantages of the present invention will become apparent from the following detailed description. It should be understood, however, that the detailed description and the specific examples, while indication preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 4A-1-FIG. 4B-3. Allelotyping of 3p region in DNAs from human lung cancer cell lines and tumors. Filled ovals=loss of heterozygosity; open ovals=retaining of alleles; and hatched ovals=homozygous deletions.

FIG. 9A-1-9B-6. Effect of overexpression of 3p genes on cell cycle kinetics in Ad-3p-transduced human lung cancer cells A549 and H1299.

FIG. 12A-12D. Map of the RASSF1 locus, transcripts, and protein domains, A) The exon-intron structure of the RASSF1 locus with the location of the CpG islands in the predicted promoter regions (the locations of which are shown by double-headed arrows) of RASSF1A and RASSF1C. RASSF1A transcription is predicted to come from the most centromeric promoter region located within a CpG island and begins with exon 1A. RASSEiF also commences at this promoter but is missing exon iC. Transcription of RASSFIC is predicted to begin in the most telomeric promoter region, which is approximately 2 kilobases from that of RASSF1A and begins with exon 1. Blocks represent exons; lines represent introns. B) Schematic of the RASSF1A transcript and predicted protein-sequence domains. The location of the various primers (PKCDF, NF, R182, and R292) used for isoform-specific reverse transcription (RT)-polymerase chain reaction (PCR) analyses are indicated. Tick marks identify the exon boundaries. The potential arc homology 3 (5H3)-binding region, putative diacylglycerol (DAG)-binding domain, PEST sequence, Rasassociation domain, and ataxia-telangiectasia-mutated (ATM) phosphorylation site are labeled. C) Schematic of the RASSFIC transcript and predicted protein-sequence domains. The locations of the various primers (NOX3, R182, and R292) used for isoform-specific RT-PCR analyses are indicated. D) Schematic of the RASSFIF transcript and predicted protein-sequence domains.

FIG. 13A-13C. RASSF1A and RASSF1C messenger RNA levels detected by isoform-specific reverse transcription-polymerase chain reaction (RT-PCR) in a sampling of lung cancer cell lines (A), breast cancer lines (B), and resected lung tumors and normal human lung and breast epithelial cultures (C). All RT-PCR products were separated on 2% agarose gels and were identified by staining with ethidium bromide. Arrows indicate location of transcripts. A) Lung cancer lines tested in lanes: 1—11157; 2=11358; 3=11727; 4=11740; 5=11748; 6=11838; 7=111184; 8=111299; 9=111304; 10=111437; 11=111450; 12=111770; 13=111792; 14=111963; 15 111993; 16=112009; 17=112077; iS=112108; 19=11HCC44; and 20=HCC78. B) Breast cancer lines tested in lanes: 1=11CC38; 2=11CC1187; 3=HTB19; 4=HTB2O; 5=HTB22; 6=11TB23; 7=11TB24; 8=11TB25; 9=11TB26;

10=11TB27; 11=HTB121; 12=HTB129; 13 HTB13O; 14=HTBI31; 15=HTB132; 16=H'T'B133; 17=11CC 1395; iS=11CC 1428; 19=11CC1569; 20=11CC1806; and 21=11CC2157. C) Resected lung adenocarcinoma samples (ADC 1-5) and cultures of normal small-airway epithelial cells (SAECs), normal human bronchial epithelial (NHBE) cultures, and normal human breast epithelial (NHBRE) cultures.

Figure 14:
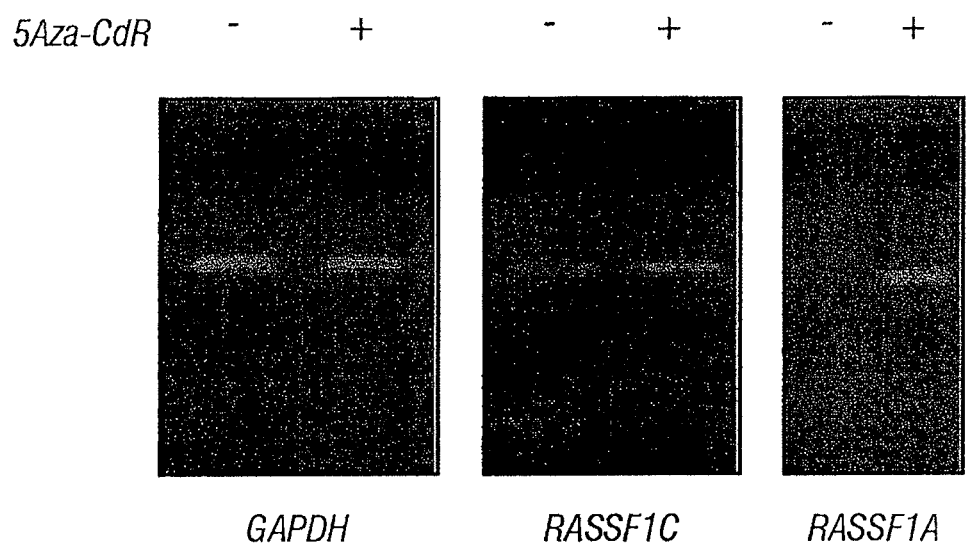

FIG. 14. Expression of RASSF1A after treatment of lung cancer cells with 5-aza-2'-deoxycytidine (SAza-CdR). NCI-11157, a non-small-cell lung carcinoma (NSCLC) cell line that expresses RASSFIC but not RASSFIA, was grown in the presence (+lanes) and absence (−lanes) of 0.5 p.M SAza-CdR for 48 hours. Total RNA was isolated, complementary DNA was prepared, and isoform specific reverse transcription-polymerase chain reaction was performed for RASSF1A, RASSF1C, and glyceraldehyde-3-phosphate dehydrogenase (GAPDH) as a control.

Figure 15:
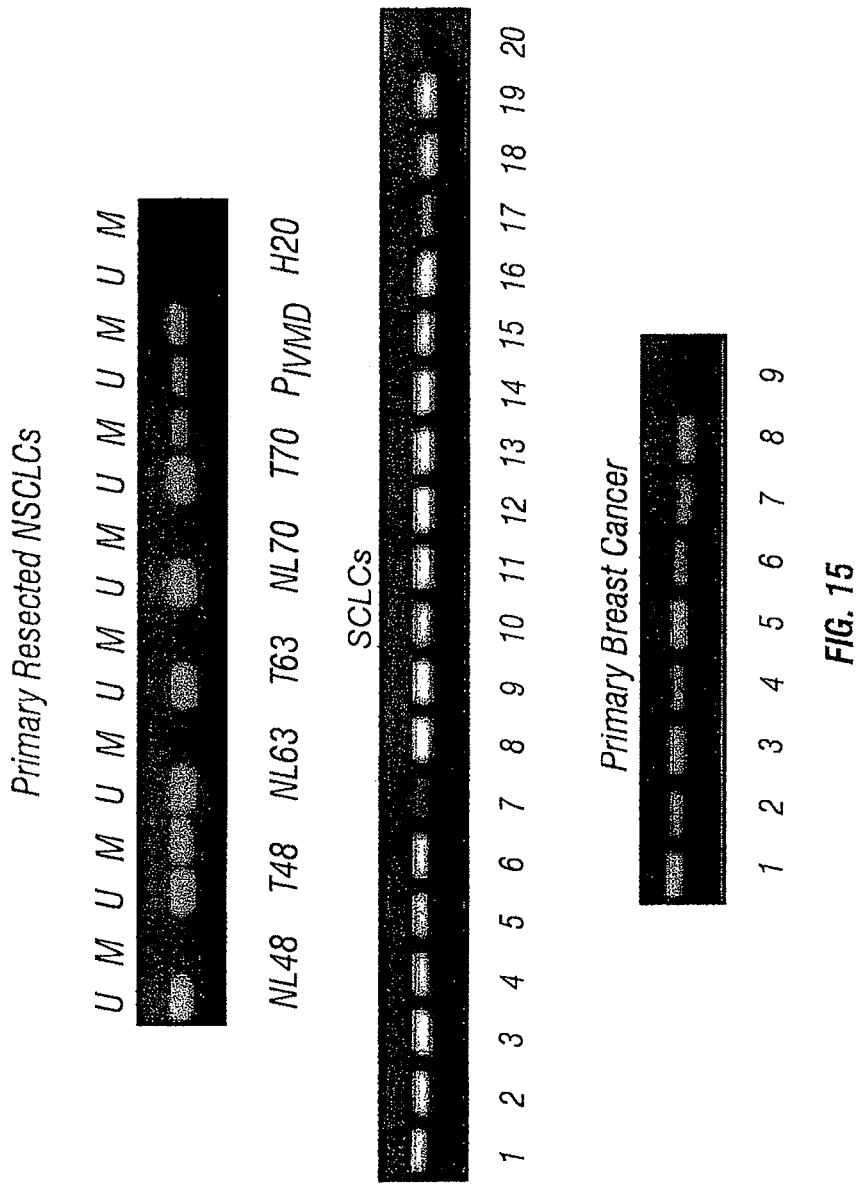

FIG. 15. Methylation-specific polymerase chain reaction (PCR) for the detection of methylated RASSF1A 5, CpG sequences in primary resected non-small-cell lung carcinomas (NSCLCs) and their accompanying normal lung tissue (upper panel), small-cell lung carcinoma (SCLC) cell lines (middle panel), and primary breast cancers (lower panel). Representative samples are shown. For resected NSCLCs, U=results with primers specific for unmethylated sequences; M=results with primers specific for methylated sequences. NL=normal lung tissue; T=tumor; P=results with peripheral blood lymphocyte DNA, which is unmethylated or in vitro methylated (IVMD); and 1120=negative controls with water blanks. For SCLCs, each lane shows the PCR results for the methylated sequences from a different cell line. Lane 20 is negative control. For the breast cancers, each lane shows the PCR results for methylated sequences from a different sample. PCR products were separated on 2% agarose gels and bands were detected after staining with ethidium bromide.

Figure 16:
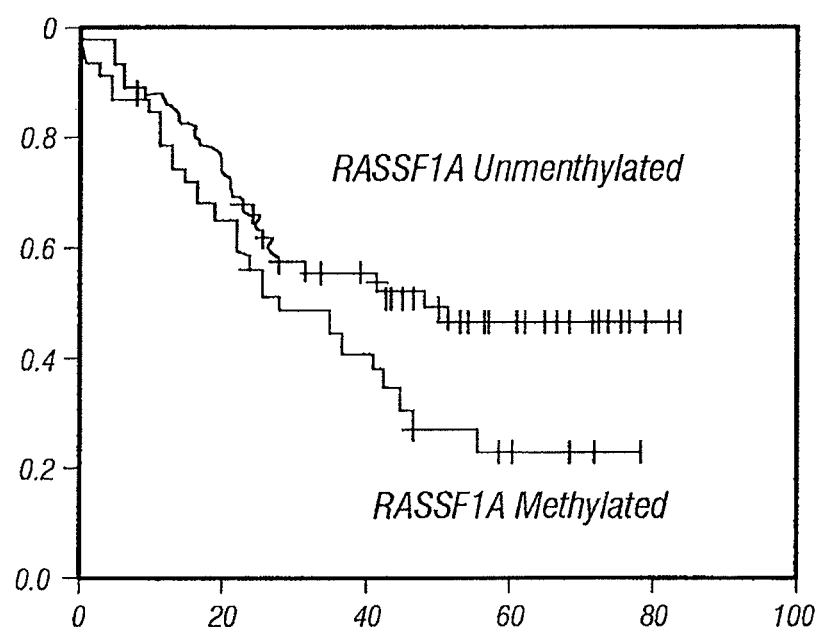
Figure 17A:
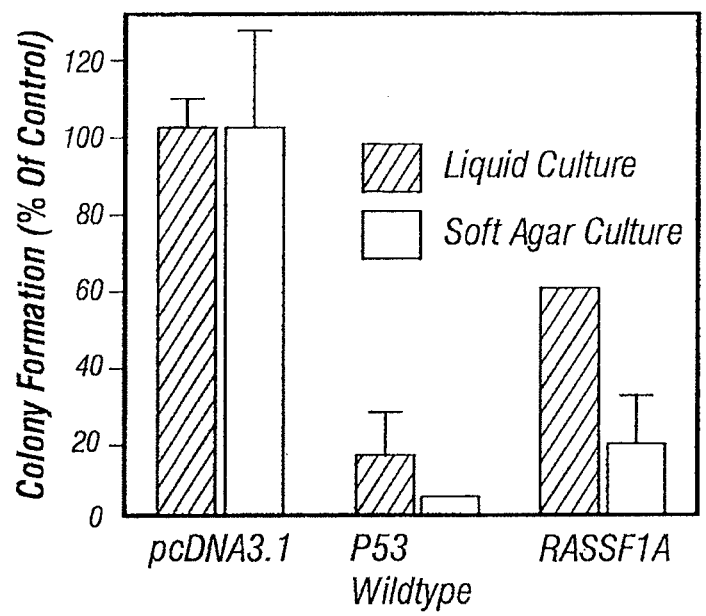
Figure 17B:
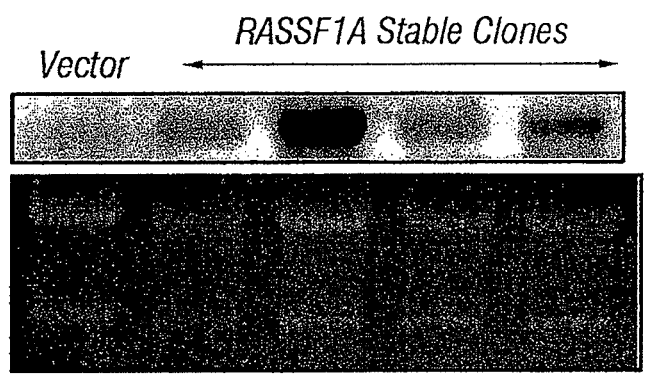
Figure 17C:
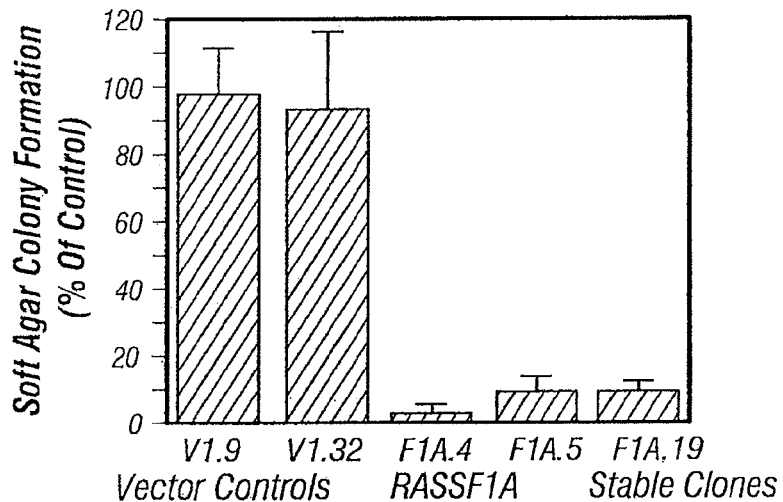
Figure 17D:
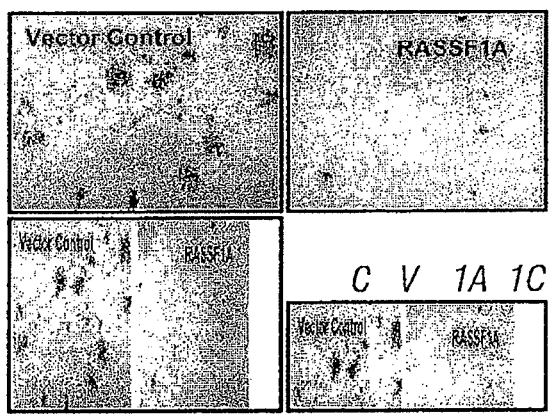
Figure 17E:
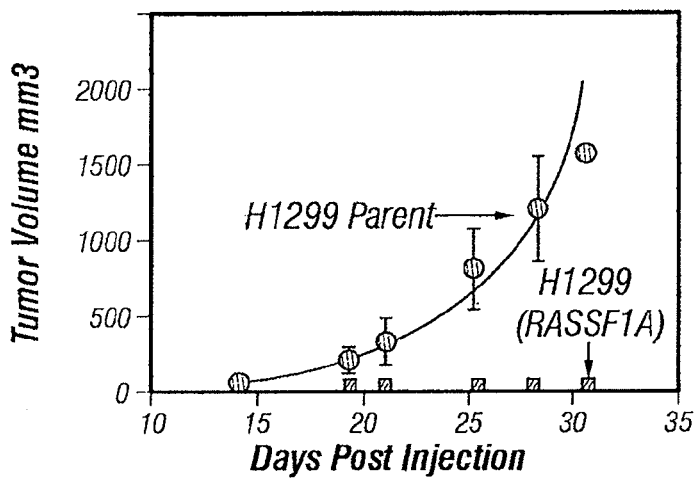

FIG. 16. Kaplan-Meier survival curve for 107 patients with resected non-small-cell lung carcinomas based on RASSF1A methylation status (32 methylated and 75 not methylated), For the patients with unmethylated RASSF1A alleles, the number of cases=75, censored=39, and events=36, with a mean overall survival of 52 months (95% confidence interval [CI]=44 to 59) and a median overall survival of 49 months (95% CI=44 to 59); for the patients with methylated RASSF1A alleles, the number of cases=32, censored=nine, and events=23, with a mean overall survival of 37 months (95% CI=27 to 46) and a median overall survival of 28 months (95% CI=9 to 47). The log-rank test statistic for equality of survival distributions for RASSF1A methylation was 3.97, with df 1, P=0.0463. The patients at risk for each group were: RASSF1A unmethylated-12 months (n=63), 36 months (n=34), and 60 months (n=16); RASSFIA methylated-12 months (n=24), 36 months (n=13), and 60 months (n=5).

FIG. 17A-17E. Effect of RASSF1A on the in vitro and in vivo growth of the non-small-cell lung carcinoma (NSCLC) cell line NCI-111299. A) Anchorage-dependent and anchorage-independent colony formation after transfection of NCI-H1299 cells with the ~ioo empty vector (pcDNA3.1+) or peDNA3.1+ expression vectors containing wild-type p53 or RASSF1A. For analysis of anchorage-dependent growth, after 2 days in nonselective growth medium, transfected NCI-111299 cells were diluted into 100-mm$^2$ dishes with selective medium. Transfected cells were plated in liquid medium (for anchorage-dependent assays) or soft agar (for anchorage-independent assays) containing 800 p.g/mL of G418. Colonies were stained with methylene blue in anchorage-dependent experiments after 14 days. Results represent the average of eight to 12 experiments in liquid medium and three soft-agarexperiments. Standard deviations are shown or are less than 2%. Solid bars .=anchorage-dependent growth (95% confidence interval [CI]=0 to 36 for wt-p53 (wild-type) and 52 to 60 for RASSFIA); open bars=anchorage-independent growth (95% CI=0 to 6 for wild-type (wt)-p53 and 0 to 39 for RASSFIA). B) Northern blot analysis of the RASSF1A expression in stable clones of NCI-H1299 cells transfected with the pcDNA3.1+ vector or pcDNA3.1+ containing RASSF1A complementary DNA (cDNA). The vector control (vector) and four separate clones with various RASSF1A messenger RNA levels are shown. Several of these clones were used in the anchorage-independent growth assay shown in D. Ethidium bromide staining of the ribosomal RNA is shown as a loading control. The clones were also verified to express the RASSF1A isoform by reverse transcription-polymerase chain reaction with the use of isoform-specific primers. C) Soft-agar (anchorage-independent) colony formation in stable clones of NCI-111299 cells transfected with the pcDNA3.1+ vector or pcDNA3.1+ containing RASSF1A cDNA. The means and standard deviations are shown. For each of the RASSFIA-expressing clones, the 95% CI=0 to 4 for F1A.4, 2 to 16 for F1A.5, and 3 to 14 for F1A.19. D) NCI111299 cells were infected with the pBABEpuro retrovirus expression vectors containing either the vector control or the RASSF1A or RASSF1C cDNAs. Infected cells (10000 per plate) were suspended in 0.33% agar, and the suspension was layered over a 0.5% agar base. Colonies greater than 0.2 mm in diameter were counted after 21 days. The lower right panel shows a representative western blot, developed with a rabbit antibody to the RASSF1-glutathione S-transferase fusion protein, to verify the expression of the RASSF1 proteins. C=positive control generated by transient transfection of NCI-111299 cells with peDNA3.1+ containing RASSF1A cDNA; V=infection of NCI-H1299 cells with the retroviral vector control (note runover from positive control; 1A=infection of NCI-H1299 cells with the retroviral vector containing RASSF1A; and 1C=infection of NCI-H 1299 cells with the retroviral vector containing RASSF1C. E) Effect of RASSF1A on the in vivo growth of NCI-111299 cells. Approximately 10$^7$ viable NCI-H 1299 cells expressing RASSF1A were injected into the flanks of each of five previously irradiated BALB/c (nulnu) nude mice. Tumor size was monitored overtime, and size is shown in cubic millimeters. The average volume of tumors grown in more than 20 mice that were given an injection of vector-transfected NCI-H 1299 cells is shown (H1299 parent). Mice that were given an injection of RASSFIA-infected NCI-H 1299 cells grew no measurable tumors.

Figure 18:
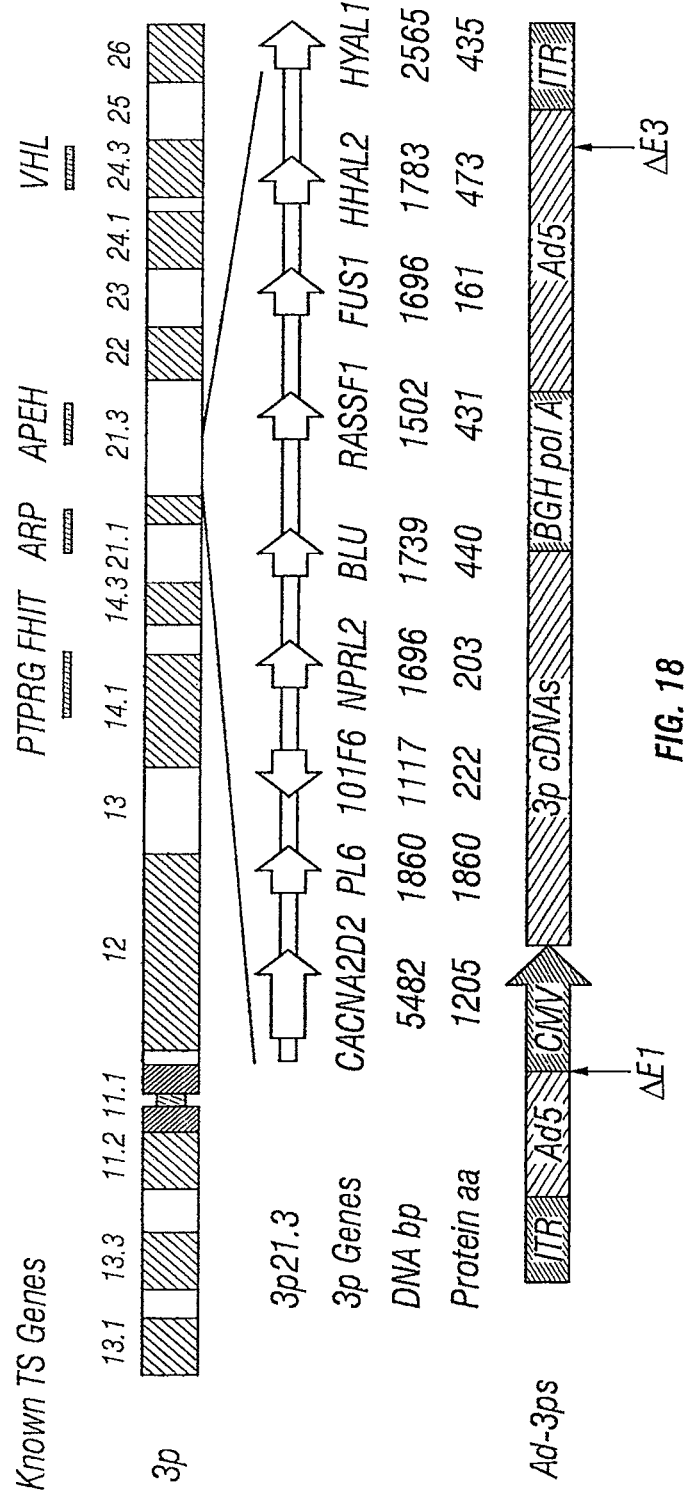
Figure 19A:
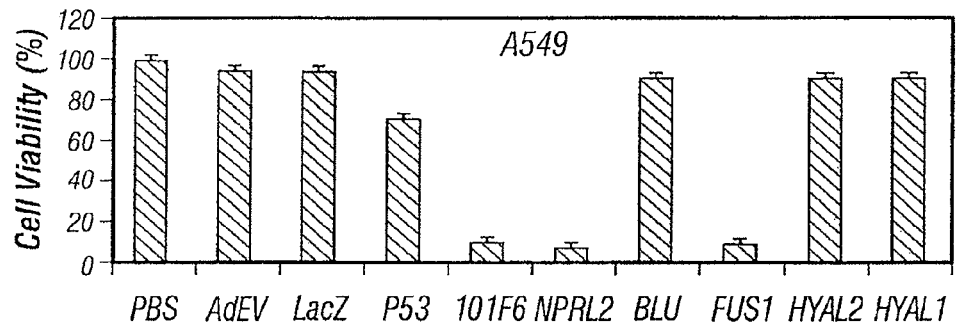
Figure 19B:
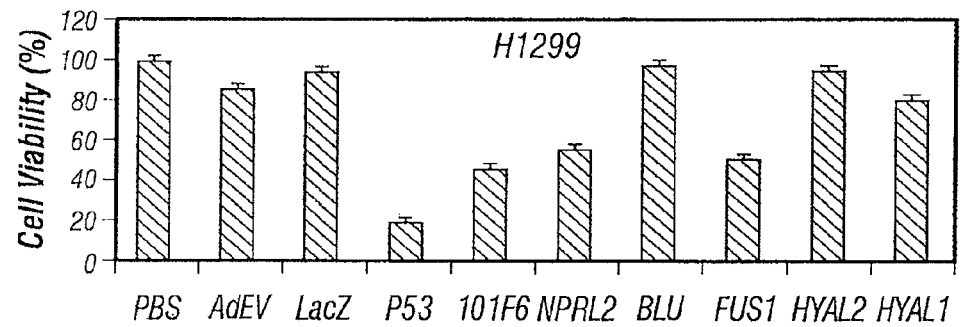
Figure 19C:
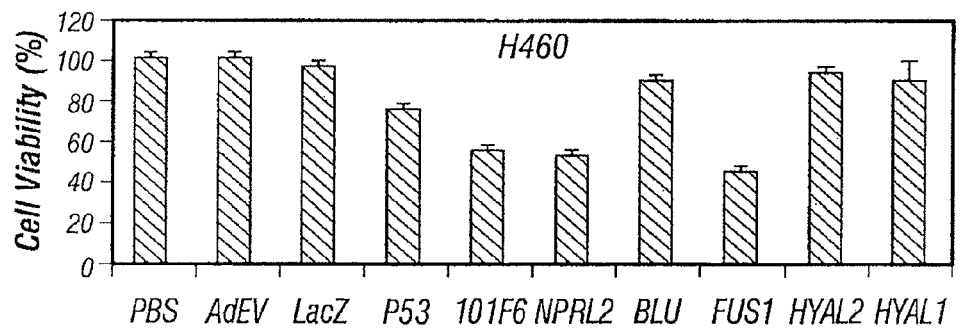
Figure 19D:
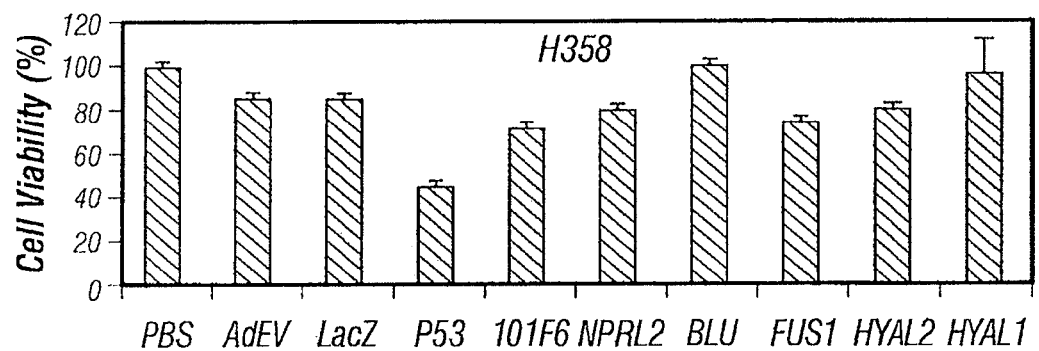
Figure 19E:
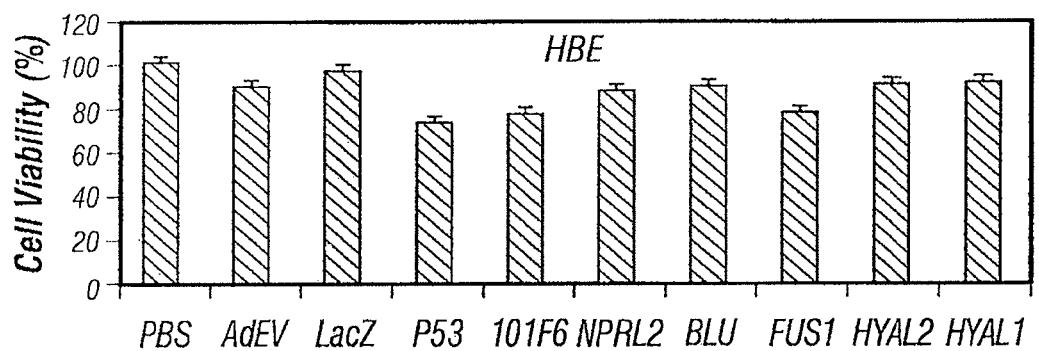
Figure 20A:
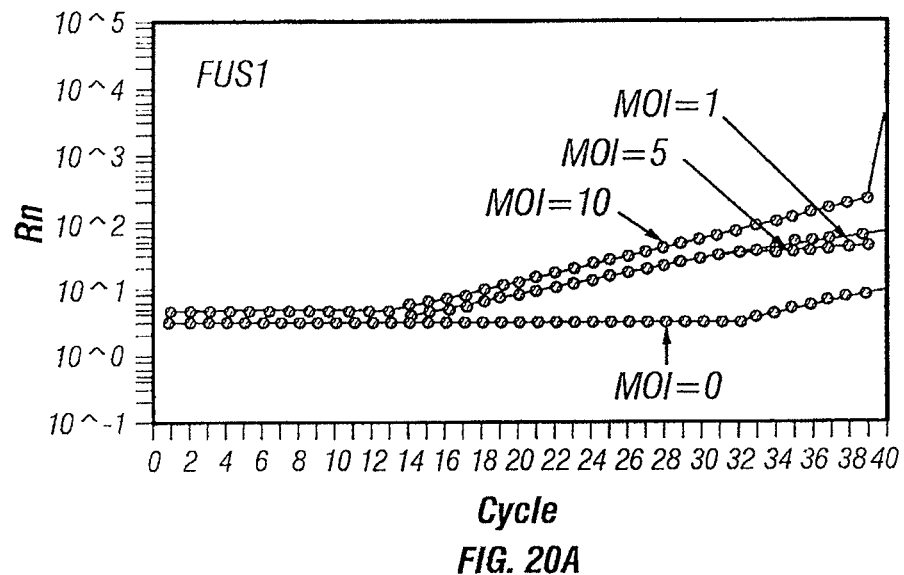
Figure 20B:
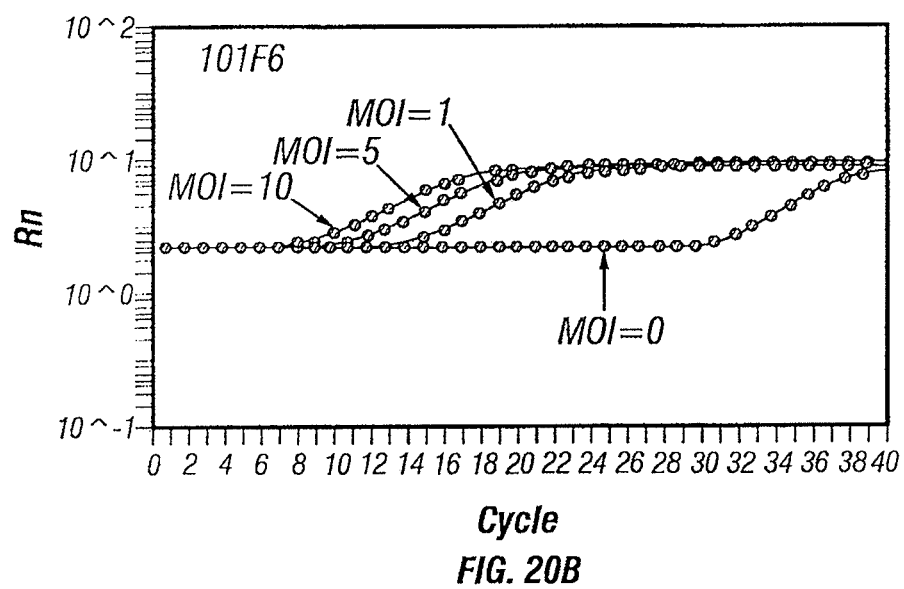
Figure 20C:
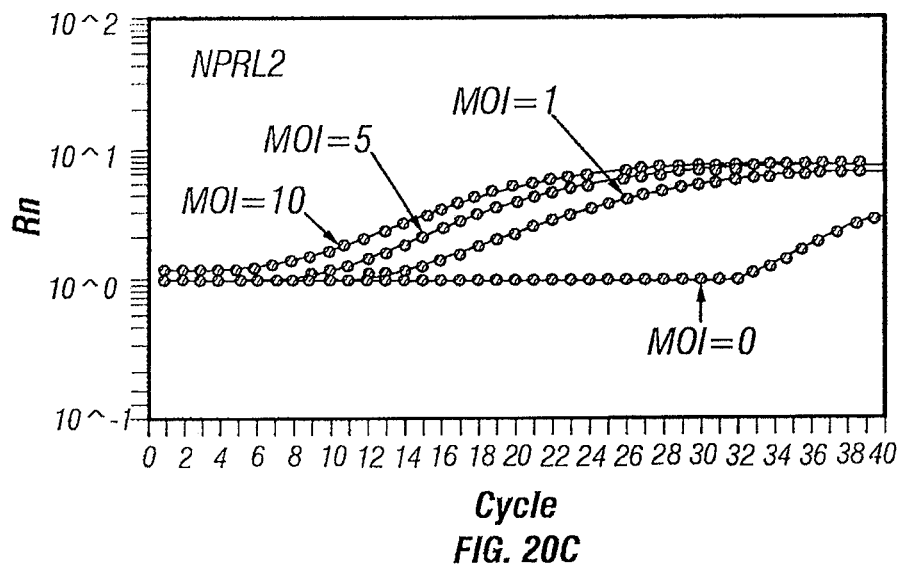
Figure 20D:
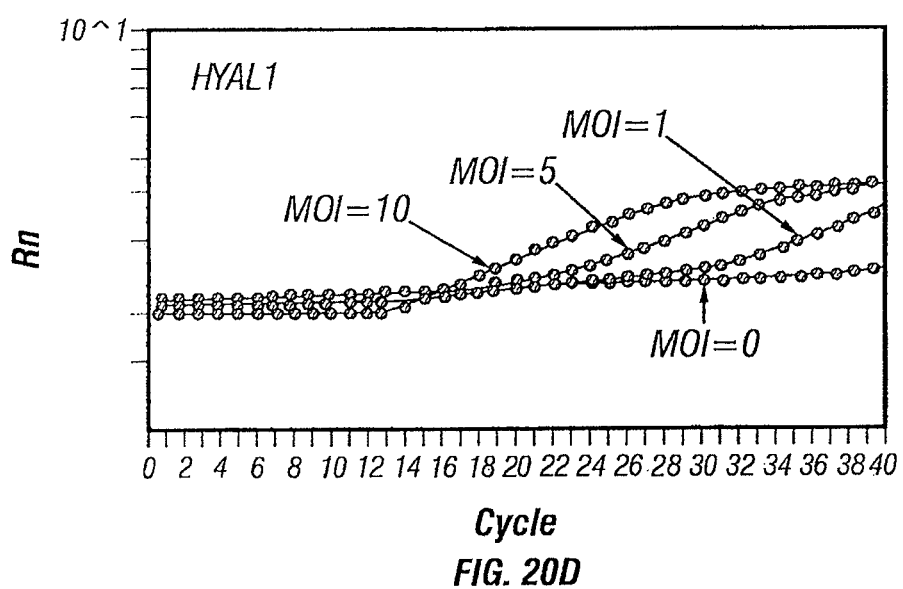
Figure 21A:
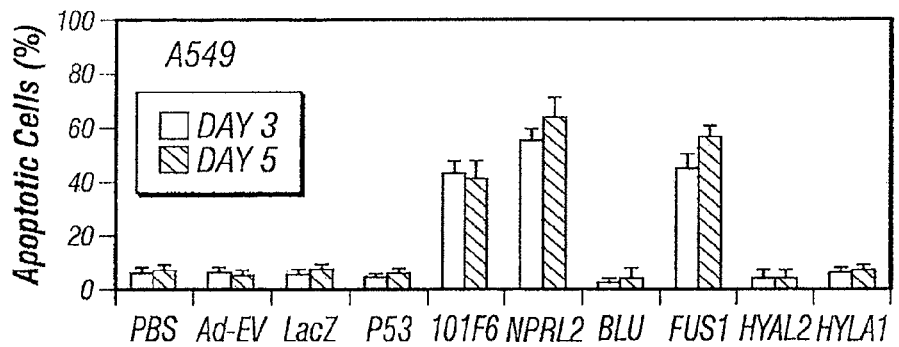
Figure 21B:
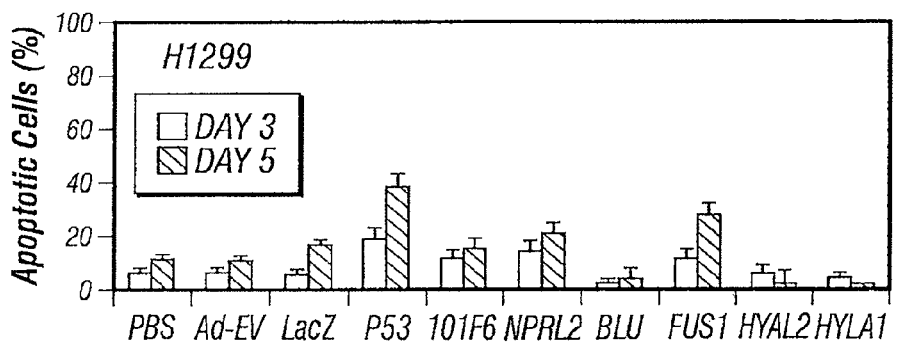
Figure 21C:
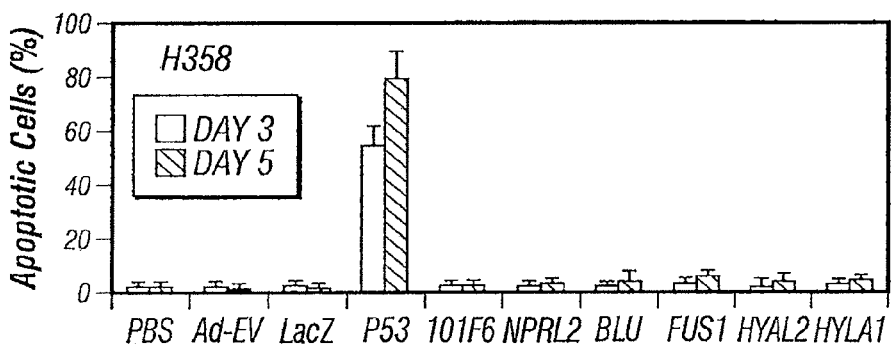
Figure 21D:
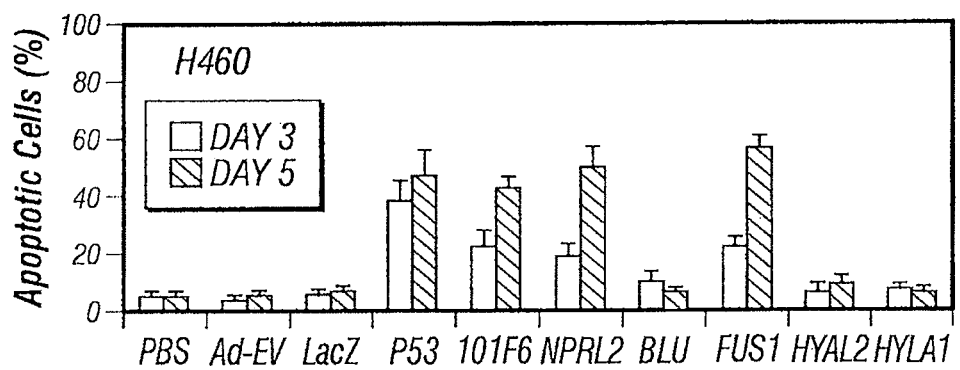
Figure 21E:
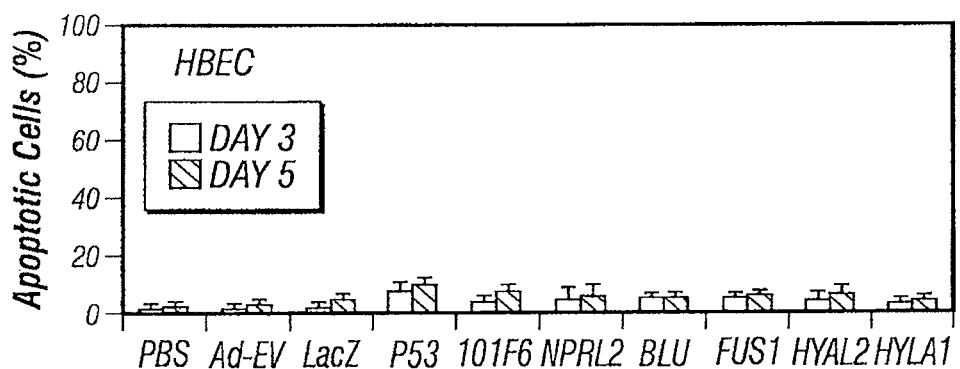

FIG. 18. Schematic representation of the location of the putative 3p21.3 tumor suppressor region in human chromosome 3p and the structure of the recombinant adenoviral vectors of 3p21.3 genes. The sizes of the individual 3p21.3 genes and their corresponding amino acid residues deduced from coding sequences of cDNAs, and the active tumor suppressor (TS) regions and known TSGs in the 3p are indicated. The recombinant adenoviral vectors of 3p21.3 genes (Ad-3ps) were constructed by inserting a mammalian expression cassette in which the 3p21.3 gene was driven by a CMV promoter and tailed with BGH poly A signal sequence into the E1-deleted region of the replication incompetent adenovirus type 5 (Ad5) genome. The relative locations of E1-deletion (ΔE1) and E3-deletion (ΔE3), the inverted repeated terminal (IRT) sequences in the Ad5 genome are indicated.

FIG. 19A-19E. Effects of exogenous expression of 3p21.3 genes on tumor cell growth in Ad-3p-transduced human lung cancer cells and normal bronchial epithelial cells. Cells were transduced with adenoviral vectors of 3p21.3 genes, 101F6, NPRL2, BLU, RASSF1C FUS1, HYAL2, and HYAL1, control genes, LacZ and p53, and empty vector, Ad-EV, at highest MOIs (vp/c), 5000 for A549, 1000 for H1299, 5000 for H460, 2500 for H358, and 1000 for HBE, respectively, and PBS alone was used as a mock control. The cell viability was expressed as the percentage of viable adenoviral vector-transduced cells in relation to PBS-treated control cells (100%). The error bars represent standard deviations of the mean in at least three individual experiments. Treatments were given in quadruplicate for each experiment. The significance of the difference in cell viability between vector-treated cells and the Ad-EV-, Ad-LacZ-, or PBS-treated controls was analyzed by two-sided Student's T-test. $P<0.05$ was taken as significant. The differences between the cell viability of the Ad-EV- and Ad-LacZ-transduced cells versus PBS-treated controls were not significant ($P=0.25$ to $P=0.95$ from different time points and cell lines). The differences between the cell viability of the Ad-101F6, Ad-Fus1, and Ad-NPRL2-transduced cells versus the Ad-EV-, Ad-LacZ-transduced, or PBS-treated controls at same MOIs were significant in A549, H1299, and in H460 at both 3 days and 5 days posttransduction. ($P≤0.0001$ to $P≤0.005$) but not significant in H358 and HBEC cell lines at both 3 and 5 days posttransduction ($P≥0.10$ to $P≥0.95$, from different time points and cell lines), respectively. The effects of Ad-BLU, Ad-HYAL2, and Ad-HYAL1 on cell viability were not significant in all cell lines ($P>0.45$) compare to those of Ad-EV and Ad-LacZ.

FIG. 20A-20D. Quantification of adenovirus-mediated 3p21.3 gene expression in H1299 cells by real-time RT-PCR. The real-time RT-PCR was performed and PCR profiles were generated by an ABI Prism 7700 Sequence Detection system and equipped software (Perkin Elmer Applied Biosystems). Known concentrations of β-Actin DNA were used as a standard. The H1299 cells were transduced by adenoviral vectors of 3p21.3 genes, FUS1 (A), 101F6 (B), NPRL2 (C), and HYAL1 (D) at a MOI of 1, 5, and 10 pfu/cell for 48 hr, respectively, as indicated by arrows.

FIG. 21A-21E. Induction of apoptosis by exogenous expression of 3p21.3 genes in Ad-3p-transduced human NSCLC cells and normal HBECs. Apoptosis were analyzed by FACS, using TUNEL reaction with FITC-labeled dUTP. Cells were transduced with adenoviral vectors of 3p21.3 genes at an MOIs (vp/c) of 5000 for A549 (A), 1000 for H1299 (B), 5000 for H460 (C), 2500 for H358 (D), and 1000 for HBEC (E), respectively, and PBS, Ad-EV, and p53 were used as controls. Cell were harvested and analyzed for apoptosis at the indicated days posttransduction. The rate of apoptosis is expressed as the percentage of FITC-labeled cells in the total cell population. The error bars represent standard deviations of the mean in two or three repeated experiments with triplicate treatments and TUNEL reactions for each experiment. The significance of the difference in apoptosis between vector-treated cells and the Ad-EV-, Ad-LacZ-, or PBS-treated controls was analyzed by two-sided Student's T-test. $P<0.05$ was considered significant. The differences between the apoptosis induced by the Ad-EV- and Ad-LacZ-transduced cells versus PBS-treated controls were not significant ($P=0.925$ to $P=0.675$ from different time points and cell lines). The differences between the apoptosis induced in the Ad-101F6, Ad-FUS1, and Ad-NPRL2-transduced cells versus the Ad-EV-, Ad-LacZ, or PBS-treated controls were significant in A549 and H460 cells at both 3 days and 5 days posttransduction ($P≤0.0001$ to $P≤0.005$), and significant versus the Ad-EV- and PBS-treated cells in H1299 at 5 days posttransduction ($P≤0.02$), but not significant in H358 and HBEC cell lines at both 3 and 5 days posttransduction at all time points ($P≥0.85$ to $P≥0.95$), respectively. Induction of apoptosis in Ad-p53-transduced H358 cells were significant at all time points compared to all other treatments ($P<0.0001$). Induction of apoptosis in cells treated with Ad-BLU, Ad-HYAL2, and Ad-HYALyall was not significant compared to those treated with PBS, Ad-EV, or Ad-LacZ, in all cell lines at all time points ($P>0.85$).

Figure 22A:
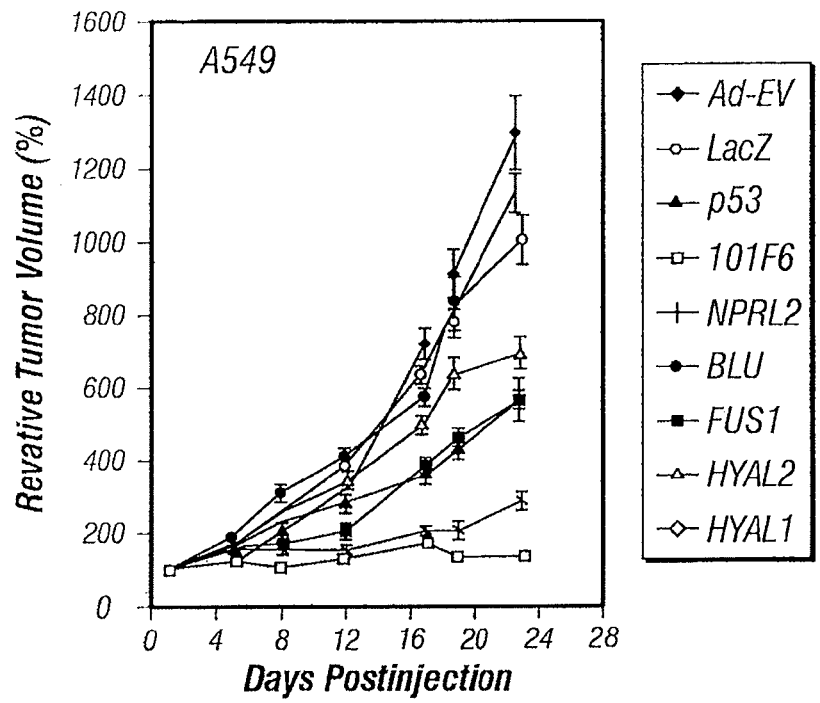
Figure 22B:
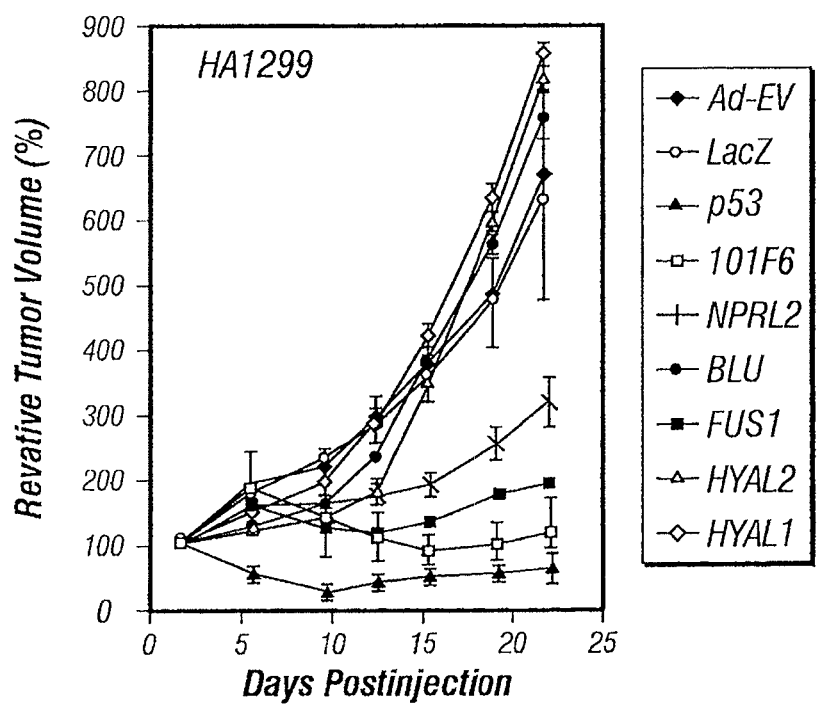

FIG. 22A-22B. Effects of intratumoral administration of adenoviral vectors of 3p21.3 genes on growth of human lung cancer A549 (A) and H1299 (B) subcutaneous tumors in nu/nu mice. When the tumor reached 5 to 10 mm in diameter at about 2 weeks after tumor inoculation, the tumor was injected with individual adenoviral vectors of 3p21.3 genes, 101F6, NPRL2, BLU, RASSF1CFUS1, HAYL2, and HYAL1 or control vectors Ad-EV, LacZ, and p53, at a dose of $5\times10^{10}$ vp/tumor each in 200 μl of PBS for three times within a week, respectively, and PBS alone was used as a mock control. Results were reported as the mean±SD in 5-10 mice for each treatment group. Tumor volumes were normalized by the percentage increase of tumor sizes after treatment relative to those at the beginning of the treatment in each group. Mean tumor volumes ±SE from these experiments are shown. ANOVA was performed to determine statistical significance between each treatment group using a Statistica software (StatSoft Inc.) and $P≤0.05$ was considered significant. The differences betweof en the tumor volumes ofin the Ad-101F6, Ad-FUS1, Ad-NPRL2-treated mice versus in the Ad-EV- and Ad-LacZ-treated mouse controls were statistically significant in both A549 and H1299 tumor models ($P<0.0001$), and the difference in the Ad-HYAL2-treated mice was significant in A549 ($P=0.024$) but not in H1299 tumor models, after 5 days from the last injection ($P<0.0001$), but not significant in Ad-HYAL1, Ad-HYAL2, Ad-RASSF1C, and Ad-BLU-treated ($P>0.05$ in both A549 and H1299 tumor models).

Figure 23A:
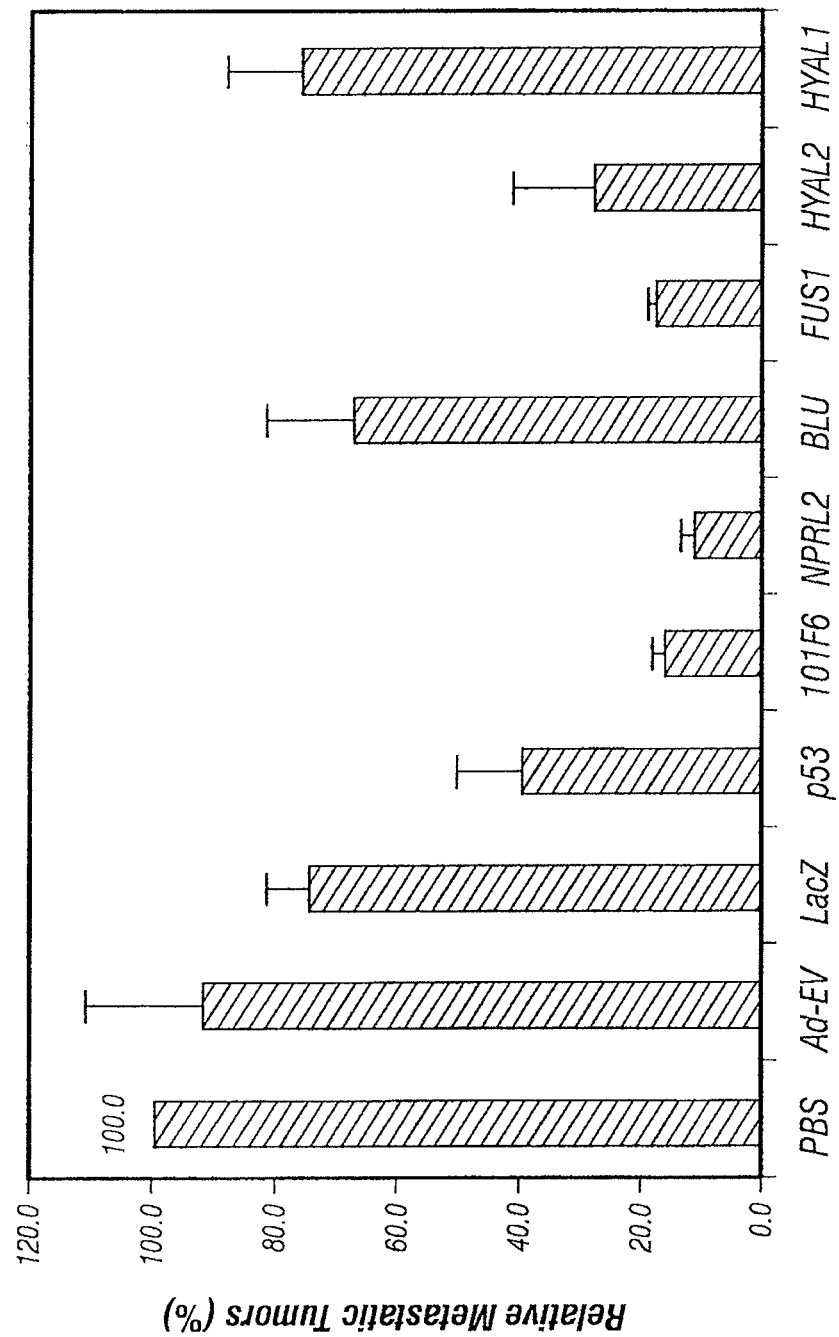
Figure 23B:
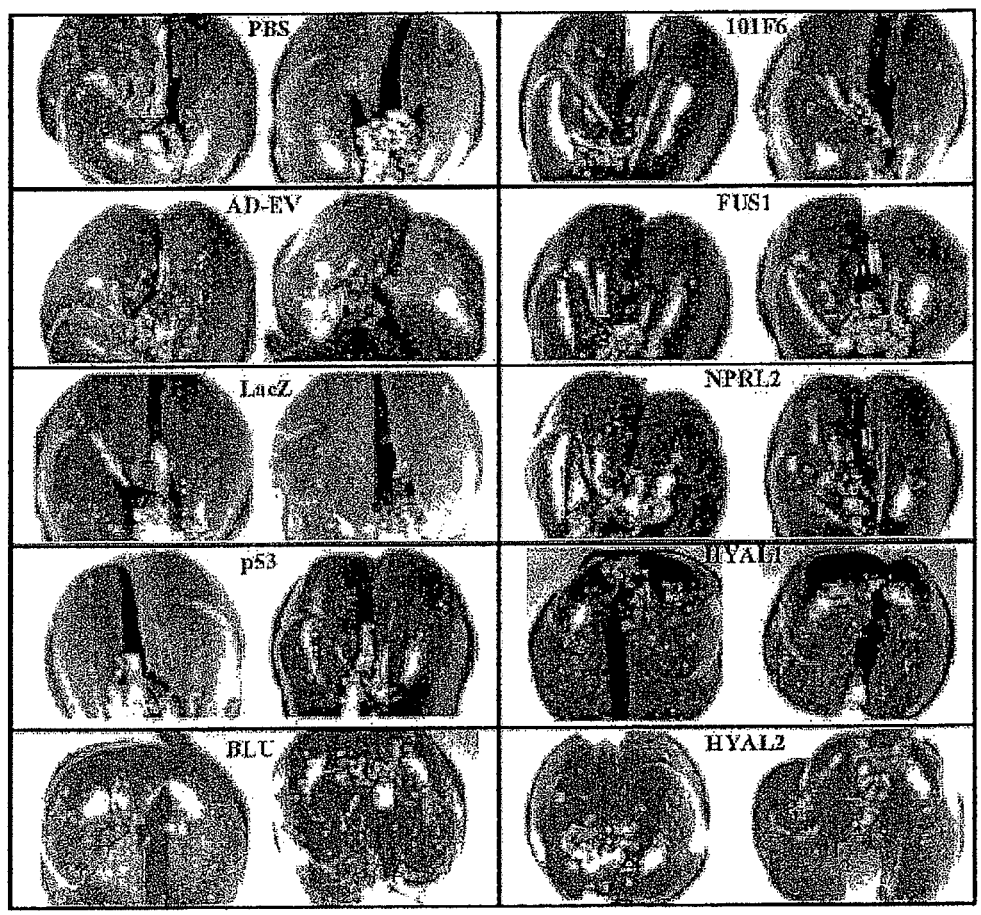

FIG. 23A-23B. Effect of systemic administration of protamine-Ad-3p complexes on development of A549 experimental lung metastases in nu/nu mice. A., Relative metastatic tumors in mice treated with P-Ad-3p21.3 genes. All animals were i.v. injected with various protamine-adenoviral vector complexes every other two days for 3 times each at a dose of $3\times10^{10}$ viral particles plus 300 μg protamine in a total volume of 200 μl per animal, and PBS alone was used as a mock control. Each treatment group consisted of 5-10 animals. Lungs were harvested two weeks after the last injection and metastastic colonies on the surfaces of lung were counted without knowledge of the treatment groups. Development of metastases were represented as the percentages of metastatic colonies formed in protamine-adenovirus complexes-treated groups in relation to those in the PBS-treated group (as 100%). Error bars represent as standard error (SE). Non-parametric t-test (Wald-Wolfowitz Runs Test) was performed to determine statistical significance between each treatment group using a Statistica software (StatSoft Inc.) and $P≤0.05$ was considered significant. A significant inhibition of development of metastases was observed in mice treated with P-Ad-101F6 ($P=0.002$), P-Ad-NPRL2 ($P=0.001$), P-Ad-BLU ($P=0.018$), P-Ad-FUS1 (P=0.002), and P-Ad-HYAL2 (P=0.014), respectively, compared to mice treated with PBS, P-Ad-EV, or P-Ad-LacZ, but no significant inhibition in mice treated with. P-Ad-BLU (P=0.818) or P-Ad-HYAL1 (P=0.904). B., the representative photos of lungs stained with India ink for metastases. The metastatic colonies were shown as white spots on the surfaces of lung.

Figure 24A:
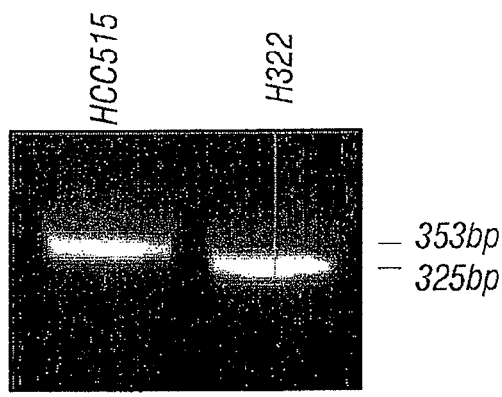
Figure 24B:
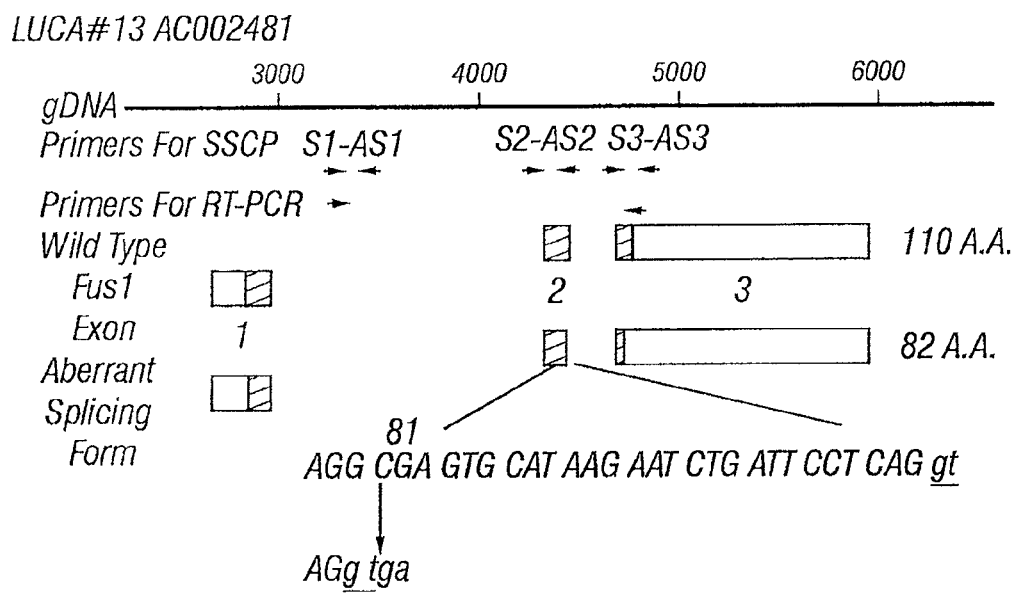

FIG. 24A-24B (a) RT-PCR Analysis of NSCLCs cDNA HCC515 (Wild type FUS1) and H322 (smaller cDNA mutant form of FUS1). (b) Genomic structure of wild type FUS1 and the mutant aberrant slicing form. Top line is genomic DNA from cosmid clone LUCA#13 (#Z84492) and the indicated nucleotide sequence numbers (SEQ ID NO: 17). Arrowheads indicated primers for SSCP analysis. Boxes represent cDNA with the open reading frames (black) and untranslated regions (white) for the 110 amino acid wild type and 82 amino acid aberrant splice form of FUS1. Note the sequence for FUS1 and FUS1-aberrant is the same for the first 80 amino acids. Three sets of primers were designed to cover the full FUS1 open reading frame for PCR-SSCP analysis. The primers used were S1: GTTATGGTAGTGCGGACTG (SEQ ID NO: 11) and AS1, GGTGGAACCATTGCCCTTAC (SEQ ID NO: 12); S2: GACCTGTGACATTTGCCGTG (SEQ ID NO: 13) and AS2, CAACAGATCCCATCTGGGTC (SEQ ID NO: 14); and S3 CCTGAGCTGACCCCTTACA (SEQ ID NO: 15) and AS3, TCTGTCTGCCACCTCCCAG (SEQ ID NO: 16).

Figure 25A:
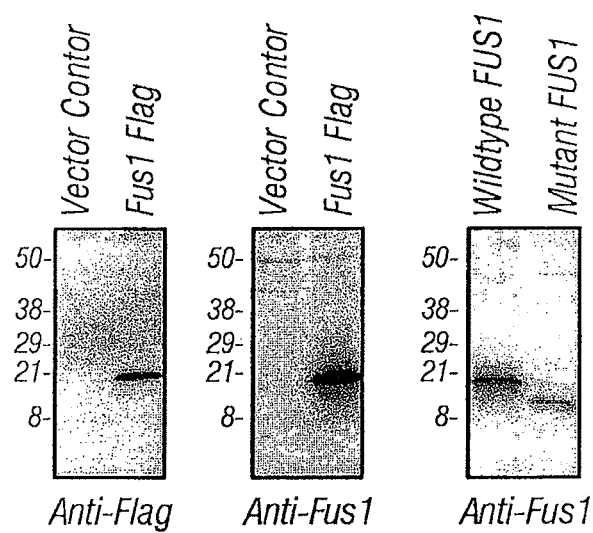
Figure 25B:
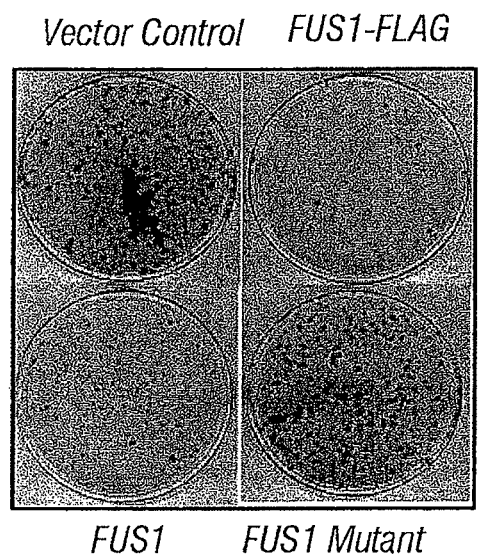
Figure 26A:
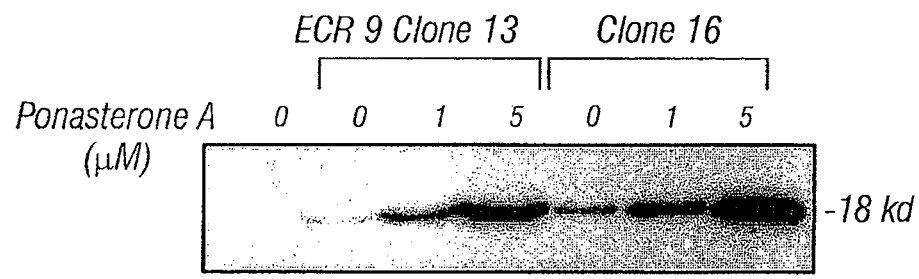
Figure 26B:
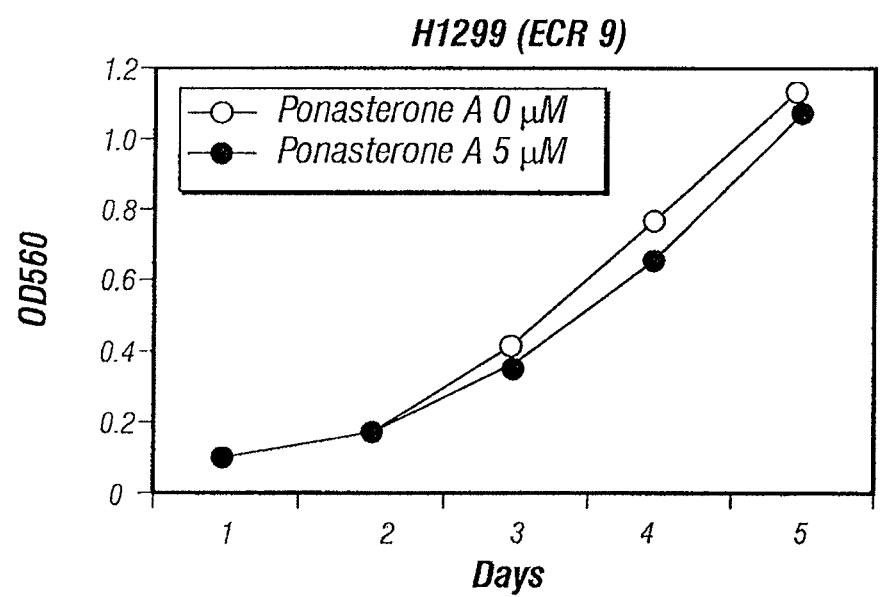
Figure 26C:
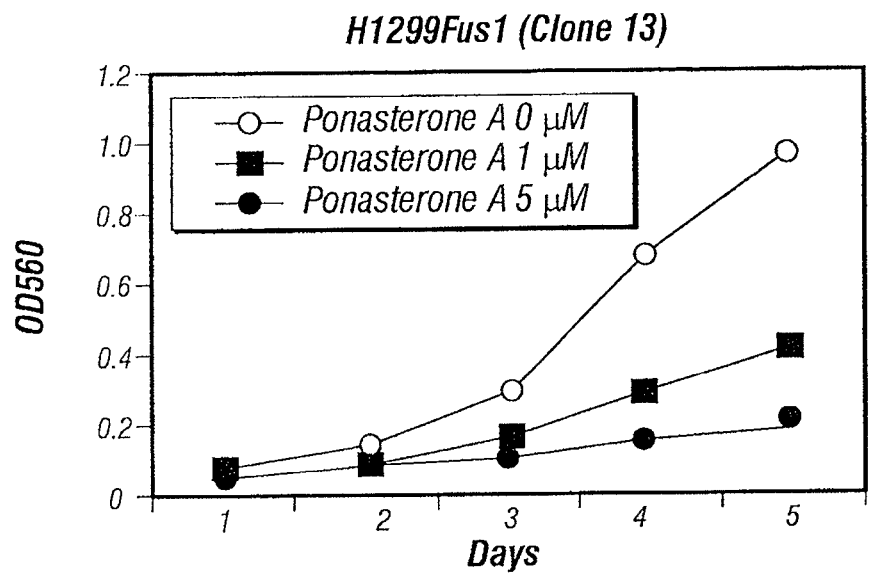
Figure 26D:
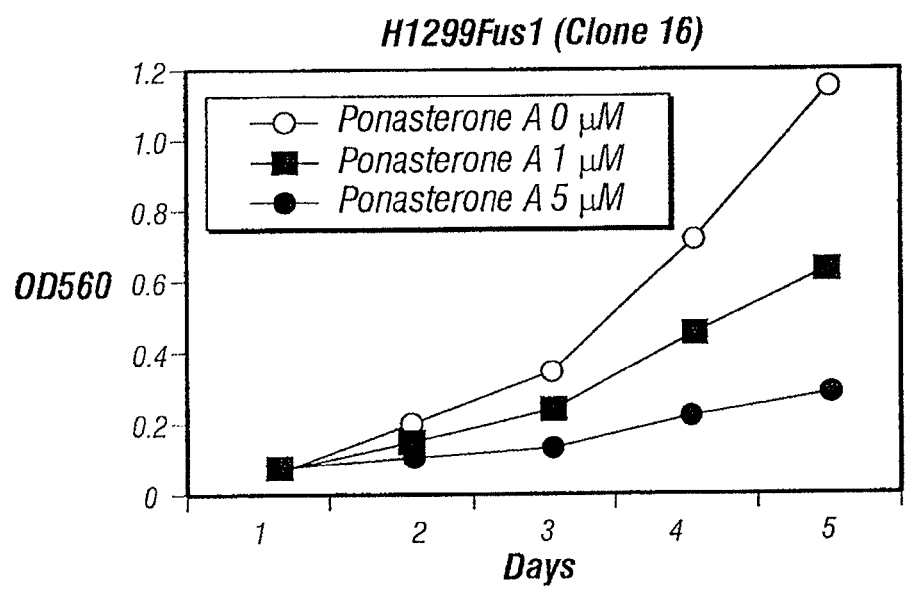

FIG. 25A-25B. (a.) Western blot analysis of endogenous and transient expression of FUS1 in lung cancer cells. Transfection was performed according to the manufacture's instruction using DMRIE C (Life Technologies, Inc., GIBCO BRL Gaithersburg, Md.). NSCLC H1299 ($2 \times 10^5$ cells) were plated in 3.5 cm dishes 24 hour before transfection and 2 μg of plasmid and 4 μl of DMRIE C were used for each transfection. All of the plasmids were resequenced after PCR construction and the sequences of the various FUS1 open reading frames were verified. Ten μl of lysate was made from $2 \times 10^4$ cells using sample buffer (100 mM Tris 2% SDS 10% β-mercaptoethanol 20% glycerol 0.03% PBP) and run in 12.5% SDS-PAGE gels followed by transfer to nitrocellulose membranes. After blocking with 5% dry milk and 0.2% Tween 20 in PBS, the membranes were incubated at room temperature for 1 h with rabbit polyclonal antibodies. Anti FUS1 antibodies (1:300 dilution of sera) were generated by immunizing rabbits (Strategic Biosolution Ramona, Calif.) with peptides corresponding to amino acid 1 to 15 of the human FUS1 protein sequence. Anti-FLAG antibody M2 was from Sigma (St. Louis, Mo.). The membranes were developed after incubation with presence of peroxidase-labeled anti-rabbit or anti-mouse IgG antibodies using Super Signal chemiluminescent substrate (Pierce Rockford, Ill.). The calculated molecular weight of FLAG-tagged FUS1 is 15 kd and the size of the band that was recognized by both antibodies is slightly higher than the calculated size. As expected the mutant FUS1 (predicted to be 82 amino acids) is slightly smaller than wild type FUS1 (110 amino acids). (b.) Results of colony formation assays in H1299 NSCLC cells. After transfection, the H1299 cells were trypsinized, replated and cultured in G418 (600 μg/ml) supplemented medium (RPMI 1640 5% fetal bovine serum) for 2 or 3 weeks and the number of G418 resistant colonies counted after staining with methylene blue in ethanol/PBS (50/50%). Note dramatic suppression of colony formation after transfection with FUS1 and FUS1-FLAG but much less suppression with the 82 amino acid aberrant FUS1 construct. The mean and standard deviations for an average of 2-4 plates for 2 or more experiments for H1299 were: vector control pcDNA3.1, 100±18% (100%=248 colonies), FUS1-FLAG 16±10%, FUS1 23±11%, FUS1 mutant 77±11%. Colony numbers of FUS1 and FUS1-FLAG transfected cells were significantly reduced (P<0.01, student's t test) compared with vector control. H322 cells had 40±34% colony formation with FUS1-FLAG transfection compared to 100% for vector control (P<0.05).

FIG. 26A-26D. (a.) Induction of FUS1 protein by Ecdysone expression vector (Invitrogen, Carlsbad, Calif.) under the control of the Ponasterone A in NCI-H1299 stable transfected clones. The inventors transfected the regulatable hormone receptor vector pVgRXR into H1299 and obtained 20 Zeocin (selection marker of pVgRXR) resistant clones. These stable pVgRXR transfectants were screened for β-gal activity following transfection with pIND-LacZ. From these clones the inventors selected clone ECR 9 as a parent cell line in which β-gal activity was specifically regulated by Ponasterone A in H1299 cells. The inventors made an expression vector which contained FUS1-FLAG (pIND sp1-FUS1-FLAG) and transfected this into ECR 9. Western analysis. Ten μg total cell lysate protein from each cell line and anti-FUS1 antibody were used for the analysis. The concentration (μM) of Ponasterone A used for induction is indicated above the blots. ECR9 is H1299 parent cell line transfected with the regulatory vector alone; clones 13 and 16 represent H1299 clones containing a regulatable FUS1 vector. The in vitro growth of (b.) NSCLC H1299ECR 9 (control), (c.) H1299FUS1Clone13 and (d.) H1299FUS1Clone16 was measured by the MTT assay. Cells ($10^4$) were plated in 1 ml of RPMI 1640 (Life Technologies Inc.) with 5% fetal bovine serum and cultured in the presence (1, 5 μM) or absence of Ponasterone A in a 24 well plates (added at day 0) and wells were harvested for MTT assays at the days indicated. MTT (Sigma) was added to the cultures (500 μg/ml), incubated at 37° C. for 2 hours, the intracellular formazan crystals solubilized with isopropanol containing 0.01 N HCl, and the absorbance of the solution at 560 nm was measured using a spectrophotometer. The OD 560 is directly proportioned to cell number in the range of 0-1.2. Data points represent an average of 3 wells with SD (contained within the symbols) of each data point ~5%. For cell cycle distribution analysis of the FUS1 inducible H1299 clones, cells ($2 \times 10^5$) of ERC 9, CL.13 and Cl. 16 were plated on 10 cm dishes and cultured in the presence (5 μM) or absence of Ponasterone A for 2 days. Cells were harvested, fixed in 50% ethanol/PBS, treated with 5 mg/ml RNase, stained with propidium iodide and analyzed for DNA content by FACSCaliber instrument (Becton Dickinson San Jose, Calif.). FACS analysis was performed in three independent experiments with similar results. Under FUS1 induced conditions the % of cells in G1 increases significantly (P<0.05) compared to controls.

SEQUENCE SUMMARY

SEQ ID NO: 1=Beta* (BLU) nucleotide sequence
SEQ ID NO: 2=Beta* (BLU) amino acid sequence

DETAILED DESCRIPTION OF THE INVENTION

Tumor suppressor genes (TSGs) play a major role in the pathogenesis of human lung cancer and other cancers. Lung cancer cells harbor mutations and deletions in multiple known dominant and recessive oncogenes[6,7]. Other TSGs that have been found to be altered in lung cancer are p53, p16, Rb, and FHIT-1[52]. Known TSGs such as Rb, p53, and others have been found at chromosome regions 3p, 5q, 6p, 8p, 9p, and 11p as well as other sites[6,8,9]. Cytogenetic and allelotyping studies of fresh lung tumors and tumor cells showed tumor-cell allele loss at multiple sites, suggesting the existence of one or more such TSGs[6-8,10]. These loci are important in understanding predisposition to lung cancer among smokers[52]. Loss of heterozygosity (LOH) is common in lung cancers, as in other solid tumors. Some of the chromosomal loci that experience a loss of heterozygosity in lung cancer are: 9p21-p22, 13q14, 17p13.1, 3p12-p14, 3p21, 3p25, 5q21, 11q12-q24, and 22q. Vulnerability to lung cancer may be due to genetic differences occurring at multiple loci. These genes may play a role in the metabolization of tobacco carcinogens. Cytogenetic changes and allele loss on the short arm of chromosome 3 (3p) have been shown to be most frequently involved in about 90% of small cell lung cancers (SCLCs) and >50% of non-small cell lung cancers (NSCLCs)[6,8,10,11]. In addition, similar 3p changes have been seen in several other cancers, such as renal[12,13], breast[14,15], head and neck[16], pancreatic[17], kidney[18], oral[19], and uterine cervical cancers[20,21].

Recently, human chromosome band 3p21.3 has been shown to undergo overlapping homozygous deletions in several SCLC and NSCLC lines. Candidates of TSGs have been located in this critical region in several human cancers, further defining a TSG region[6,10,24,27]. The evidence shows that genes in this 3p21 critical region are involved in regulation of the telomerase-mediated cellular immortality pathway in lung, renal, and breast cancer cells[28,29]. Cell hybrid and microcell chromosome 3 transfer studies have demonstrated the ability of human chromosome 3 genes to suppress malignancy in human lung, renal, and ovarian cancer cell lines[6,30]. It also has been shown that 3p deletion occurs more frequently in the lung tumor tissues of patients who smoke. In addition, elevated sensitivity to the carcinogen benzo[a]pyrene diol epoxide at 3p21.3 has been associated with an increased risk of lung cancer, suggesting that 3p21.3 can be a molecular target of carcinogens in lung cancer[31].

Figure 3:
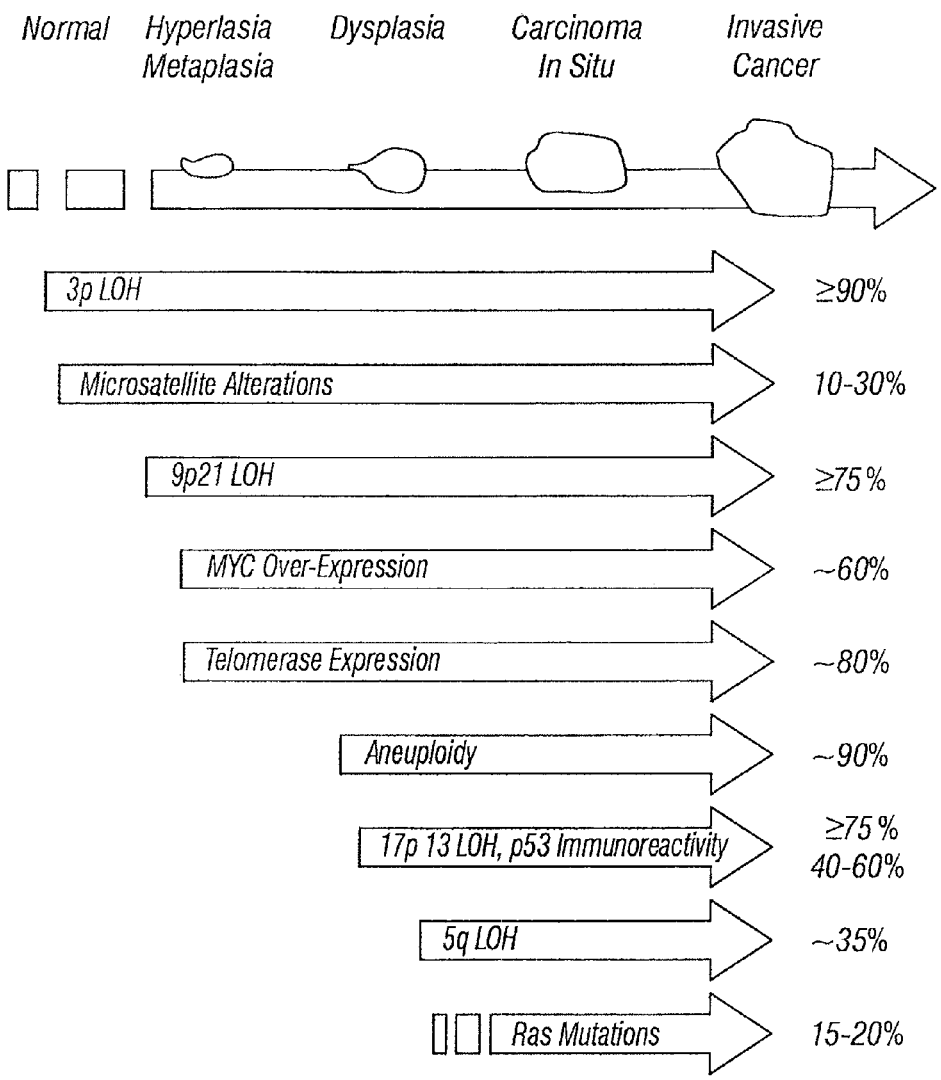
FIG. 3. Timing of genetic changes found in preneoplastic lesions of the respiratory epithelium associated with primary non-small cell lung cancers.
Figures 1, 4A:
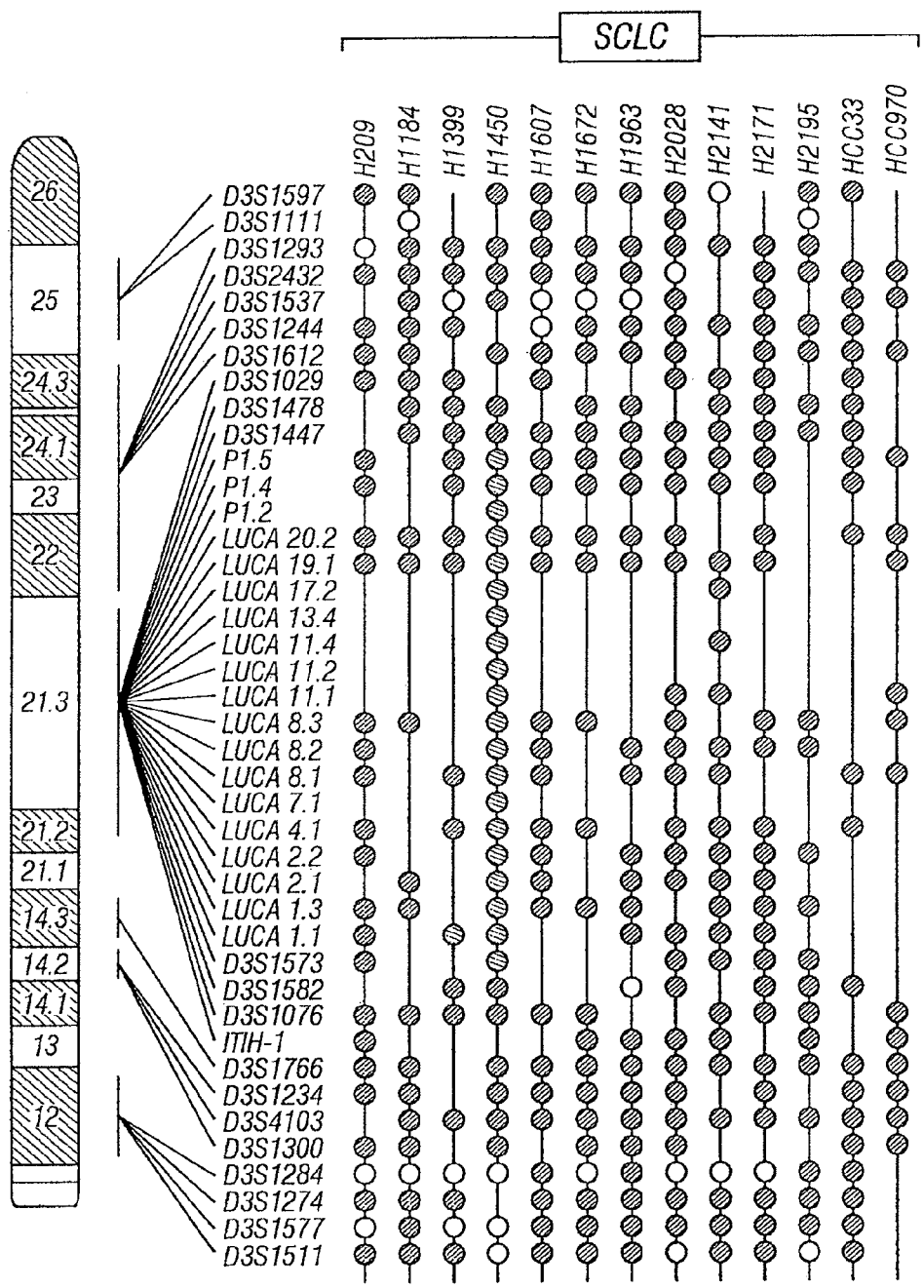
Figures 2, 4A:
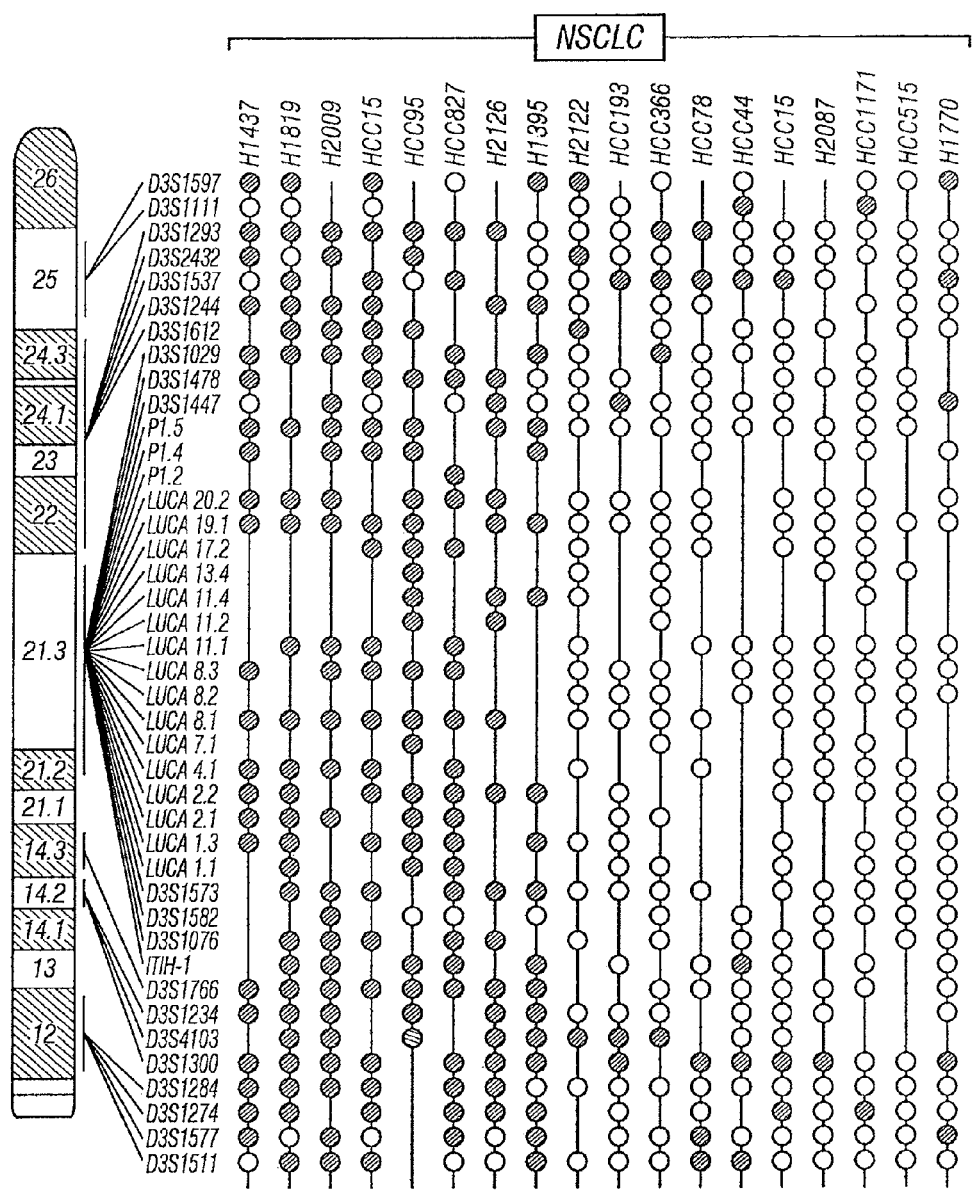
Figures 1, 4B:
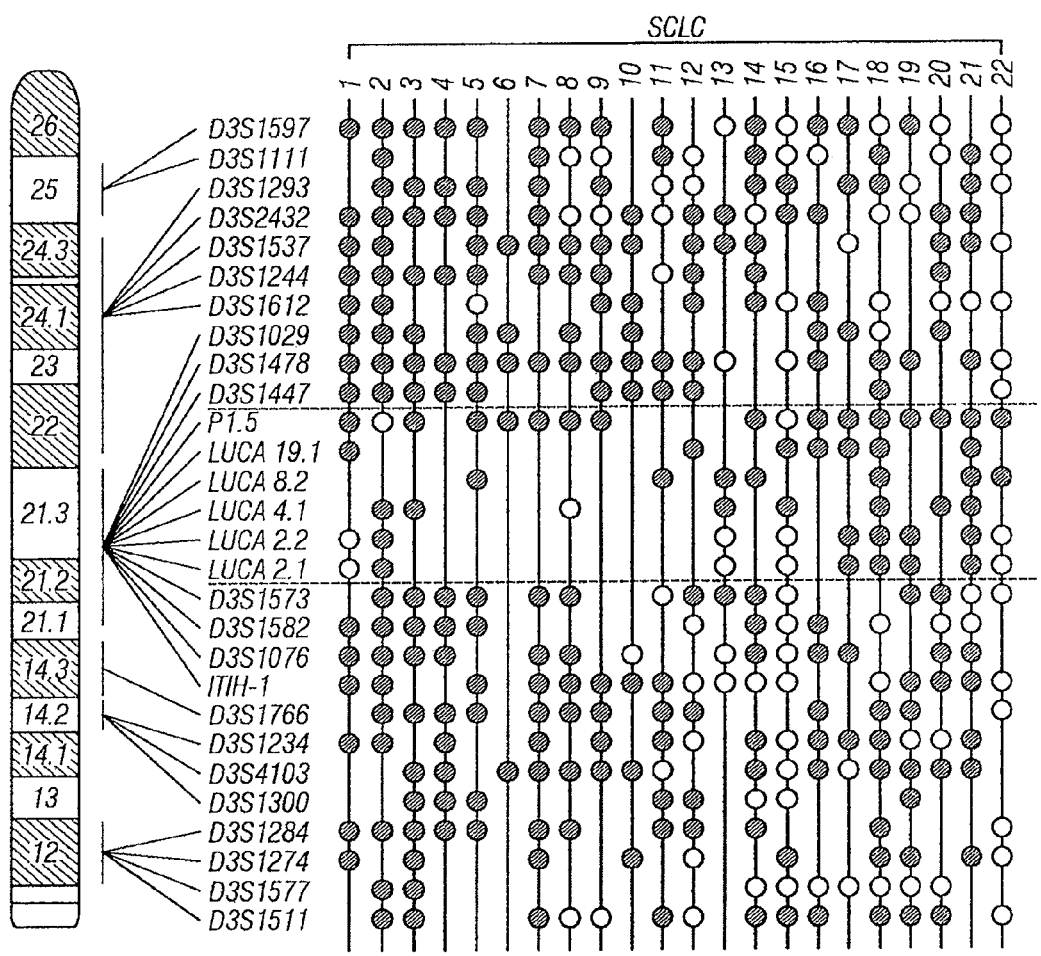
Figures 2, 4B:
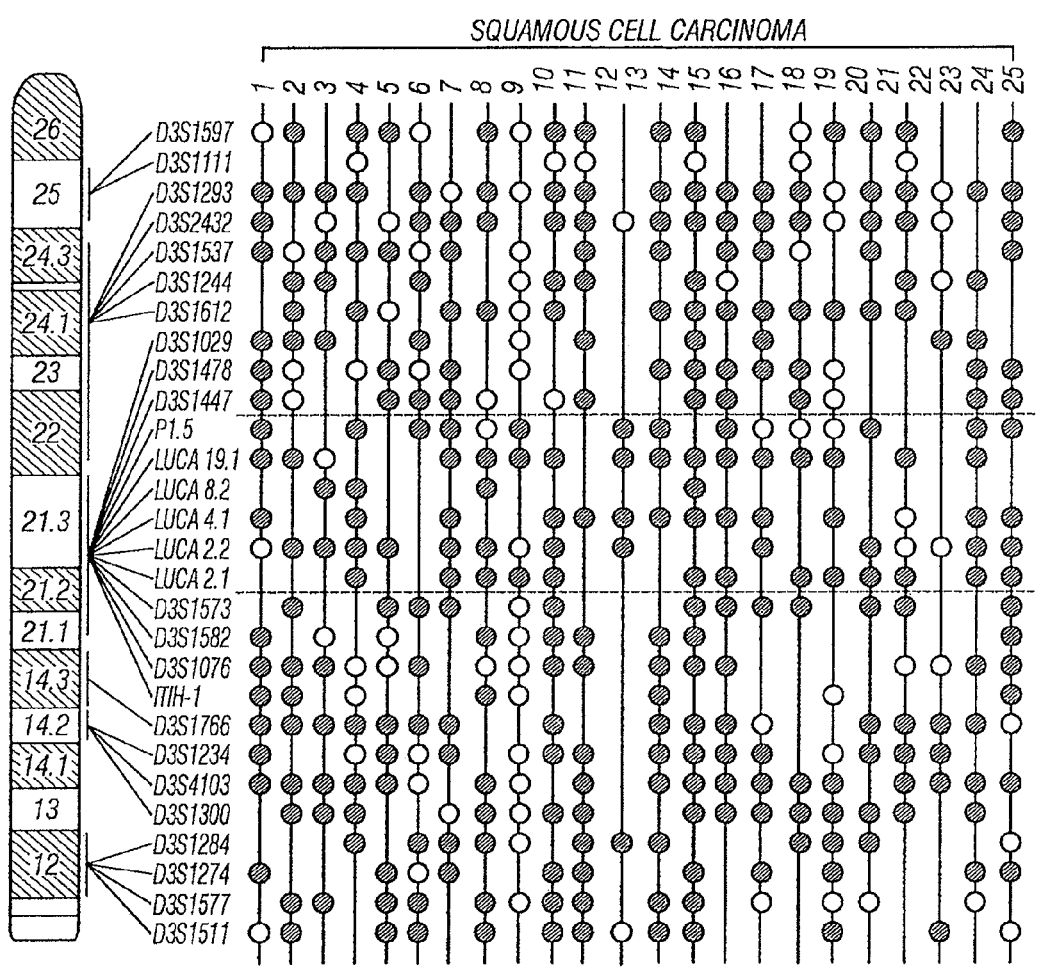
Figures 3, 4B:
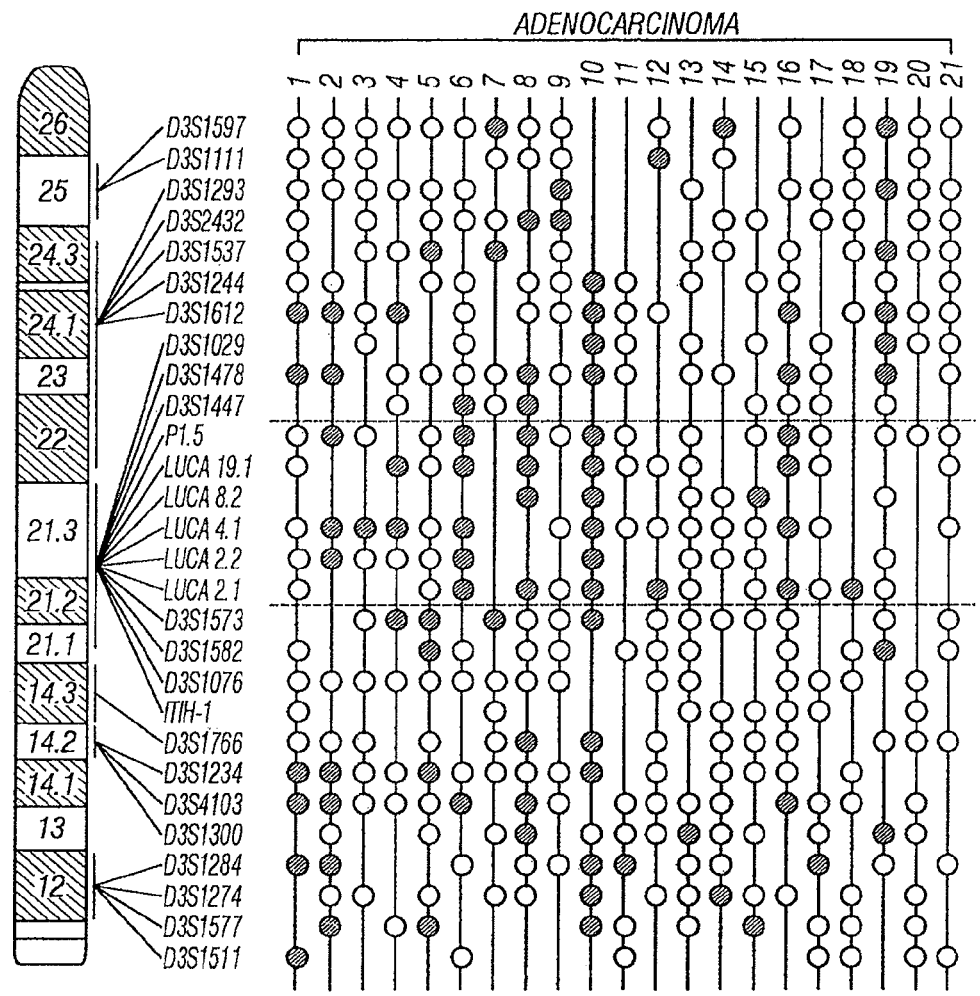

This invention identifies genetic loci involved in lung cancer. A group of TSGs (Fus1, 101F6, Gene21 (NPRL2), Gene26 (CACNA2D2), PL6, Luca1 (HYAL1), Luca2 (HYAL2), 123F2 (RASSF1), Beta* (BLU) and SEM A3), as defined by homozygous deletions in lung cancers, have been located and isolated at 3p21.3 in a 450-kb region[6,10,22-24]. Studies of lung cancer preneoplasia indicate that 3p21 allele loss is the earliest genetic abnormality in lung cancer detected so far. One or more 3p-recessive oncogenes function as "gatekeepers" in the molecular pathogenesis of many human cancers, including lung cancer, where it is likely to be involved in >50% of all cases[6,10,22-26] (FIG. 3).

Since (1) the 3p genes located at 3p21.3 in a 450 kb region are defined by homozygous deletions in lung cancers; (2) the 3p21 allele loss is one of the earliest genetic abnormalities detected in lung cancer and other tumors; (3) the loss of heterozygosity, the homozygous deletion, and the abnormality of these 3p genes are associated with the pathogenesis of many human cancers including lung cancer where it is likely to be involved in >50% of all cases; and (4) the multiple 3p genes function as tumor suppressor genes or the 3p21.3 region as a tumor suppressor region, the technologies and molecular tools developed based on the genetic/cytogenetic status and function of these 3p genes are extremely valuable for the early detection, diagnosis, and monitoring of prevention and therapeutic efforts for various human cancers.

I. Function of 3p Genes as Tumor Suppressor Gene Region

One of the criteria for defining the role of genes as tumor suppressor genes is to demonstrate that the tumor phenotype marked by inactivation of the genes can be rescued by the replacement of the wild-type alleles of these genes. If the frequent loss of heterozygosity (LOH), homozygous deletion, or, in some cases, abnormal transcripts and mutations of genes are the targets of carcinogens and the loss of function of genes leads to human cancers, then replacement of the abnormal genes with the wild-type genes would result in tumor suppression similar to that shown by the Rb or p53 tumor suppressor gene including inhibition of tumor cell growth in vitro, suppression of tumorigenicity and tumor growth, and inhibition of tumor cell invasion and metastasis in vivo[32-34].

The identification of the 3p genes as tumor suppressor genes was based on the cytogenetic and alleotyping studies of fresh tumors and tumor cell lines showing tumor cell allele loss at multiple sites and homozygous deletion in this region. Some of these 3p genes share varied degrees of homology in DNA and the predicted amino acid sequences to some known genes in the presently available data bases; however, the function of these 3p genes or the 3p21.3 region in pathogenesis and tumorigenesis of cancers is previously unknown. Cell hybrid and microcell chromosome 3 transfer studies demonstrated the ability of human chromosome 3 genes to suppress malignancy in human lung, renal, and ovarian cancer cell lines and mouse A9 fibrosarcoma cells, however, only one example involving introduction of a whole chromosome 3 into A549 human lung carcinoma cells has been reported[10,30,36-38].

In the present invention, it is the first time that the function of the individual 3p genes in suppression of tumor growth and tumor progression, induction of apoptosis, alteration of cell cycle kinetics, as well as repression of telomerase activity has been characterized by the liposome- and the recombinant adenoviral vector-mediated transfer of 3p genes in vitro and in vivo, and that the concept of function of 3p genes as a tumor suppressor region has been developed based on the tumor suppressor activities involved in multiple 3p genes in this critical 3p21.3 region. The finding of the 3p tumor suppressors permits new therapeutics to be developed for treating related cancers.

The adenoviral vector has been shown to be the most efficient gene delivery system in vitro and in vivo[4,5]. Recombinant adenovirus vectors have been widely used for gene transfer in basic research as well as for clinical applications[1-3]. However, in vitro manipulation of adenoviral DNA is very difficult due to the large size of the genome and limited unique and useful restriction sites, making the construction of recombinant adenoviral vectors relatively time consuming and labor intensive. Two conventional methods for the construction such recombinant adenoviruses are well documented: an in vitro ligation method[39] and an in vivo homologous recombination method[40]. The in vitro ligation method consists of a first step of subcloning the transgene into a plasmid vector to generate a segment containing the left end of the viral genome and a mammalian gene expression cassette, and then the recombinant vector is produced by in vitro ligation of the segment into the viral genome, followed by transfection of the reconstituted recombinant viral molecule into permissive 293 cells. Hiroyuki and Kay disclose an in vitro ligation method[45]. The other methods use two plasmids with overlaping fragments to generate the recombinant virus by homologous recombination in 293 cells. The major limitations for these methods are the generation of a background of nonrecombinant virus, low frequency of in vivo homologous recombination, and repeated screening of plaque to isolate pure recombinant vectors. There are several alternative procedures for construction of recombinant adenoviral vectors based on homologous recombination of the two plasmids cotransfected in 293 cells[40], the targeted modification of the adenoviral genome in an infectious yeast artificial chromosome (YAC) in yeast cells[41], the cosmid adenoviral vectors in cosmid packaging bacteria[42], and plasmids in recA+ bacteria strain[43,44]. These methods while more efficient, are more complex, require the use of an additional yeast hosts or nonconventional bacterial strain, face the low frequency of homologous recombination in these host and the instability of the recombinant adenoviral genome in plasmids hosted by the recA+ bacterial strain.

By comparison, the present Ad-RAP system is very simple, efficient, and rapid for the construction of recombinant adenoviral vector for gene therapy. This system requires a simple in vitro ligation using regular molecular biology reagents and commonly used bacterial strain. The resulting recombinant adenoviral genome containing plasmids can be easily screened and are stable. The subsquent transfection of the linearized recombinant adenovirus DNA mediated by liposome (DOTAP) into the permissive 293 cells is very efficient and a homogeneous population of recombinant adenovirus can be produced rapidly.

The recombinant adenoviral vector, Ad-3ps, can be used to deliver 3p genes in vitro and in vivo with a much higher efficiency than any other available gene delivery systems and technologies. Due to the high efficiency of transduction and high level expression of transgenes in various cell types mediated by adenoviral vectors, the Ad-3p vectors can be used as a effective tool to study the biological function and mechanisms of these tumor suppressor genes in vitro and in vivo. The Ad-3ps can be used to limit tumorigenicity, tumor suppression, and restriction of metastatic processes in various tumors such as lung, colon, breast, stomach, cervix, and head and neck, prostate, and pancreas by either intravenous or intratumoral injection of the Ad-3p vector or protamine-Ad-3p complexes.

In many cases, expression of some genes such as Bak, Bax, FasL are highly toxic to the host 293 cells, making construction and production of the recombinant adenovirus bearing such genes extremely difficult and some times impossible by any of the above methods and procedures. The present Ad-RAP-TetR-Off system can be used to successfully construct and produce such recombinant adenoviral vectors. The expression of the transgene in the adenoviral vector can be turned off by addition of tetracycline into the cell culture medium, and, consequently, the toxic effect of the gene on the host cells can be avoided and the recombinant adenovirus can be produced in the 293 cells as usual. Some other systems such as binary adenoviral vector systems[46] have been developed to successfully construct such recombinant adenovral vectors. However, the expression of a transgene in one viral vector depends on the expression of a trans-activator gene in another one, i.e., two adenoviral vectors are required for transgene expression in vitro and in vivo, which, in turn, limited the application of such a system in vivo. By comparison, in the Ad-TetR-Off vector system, the trans-activator TetR-Off gene and the TetR-Off response element (TRE) co-exist in the same adenoviral vector, and, therefore, expression of transgene can be turned on or off in one vector in the absence or presence of the tetracycline inducer. Furthermore, since the transgene is under the control of the TRE regulatory promoter, the level of expression of the transgene can be efficiently regulated by administration of tetracycline in vitro and in vivo. Together, these novel features of the Ad-RAP-Tet-Off system make it a useful new tool for rapid and successful construction and production of a recombinant adenoviral vector carrying cytotoxic genes.

Introduction of individual wild-type 3p21.3 genes by liposome- and adenovirus-mediated transient transfection into lung cancer cell lines containing either heterozygous or homozygous deletion of the 3p region inhibited tumor cell growth, induced apoptosis, and altered cell cycle kinetics, suppressed tumor growth and tumor progression in nude mice. Varied levels of inhibition of cell growth, induction of apoptosis, and alteration of cell cycle kinetics were observed in Ad-Fus1, Ad101F6, and Ad-Gene 21-transduced human lung cancer cells H1299, A549, and H460, which are either lacking in 3p genes or have abnormal ones. However, no significant inhibitory effects on cell growth were observed in Ad-Fus1, Ad-101F6, and Ad-Gene 21-transduced normal HBEC and H358 cells, which contain wild type 3p genes. Therefore, the observed cell growth inhibition was not due to the general cytotoxicity of these genes. The overexpression of 3p genes in these Ad-3p tranfectants was verified by a quantitative Real-Time RT-PCR. Tumor growth was significantly suppressed by overexpression of 101F6, Fus1, and Gene 21 via intratumoral injection of Ad-101F6, Ad-Fus1, and Ad-Gene 21 vectors in H1299 and A549 xenografts in nude mice. Furthermore, the lung metastatic tumor growth was also significantly inhibited by systematic injection of protamine-complexed Ad-101F6, Ad-Fus1, and Ad-Gene 21 in nude mice bearing the experimental A549 metastasis. Together, these results show that multiple 3p genes function as tumor suppressor genes or as a tumor suppressor region in vitro and in vivo, and that these newly identified and characterized 3p tumor suppressor genes or this 3p tumor suppressor region can be used for cancer gene therapy, using molecular tools such as the liposome-3p complexes, recombinant adenoviral vectors containing 3p genes, and the local or systematic gene delivery systems developed in this invention. The identification and functional characterization of the wild-type 3p21.3 genes and their mutated forms in lung cancer and other cancers provides a crucial step in the development of therapy for lung cancer and other tumors.

A. Background of 3p21.3

A group of TSGs, as defined by homozygous deletions in lung cancers, have been located and isolated at 3p21.3 in a 450-kb region[6,10,22-24]. Studies of lung cancer preneoplasia indicate that 3p21 allele loss is the earliest genetic abnormality in lung cancer detected so far, occurring in hyperplastic lesions. One or more 3p-recessive oncogenes function as "gatekeepers" in the molecular pathogenesis of many human cancers, including lung cancer, where it is likely to be involved in >50% of all cases[6,10,22-26].

Recently, human chromosome band 3p21.3 has been shown to undergo overlapping homozygous deletions in several SCLC and NSCLC lines. Candidates of TSGs have been located in this critical region in several human cancers, further defining a TSG region[6,10,24,27]. Genes in the 3p21 critical region are involved in regulation of the telomerase-mediated cellular immortality pathway in lung, renal, and breast cancer cells[28,29]. It has also been shown that 3p deletion occurs more frequently in the lung tumor tissues of patients who smoke. In addition, elevated sensitivity to the carcinogen benzo[a]pyrene diol epoxide at 3p21.3 has been associated with an increased risk of lung cancer, suggesting that 3p21.3 can be a molecular target of carcinogens in lung cancer[31].

B. 3p21.3 Proteins

In addition to the entire Fus1, 101F6, Gene 21, Gene 26, Beta*, Luca1, Luca2, PL6, 123F2, and SEM A3 molecules, the present invention also relates to fragments of the polypeptides that may or may not retain the tumor suppressing activity. The entire length of each protein is Fus1=161, 101F6=222, Gene 21=203, Gene 26=1205, Beta*=440, Luca1=435, Luca2=473, PL6=351, 123F2=431, and SEM A3=749 amino acids. Fragments, including the N-terminus of the molecule may be generated by genetic engineering of translation stop sites within the coding region (discussed below). Alternatively, treatment of the Fus1, 101F6, Gene 21, Gene 26, Beta*, Luca1, Luca2, PL6, 123F2, and SEM A3 molecules with proteolytic enzymes, known as proteases, can produce a variety of N-terminal, C-terminal and internal fragments. Examples of fragments may include contiguous residues of the Beta* sequence of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

1. Purification of 3p21.3 Proteins

It may be desirable to purify Fus1, 101F6, Gene 21, Gene 26, Beta*, Luca1, Luca2, PL6, 123F2, and SEM A3 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; sodium dodecyl sulfate/polyacrylamide gel electrophoresis (SDS/PAGE); isoelectric focusing. A particularly efficient method of purifying peptides is fast protein liquid chromatography (FPLC) or even HPLC.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample can be low because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. It should be possible to elute the substance without destroying the sample or the ligand. One of the most common forms of affinity chromatography is immunoaffinity chromatography. The generation of antibodies that would be suitable for use in accord with the present invention is discussed below.

The present invention also describes smaller Fus1, 101F6, Gene 21, Gene 26, Beta*, Luca1, Luca2, PL6, 123F2, and SEM A3-related peptides for use in various embodiments of the present invention. Because of their relatively small size, the peptides of the invention also can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

The present invention also provides for the use of Fus1, 101F6, Gene 21, Gene 26, Beta*, Luca1, Luca2, PL6, 123F2, and SEM A3 proteins or peptides as antigens for the immunization of animals relating to the production of antibodies. A biospecific or multivalent composition or vaccine is produced. It is envisioned that the methods used in the preparation of these compositions will be familiar to those of skill in the art and should be suitable for administration to animals, i.e., pharmaceutically acceptable.

2. Variants of Fus1, 101F6, Gene 21, Gene 26, Beta*, Luca1, Luca2, PL6, 123F2, and SEM A3

Amino acid sequence variants of these polypeptides can be substitutional, insertional or deletion variants. Deletion variants lack one or more residues of the native protein that are not essential for function or immunogenic activity. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions are called fusion proteins.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutathine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

Amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine.

C. Nucleic Acids

Figure 5:
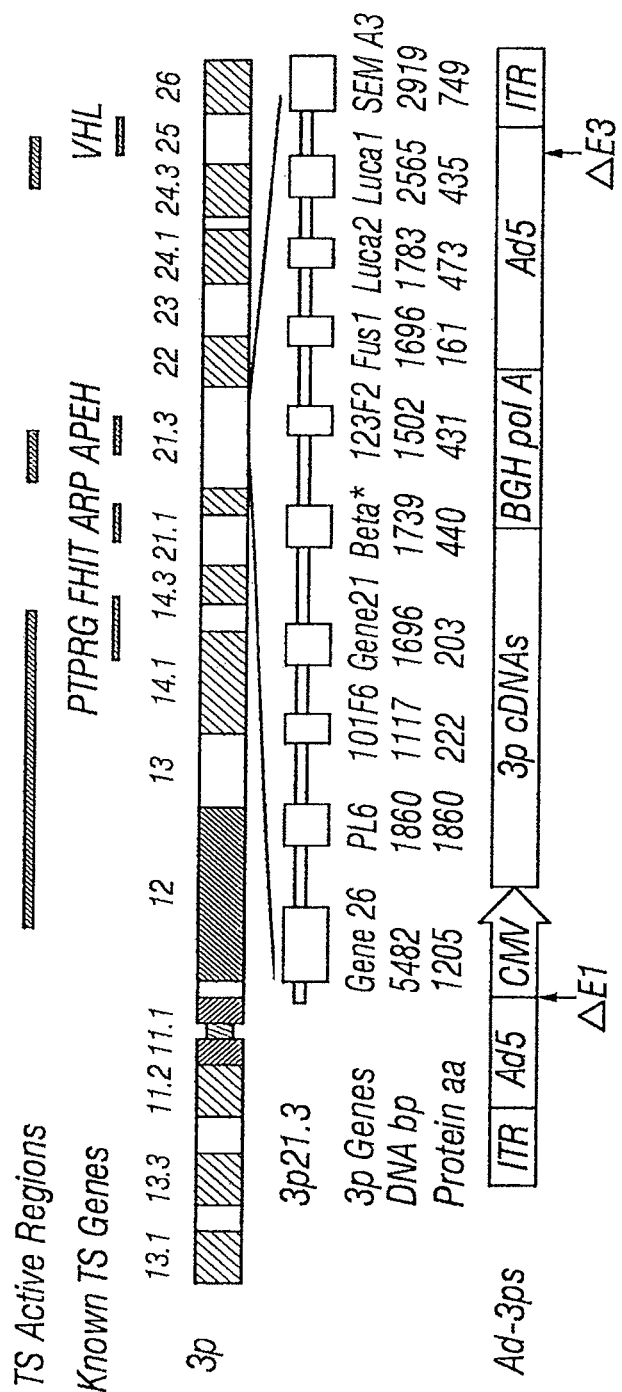
FIG. 5. Scheme of the location of the 3p21 tumor suppressor region in human chromosome 3p and the structure of recombinant adenoviral vectors of 3p genes. The sizes of the individual 3p genes and their corresponding amino acid residues, and the active tumor suppressor (TS) regions and known TSGs in the 3p are also indicated.
Figure 6A:
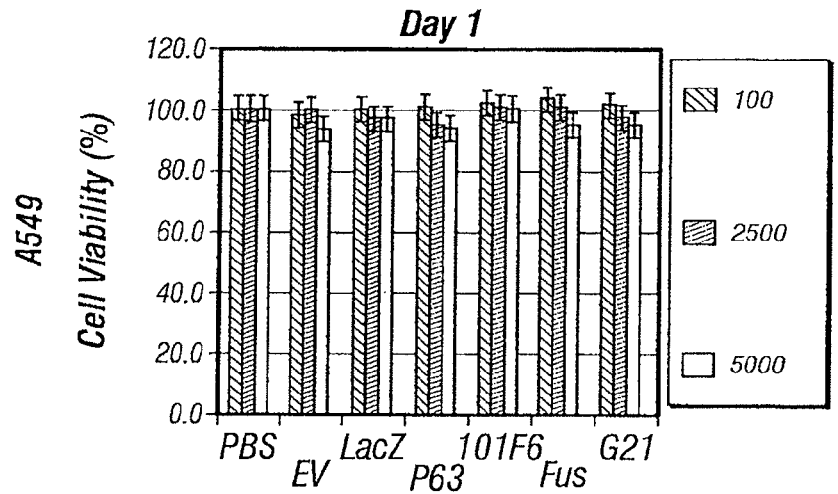
FIG. 6A-6O. Effects of overexpression of 3p genes on tumor cell growth in Ad-3p-transduced lung cancer cells and normal human bronchial epithelial cells. MOIs were expressed as viral particles/cell (vp/c).
Figure 6B:
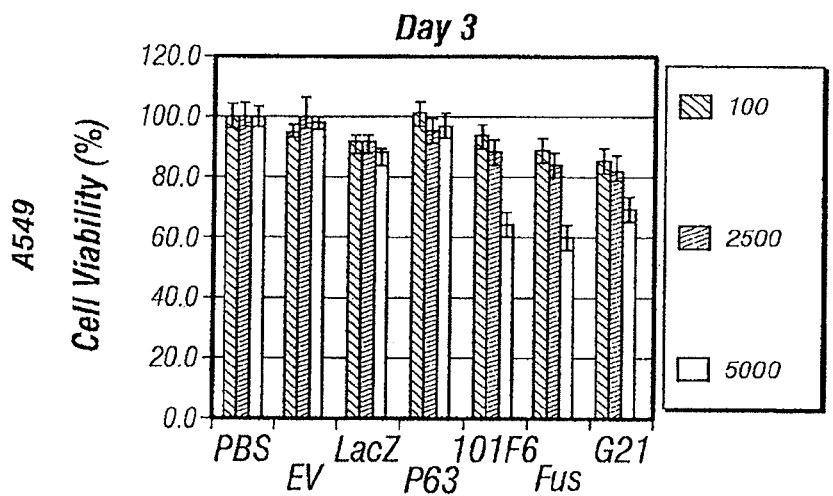
Figure 6C:
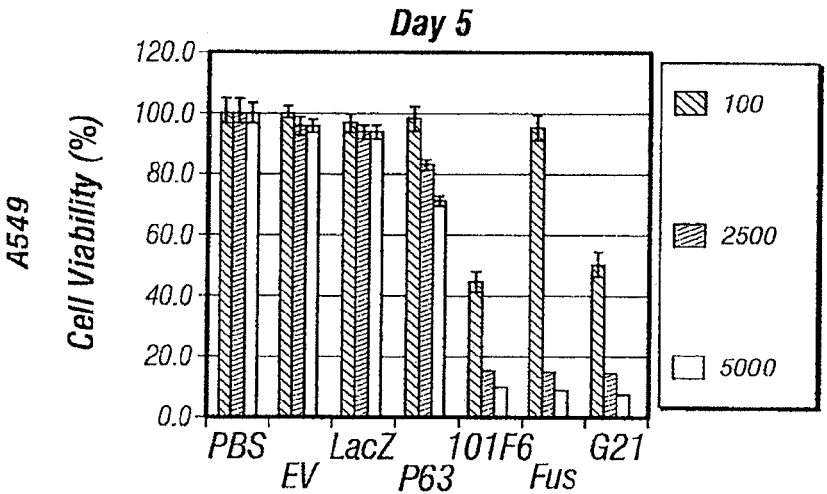
Figure 6D:
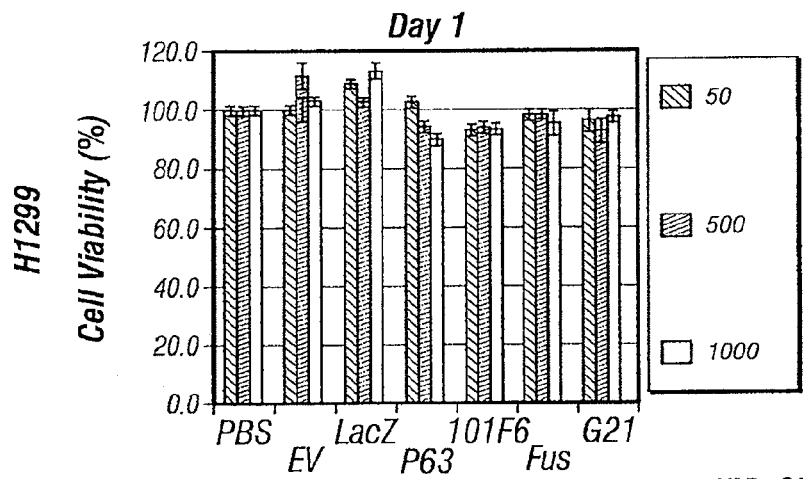
Figure 6E:
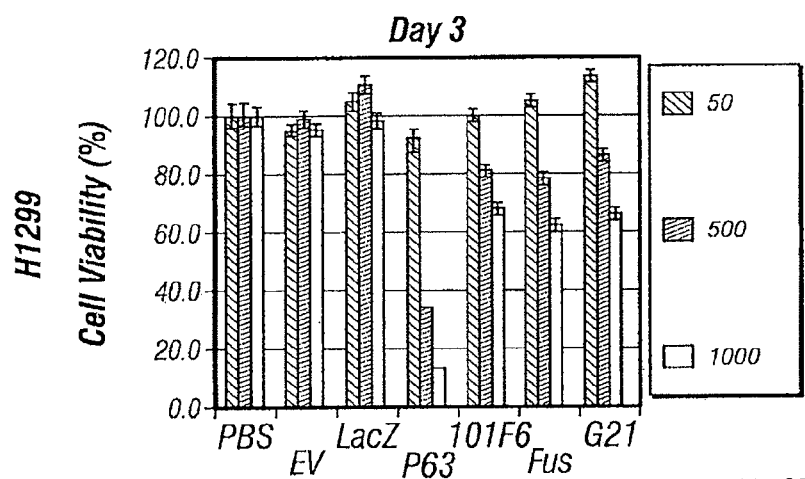
Figure 6F:
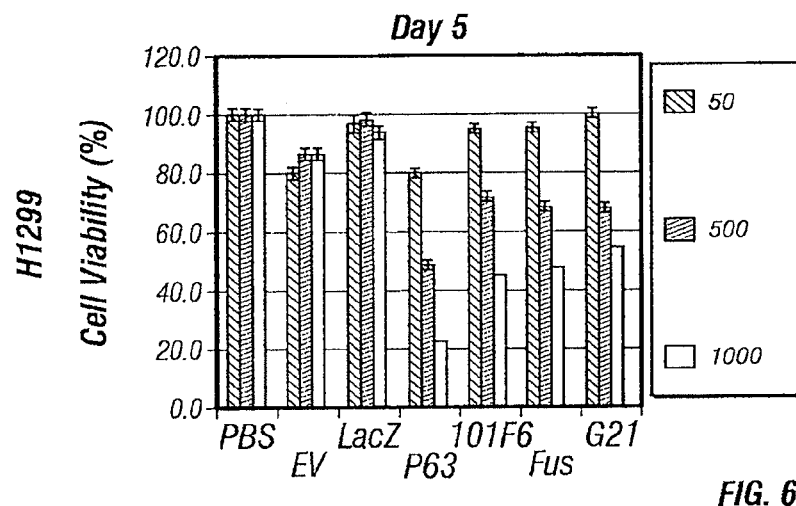
Figure 6G:
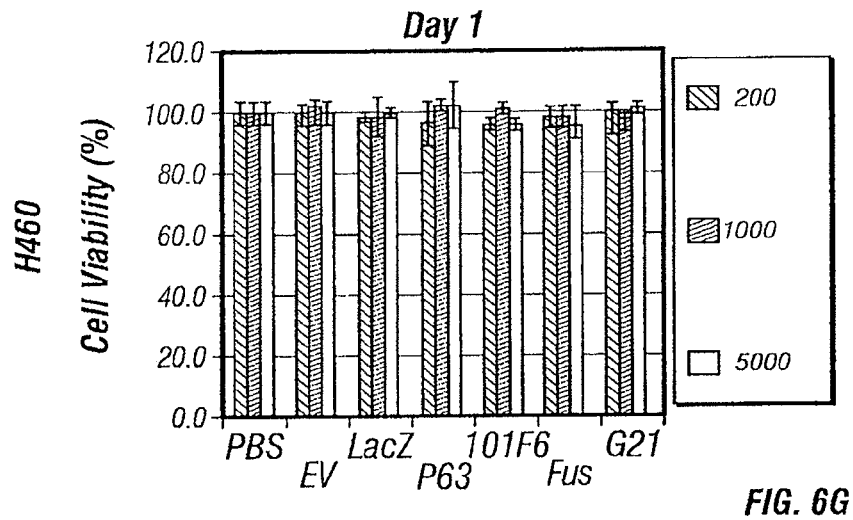
Figure 6H:
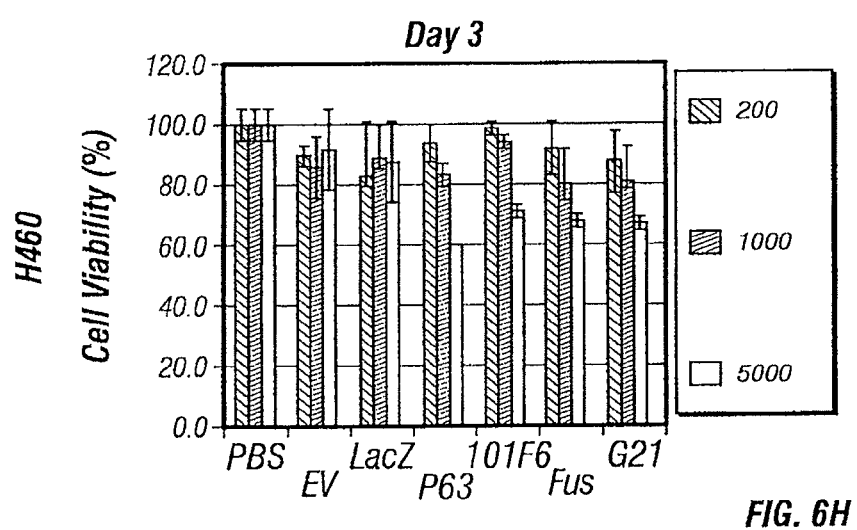
Figure 6I:
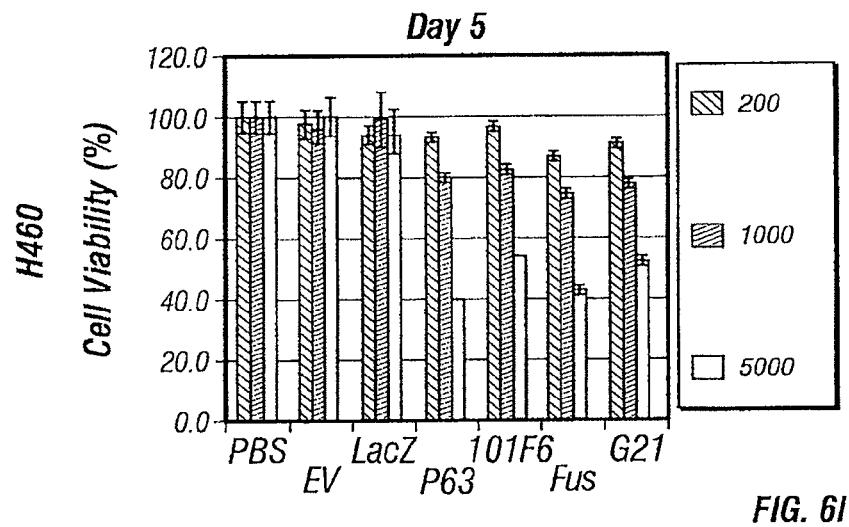
Figure 6J:
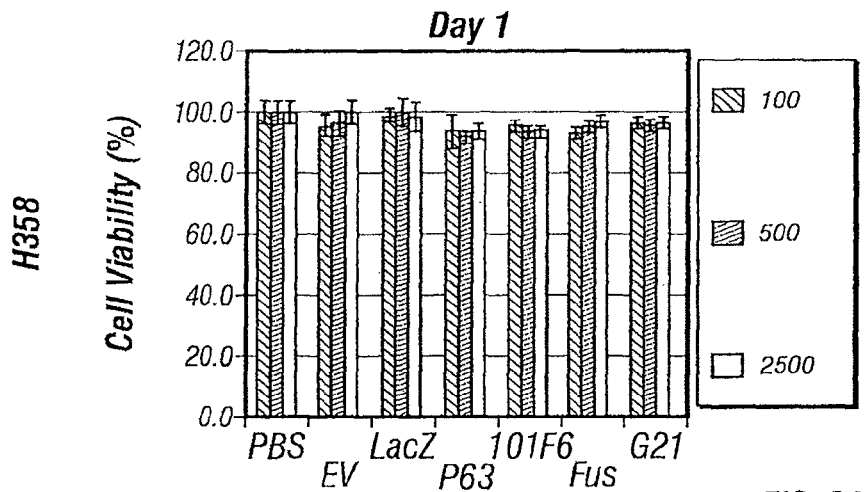
Figure 6K:
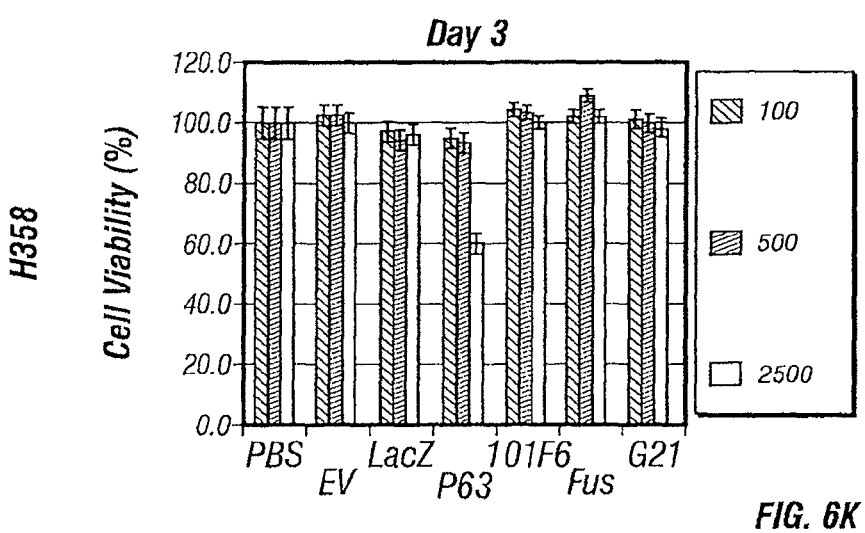
Figure 6L:
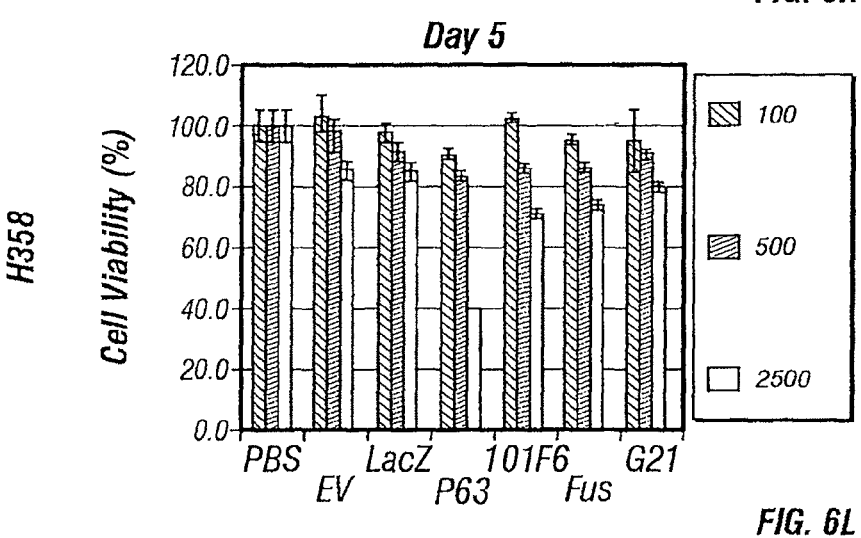
Figure 6M:
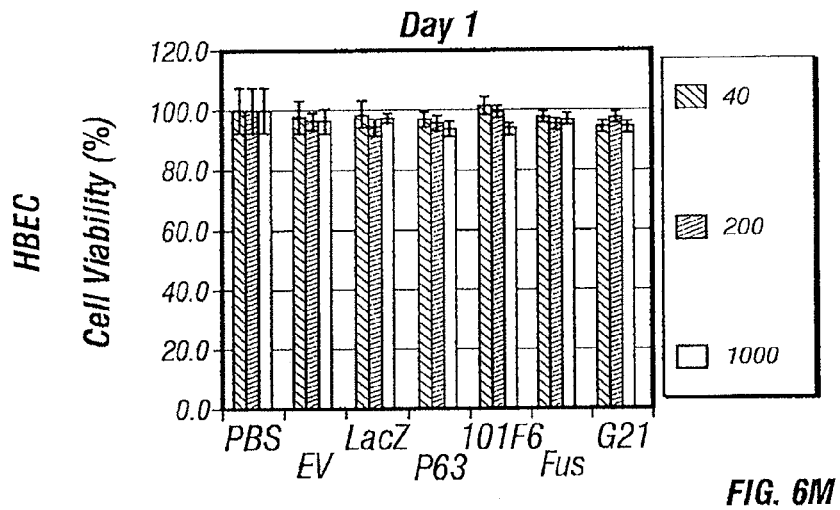
Figure 6N:
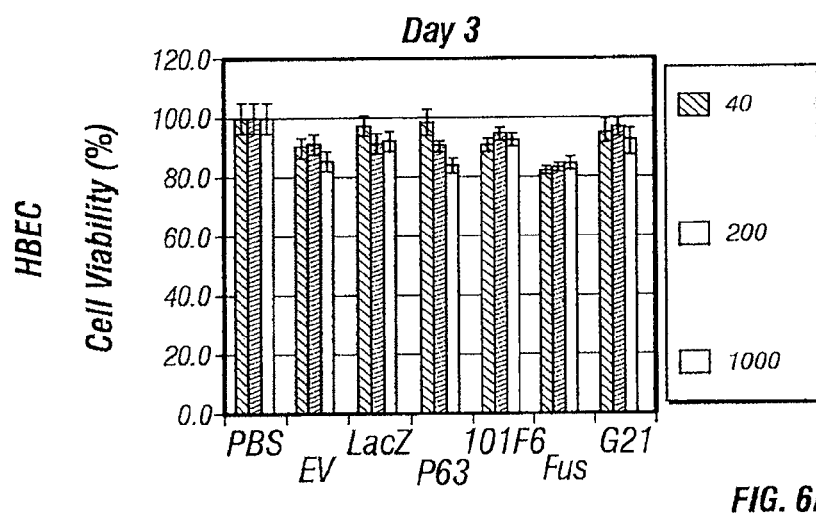
Figure 6O:
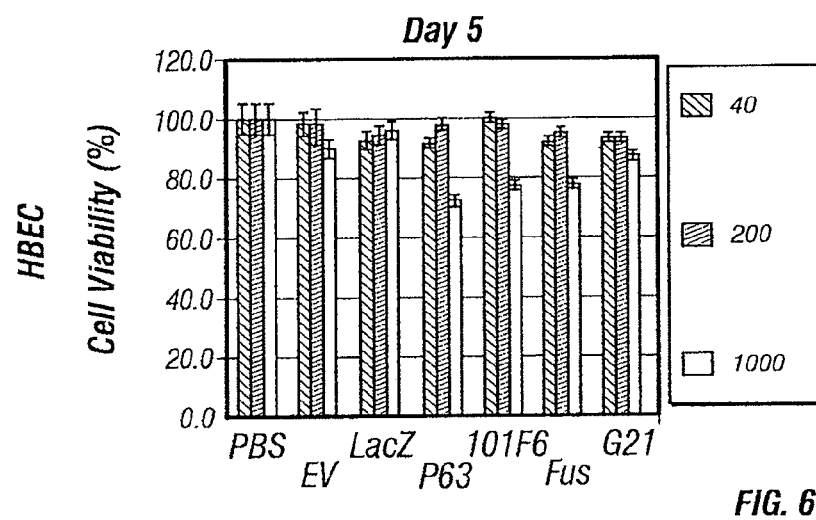
Figure 7A:
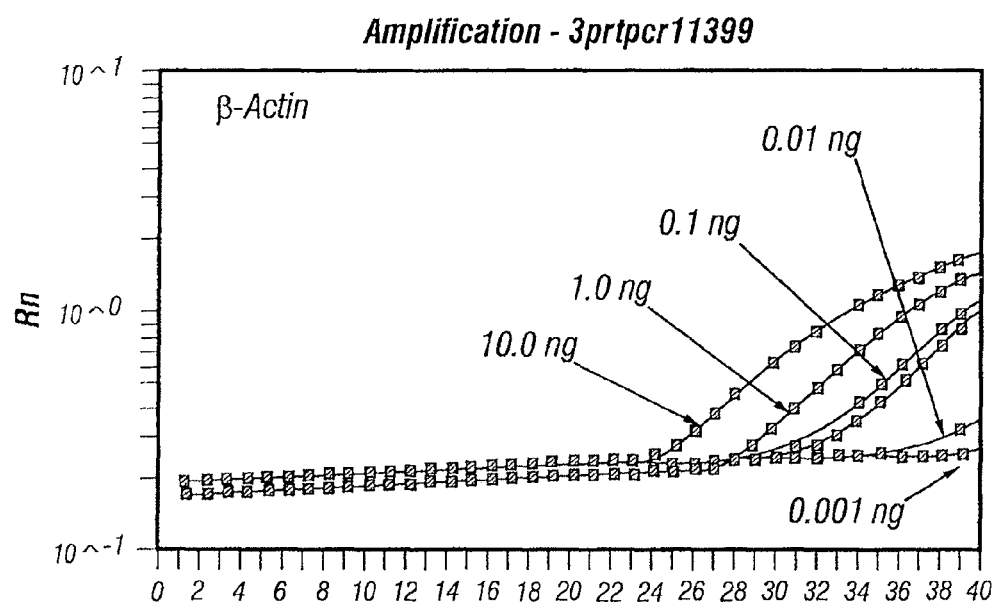
FIG. 7A-7D. Quantification of adenovirus-mediated 3p gene expression in H1299 cells by Real Time RT-PCR. The MOIs are expressed as viral particles/cell (vp/c).
Figure 7B:
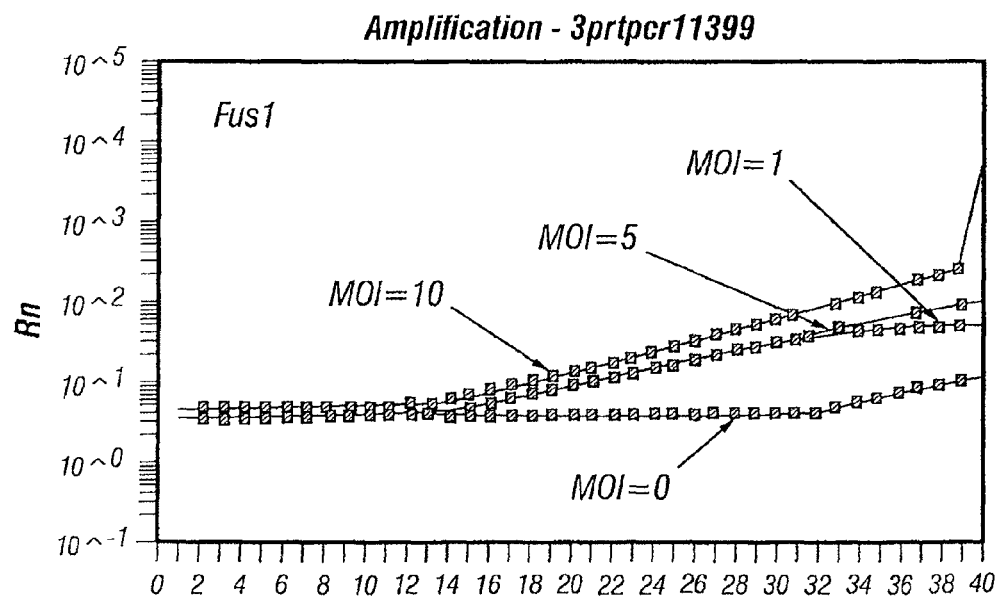
Figure 7C:
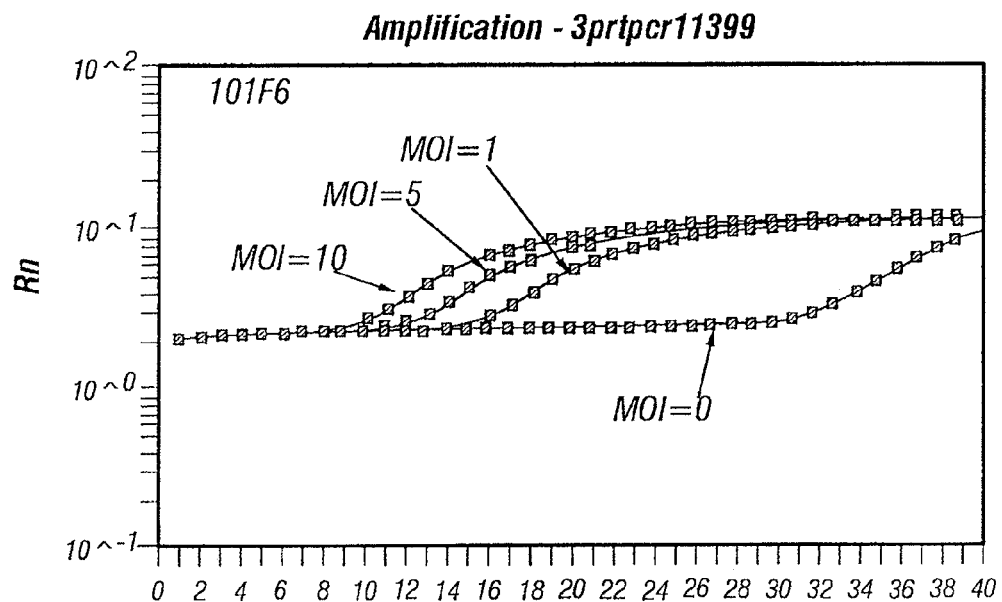
Figure 7D:
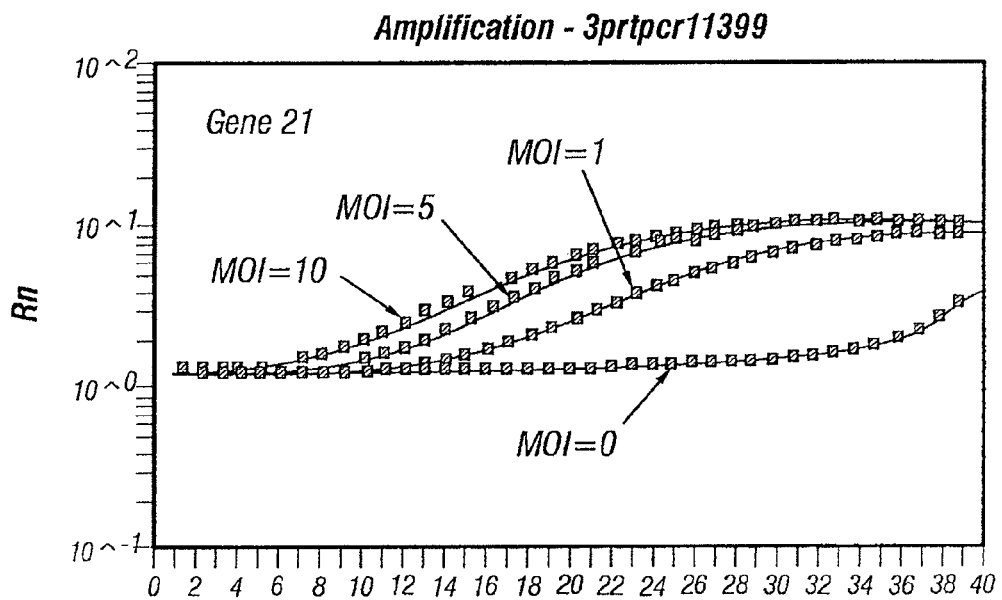
Figure 8A:
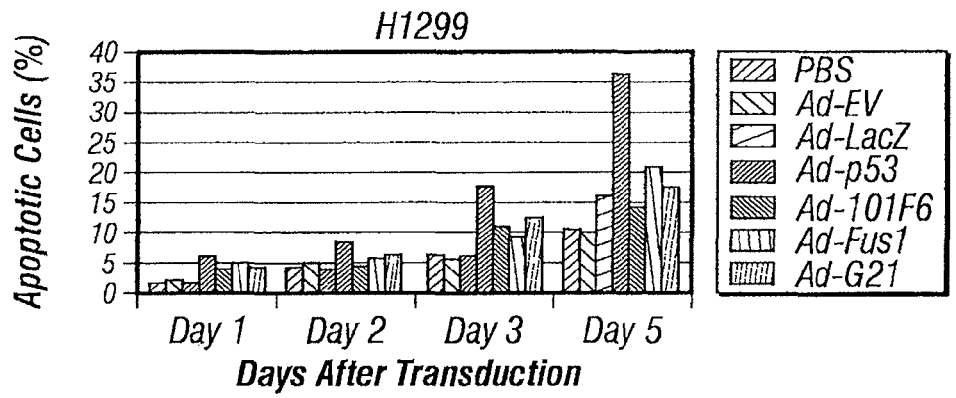
FIG. 8A-8E. Induction of apoptosis by overexpression of 3p genes in Ad-3p-transduced lung cancer cells and normal HBEC. Apoptosis was analyzed by FACS with TUNEL reaction.
Figure 8B:
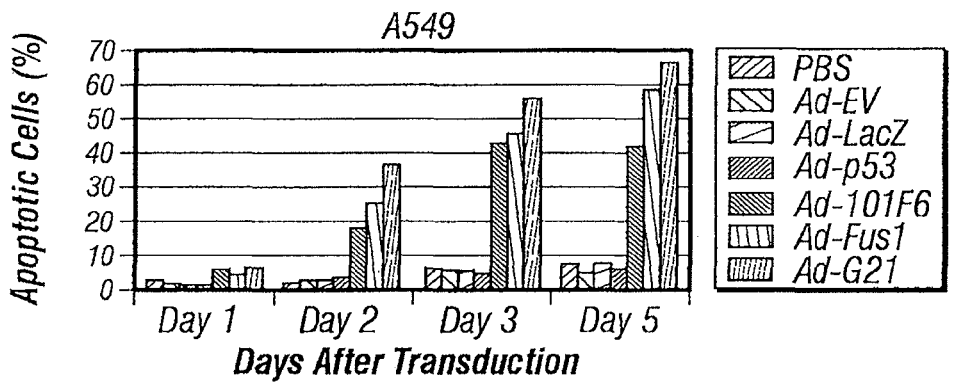
Figure 8C:
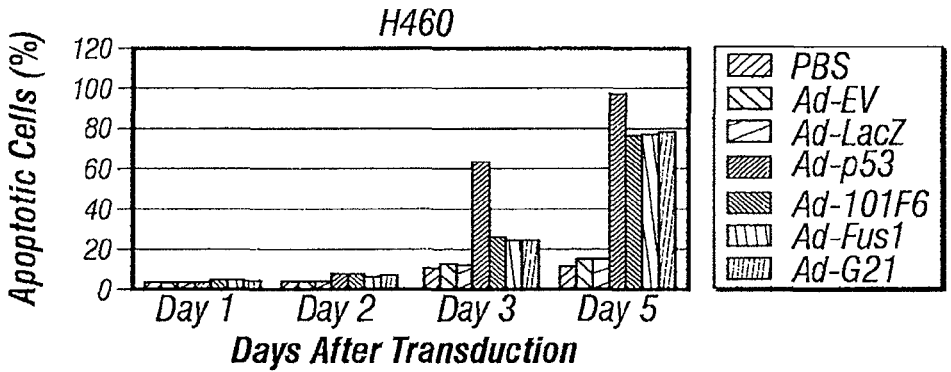
Figure 8D:
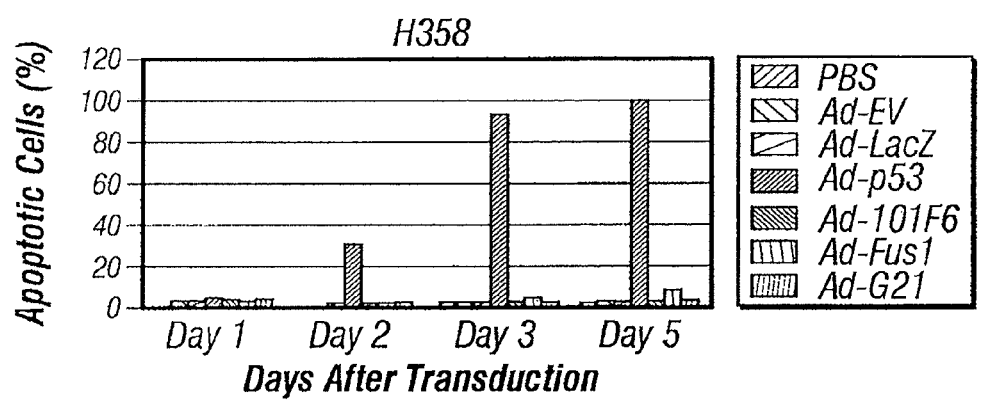
Figure 8E:
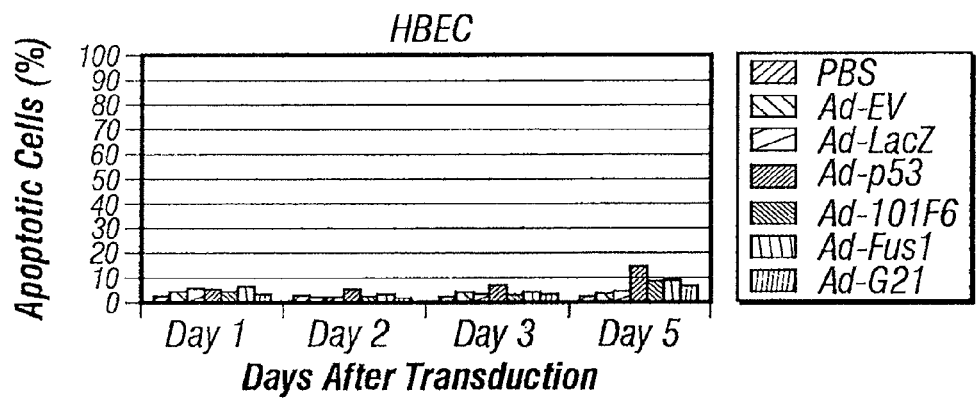

Fus1, 101F6, Gene 21, Gene 26, Beta*, Luca1, Luca2, PL6, 123F2, and SEM A3 are found at a chromosomal position of 3p21.3 in a 450 kb critical region. They are found in the following order at 3p21.3: Gene 26, PL6, 101F6, Gene 21, Beta*, 123F2, Fus1, Luca2, Luca1, and SEM A3. The length of each is Fus1=1696, 101F6=1117, Gene 21=1696, Gene 26=5482, Beta*=1746, Luca1=2565, Luca2=1783, PL6=1860, 123F2=1502, and SEM A3=2919 nucleic acids (FIG. 5).

In addition, it should be clear that the present invention is not limited to the specific nucleic acids disclosed herein. As discussed below, "Fus1, 101F6, Gene 21, Gene 26, Beta*, Luca1, Luca2, PL6, 123F2, or SEM A3 genes" may contain a variety of different bases and yet still produce a corresponding polypeptide that is functionally indistinguishable, and in some cases structurally, genes disclosed herein.

Nucleic acids according to the present invention may encode an entire Fus1, 101F6, Gene 21, Gene 26, Beta*, Luca1, Luca2, PL6, 123F2, and SEM A3 genes, a domain of Fus1, 101F6, Gene 21, Gene 26, Beta*, Luca1, Luca2, PL6, 123F2, and SEM A3, or any other fragment of the Fus1, 101F6, Gene 21, Gene 26, Beta*, Luca1, Luca2, PL6, 123F2, and SEM A3 sequences set forth herein. The nucleic acid may be derived from genomic DNA, i.e., cloned directly from the genome of a particular organism. In other embodiments, however, the nucleic acid would comprise complementary DNA (cDNA).

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given Fus1, 101F6, Gene 21, Gene 26, Beta*, Luca1, Luca2, PL6, 123F2, or SEM A3 from a given species may be represented by natural variants that have slightly different nucleic acid sequences but, nonetheless, encode the same protein (Table 1).

As used in this application, the term "polynucleotide having the nucleic acid sequence of SEQ ID NO: 1" refers to a nucleic acid molecule that has been isolated free of total cellular nucleic acid. A functionally equivalent codon is a codon that encodes the same amino acid, such as the six codons for arginine or serine (Table 1), and also refers to codons that encode biologically equivalent amino acids.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |

TABLE 1-continued

| Amino Acids | | | Codons |
|---|---|---|---|
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The DNA segments of the present invention include those encoding biologically functional equivalent Fus1, 101F6, Gene 21, Gene 26, Beta*, Luca1, Luca2, PL6, 123F2, and SEM A3 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

D. Hybridization

Naturally, the present invention also encompasses DNA segments that are complementary, or essentially complementary, to the sequences encoding Fus1, 101F6, Gene 21, Gene 26, Beta*, Luca1, Luca2, PL6, 123F2 and SEM A3. Nucleic acid sequences that are "complementary" are those that are capable of base-pairing according to the standard Watson-Crick complementary rules. As used herein, the term "complementary" means nucleic acid sequences that are substantially complementary, as may be assessed by the same nucleotide comparison set forth above, or as defined as being capable of hybridizing to the aforementioned nucleic acid segment under relatively stringent conditions such as those described herein. Such sequences may encode the entire Fus1, 101F6, Gene 21, Gene 26, Beta*, Luca1, Luca2, PL6, 123F2, and SEM A3 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, or 1000 bases and longer are contemplated as well. Such oligonucleotides will find use, for example, as probes in Southern and Northern blots, in situ tissue hybridization and as primers in amplification reactions.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM MgCl2, 10 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C. Formamide and SDS also may be used to alter the hybridization conditions.

E. Printers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In other embodiments, the probes or primers are labeled with radioactive species ($^{32}P$, $^{14}C$, $^{35}S$, $^{3}H$, or other label), with a fluorophore (rhodamine, fluorescein) or a chemilluminescent (luciferase).

One method of using probes and primers of the present invention is in the search for genes related to Fus1, 101F6, Gene 21, Gene 26, Beta*, Luca1, Luca2, PL6, 123F2, and SEM A3 or, more particularly, orthologs of Fus1, 101F6, Gene 21, Gene 26, Beta*, Luca1, Luca2, PL6, 123F2, and SEM A3 from other species. Normally, the target DNA will be a genomic or cDNA library, although screening may involve analysis of RNA molecules. By varying the stringency of hybridization, and the region of the probe, different degrees of homology may be discovered.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In other embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, it is envisioned that the probes or primers described herein will be useful as reagents in solution hybridization, as in PCR™, for detection of expression of corresponding genes, as well as in embodiments employing a solid phase. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

F. Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety. Other methods of amplication are ligase chain reaction (LCR), Qbeta Replicase, isothermal amplification, strand displacement amplification (SDA), PCR™-like template- and enzyme-dependent synthesis using primers with a capture or detector moiety, transcription-based amplification systems (TAS), cylical synthesis of single-stranded and double-stranded DNA, "RACE", one-sided PCR™, and di-oligonucleotide amplification.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

G. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression cassette" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

H. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Such promoters may be used to drive β-galactosidase expression for use as a reporter gene. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al., (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al, 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |

TABLE 2-continued

Promoter and/or Enhancer

| Promoter/Enhancer | References |
| --- | --- |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) | Palmiter et al., 1982; Haslinger et al., 1985; |
| | Heavy metals | Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |

TABLE 3-continued

Inducible Elements

| Element | Inducer | References |
|---|---|---|
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

I. Initiation Signals

A specific initiation signal also may be required for efficient translation of coding sequences. These signals include the ATG initiation codon or adjacent sequences. Exogenous translational control signals, including the ATG initiation codon; may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

J. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

K. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Specific embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

L. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

M. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

N. Host Cells

In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (world-wide-web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

O. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cellbaculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

P. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

1. Adenovirus Expression Vectors

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Penicaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retrovirus Expression Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

3. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

4. Non-Viral Methods for Transfer of Expression Constructs

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle flow the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

In still another embodiment, the transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be Chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Q. Antibodies

The antibodies of the present invention are useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further below.

In another aspect, the present invention contemplates an antibody that is immunoreactive with a Fus1, 101F6, Gene 21, Gene 26, Beta*, Luca1, Luca2, PL6, 123F2, or SEM A3 molecule of the present invention, or any portion thereof. An antibody can be a polyclonal or a monoclonal antibody. In one embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses.

Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Fus1, 101F6, Gene 21, Gene 26, Beta*, Luca1, Luca2, PL6, 123F2, or SEM A3-related antigen epitopes. Additionally, it is proposed that monoclonal antibodies specific to the particular Fus1, 101F6, Gene 21, Gene 26, Beta*, Luca1, Luca2, PL6, 123F2, or SEM A3 of different species may be utilized in other useful applications In general, both polyclonal and monoclonal antibodies against Fus1, 101F6, Gene 21, Gene 26, Beta*, Luca1, Luca2, PL6, 123F2, or SEM A3 may be used in a variety of embodiments. For example, they may be employed in antibody cloning protocols to obtain cDNAs or genes encoding other Fus1, 101F6, Gene 21, Gene 26, Beta*, Luca1, Luca2, PL6, 123F2, or SEM A3. They may also be used in inhibition studies to analyze the effects of Fus1, 101F6, Gene 21, Gene 26, Beta*, Luca1, Luca2, PL6, 123F2, or SEM A3 related peptides in cells or animals. Anti-Fus1, 101F6, Gene 21, Gene 26, Beta*, Luca1, Luca2, PL6, 123F2, or SEM A3 antibodies also will be useful in immunolocalization studies to analyze the distribution of Fus1, 101F6, Gene 21, Gene 26, Beta*, Luca1, Luca2, PL6, 123F2, and SEM A3 during various cellular events, for example, to determine the cellular or tissue-specific distribution of Fus1, 101F6, Gene 21, Gene 26, Beta*, Luca1, Luca2, PL6, 123F2, and SEM A3 polypeptides under different points in the cell cycle. A particularly useful application of such antibodies is in purifying native or recombinant Fus1, 101F6, Gene 21, Gene 26, Beta*, Luca1, Luca2, PL6, 123F2, or SEM A3, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Fus1, 101F6, Gene 21, Gene 26, Beta*, Luca1, Luca2, PL6, 123F2, or SEM A3 protein, polypeptide or peptide or cell expressing high levels of Fus1, 101F'6, Gene 21, Gene 26, Beta*, Luca1, Luca2, PL6, 123F2, or SEM A3. The immunizing composition is administered in a manner effective to stimulate antibody-producing cells. Rodents such as mice and rats are preferred animals, however, the use of rabbit, sheep, and frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that Was immunized. Myeloma cell lines suited for use in hybridoma-producing fusion procedures, preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-

Ag8.653, NS1/1.Ag 4 1, Sp210-Ag14, FO, NSO/U, MPC-11, MPC11-X45-GTG 1.7 and S194/5XXO Bu1; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

R. Diagnosing Cancers Involving Fus1, 101F6, Gene 21, Gene 26, Beta*, Luca1, Luca2, PL6, 123F2, or SEM A3

Fus1, 101F6, Gene 21, Gene 26, Beta*, Luca1, Luca2, PL6, 123F2, and SEM A3 and their corresponding genes may be employed as a diagnostic or prognostic indicator of cancer. More specifically, point mutations, deletions, insertions or regulatory perturbations relating to Fus1, 101F6, Gene 21, Gene 26, Beta*, Luca1, Luca2, PL6, 123F2, and SEM A3 may cause cancer or promote cancer development, cause or promoter tumor progression at a primary site, and/or cause or promote metastasis. Other phenomena associated with malignancy that may be affected by Fus1, 101F6, Gene 21, Gene 26, Beta*, Luca1, Luca2, PL6, 123F2, and SEM A3 expression include angiogenesis and tissue invasion.

1. Genetic Diagnosis

One embodiment of the instant invention comprises a method for detecting variation in the expression of Fus1, 101F6, Gene 21, Gene 26, Beta*, Luca1, Luca2, PL6, 123F2, or SEM A3. This may comprise determining that level of Fus1, 101F6, Gene 21, Gene 26, Beta*, Luca1, Luca2, PL6, 123F2, or SEM A3 or determining specific alterations in the expressed product. Obviously, this sort of assay has importance in the diagnosis of related cancers. Such cancer may involve cancers of the brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue.

The biological sample can be any tissue or fluid. Various embodiments include cells of the brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue. Other embodiments include fluid samples such as peripheral blood, lymph fluid, ascites, serous fluid, pleural effusion, sputum, cerebrospinal fluid, lacrimal fluid, stool, or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have Fus1, 101F6, Gene 21, Gene 26, Beta*, Luca1, Luca2, PL6, 123F2, or SEM A3-related pathologies. In this way, it is possible to correlate the amount or kind of Fus1, 101F6, Gene 21, Gene 26, Beta*, Luca1Luca2, PL6, 123F2, or SEM A3 detected with various clinical states.

Alterations of a gene include deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of Fus1, 101F6, Gene 21, Gene 26, Beta*, Luca1, Luca2, PL6, 123F2, or SEM A3 produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

2. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

3. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

5. Kit Components

All the essential materials and reagents required for detecting and sequencing Fus1, 101F6, Gene 21, Gene 26, Beta*, Luca1, Luca2, PL6, 123F2, or SEM A3 and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

6. RT-PCR™ (Relative Quantitative)

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundancies made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

Still other studies may be performed using "real-time" RT-PCR™ (Higuchi et al., 1993). These assays detect PCR™ products as they accumulate instead of detecting the amount of PCR™ products accumulated after a fixed number of cycles. A method of detecting fluorescence after each PCR™ cycle is required. The fluorescence signal is plotted versus the cycle number. The cycle number is expressed as the threshold cycle ($C_T$). The initial fluorescence defines the baseline for the plot and an accumulated PCR™ product is indicated by an increase in fluorescence above the baseline. Quantification of the amount of target in a sample is determined by measuring and comparing the $C_T$ to a standard curve to determine the starting copy number.

"Real-Time" RT-PCR™ (Higuchi et al., 1993) provides more precise quantitation of the amount of target because it is determined during the exponential phase of PCR™, rather than at the endpoint. It also allows higher throughput because the use of $C_T$ values allow a larger dynamic range. Dilutions of each sample are no longer required.

7. Immunodiagnosis

Antibodies of the present invention can be used in characterizing the Fus1, 101F6, Gene 21, Gene 26, Beta*, Luca1, Luca2, PL6, 123F2, or SEM A3 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-Fus1, 101F6, Gene 21, Gene 26, Beta*, Luca1, Luca2, PL6, 123F2, or SEM A3 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Fus1, 101F6, Gene 21, Gene 26, Beta*, Luca1, Luca2, PL6, 123F2, or SEM A3 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease, alkaline phosphatase, glucose oxidase, or (horseradish) peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and H2O2, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

8. Combination of Tumor Suppressors with Other Markers

Tumors are notoriously heterogeneous, particularly in advanced stages of tumor progression (Morton et al., 1993; Fidler and Hart, 1982; Nowell, 1982; Elder et al., 1989; Bystryn et al., 1985). Although tumor cells within a primary tumor or metastasis all may express the same marker gene, the level of specific mRNA expression can vary considerably (Elder et al., 1989). It is, in certain instances, necessary to employ a detection system that can cope with an array of heterogeneous markers.

Thus, while the present invention exemplifies various tumor suppressors as a markers, any marker that is correlated with the presence or absence of cancer may be used in combination with these markers to improve the efficacy of tumor detection and treatment. A marker, as used herein, is any proteinaceous molecule (or corresponding gene) whose production or lack of production is characteristic of a cancer cell. Depending on the particular set of markers employed in a given analysis, the statistical analysis will vary. For example, where a particular combination of markers is highly specific for melanomas or breast cancer, the statistical significance of a positive result will be high. It may be, however, that such specificity is achieved at the cost of sensitivity, i.e., a negative result may occur even in the presence of melanoma or breast cancer. By the same token, a different combination may be very sensitive, i.e., few false negatives, but has a lower specificity.

As new markers are identified, different combinations may be developed that show optimal function with different ethnic groups or sex, different geographic distributions, different stages of disease, different degrees of specificity or different degrees of sensitivity. Marker combinations also may be developed, which are particularly sensitive to the effect of therapeutic regimens on disease progression.

Patients may be monitored after surgery, gene therapy, hyperthermia, immunotherapy, cytokine therapy, gene therapy, radiotherapy or chemotherapy, to determine if a specific therapy is effective.

One particularly useful combination of markers for melanoma is tyrosinase and members of the MAGE family, particularly MAGE-1 or MAGE-3. Human tyrosinase is an essential enzyme which regulates the production of melanin (Nordlund et al., 1989; Hoon et al., 1993), a group of brown or black pigments in the skin and eyes of humans. More specifically, tyrosinase catalyzes the conversion of tyrosine to Dopa and of Dopa to dopaquinone.

There are many other markers that may be used in combination with these, and other, markers. For example, b-human chorionic gonadotropin (b-HCG). b-HCG is produced by trophoblastic cells of placenta of pregnant woman and is essential for maintenance of pregnancy at the early stages (Pierce et al., 1981; Talmadge et al., 1984). b-HCG is known to be produced by trophoblastic or germ cell origin tumors, such as choriocarcinoma or testicular carcinoma cells (Madersbacher et al., 1994; Cole et al., 1983). Also ectopic expression of b-HCG has been detected by a number of different immunoassays in various tumors of non-gonadal such as breast, lung, gastric, colon, and pancreas, etc. (McManus et al., 1976; Yoshimura et al., 1994; Yamaguchi et al., 1989; Marcillac et al., 1992; Alfthan et al., 1992). Although the function of b-HCG production in these tumors is still unknown, the atavistic expression of b-HCG by cancer cells and not by normal cells of non-gonadal origin, suggests it may be a potentially good marker in the detection of melanoma and breast cancer (Hoon et al., 1996; Sarantou et al., 1997).

Another exemplary example of a marker is glycosyltransferase b-1,4-N-acetylgalacto-saminyltransferase (GalNAc). GalNAc catalyzes the transfer of N-acetylgalactosamine by b1(r) 4 linkage onto both gangliosides GM3 and GD3 to generate GM2 and GD2, respectively (Nagata et al., 1992; Furukawa et al., 1993). It also catalyzes the transfer of N-acetylgalactosamine to other carbohydrate molecules such as mucins. Gangliosides are glycosphingolipids containing sialic acids which play an important role in cell differentiation, adhesion and malignant transformation. In melanoma, gangliosides GM2 and GD2 expression, are often enhanced to very high levels and associate with tumor progression including metastatic tumors (Hoon et al., 1989; Ando et al., 1987; Carubia et al., 1984; Tsuchida et al., 1987a). Gangliosides are also expressed in melanoma, renal, lung, breast carcinoma cancer cells. The gangliosides GM2 and GD2 are immunogenic in humans and can be used as a target for specific immunotherapy such as human monoclonal antibodies or cancer vaccines (Tsuchida et al., 1987b; hie, 1985.)

GalNAc mRNA may be used as a marker of GM2 and GD2 expression and consequently a marker of either melanoma or breast cancer cells. GalNAc is generally not expressed in normal lymphocytes, epithelial cells, melanocytes, connective tissue or lymph node cells. If detected, it is in very low levels. Prostate specific antigen is a well characterized marker for prostate cancer (Gomella et al., 1997). bcr/abl gene for leukemia is a further well characterized marker that is contemplated to be useful in combination with HOJ-1.

Other markers contemplated by the present invention include cytolytic T lymphocyte (CTL) targets. MAGE-3 is a marker identified in melanoma cells and breast carcinoma. MAGE-3 is expressed in many melanomas as well as other tumors and is a (CTL) target (Gaugler et al., 1994). MAGE- 1, MAGE-2, MAGE-4, MAGE-6, MAGE-12, MAGE-Xp, and are other members of the MAGE gene family. MAGE-1 gene sequence shows 73% identity with MAGE-3 and expresses an antigen also recognized by CTL (Gaugler et al., 1994). MART-1 is another potential CTL target (Robbins et al., 1994) and also may be included in the present invention.

MUC18 is another marker that is useful in the identification of melanoma cells (Lehman et al., 1989; Lehman et al., 1987). MUC18 is a cell surface glycoprotein that is a member of the immunoglobulin superfamily and possesses sequence homology to neural cell adhesion molecules (NCAM). Other mucin family members include MUC1, MUC2, MUC3 and MUC4. These were found to be expressed at a high level in certain tumor cell lines (Hollingsworth et al., 1994) and also may be used as markers in combination with the novel HOJ-1 marker of the present invention.

Other members of the immunoglobulin superfamily of adhesion molecules associated with the development of melanoma metastasis (Denton et al., 1992) may be utilized in the present invention. Examples include intercellular adhesion molecule-1 (ICAM-1) NCAM, VCAM-1 and ELAM. Another embodiment includes carcinoma cell related molecules and molecules associated with other metastatic diseases such as carcinoembryonic antigen (CEA; Lin and Guidotti, 1989).

Other carcinoma or skin cancer associated proteins and their corresponding nucleic acids also may be utilized in the present invention. Preferred examples include melanoma antigen gp75 (Vijayasardahi et al., 1990), human cytokeratin 20, high molecular weight melanoma antigen (Natali et al., 1987) and cytokeratin 19 (K19) (Datta et al., 1994). Other markers that may be useful herein include inhibitors of the cyclin-dependent kinases, (CDK). For example, CDK4 regulates progression through the G1 phase of the cell cycle. The activity of CDK4 is controlled by an activating subunit, D-type cyclin, and by an inhibitory subunit, the p16INK4 has been biochemically characterized as a protein that specifically binds to and inhibits CDK4 (Serrano et al., 1993; Serrano et al., 1995). Other CDK-inhibitory proteins that also includes p16, p21WAF1, and p27KIP1. This list is not intended to be exhaustive, but merely exemplary, for the type and number of potential markers which may be used in the present invention.

Other proteins and their corresponding nucleic acids related to the melanin synthesis pathway may be used as markers, such as tyrosinase related protein 1 and 2 and members of the pMel 17 gene family (Kwon et al., 1993).

Preferred embodiments of the invention involve many different combinations of markers for the detection of cancer cells. Any marker that is indicative of neoplasia in cells may be included in this invention.

S. Transgenic Animals/Knockout Animals

In one embodiment of the invention, transgenic animals are produced which contain a functional transgene encoding a functional Fus1, 101F6, Gene 21, Gene 26, Beta*, Luca1, Luca2, PL6, 123F2, or SEM A3 polypeptide or variants thereof. Transgenic animals expressing Fus1, 101F6, Gene 21, Gene 26, Beta*, Luca1, Luca2, PL6, 123F2, or SEM A3 transgenes, recombinant cell lines derived from such animals and transgenic embryos may be useful in methods for screening for and identifying agents that induce or repress function of Fus1, 101F6, Gene 21, Gene 26, Beta*, Luca1, Luca2, PL6, 123F2, or SEM A3. Transgenic animals of the present invention also can be used as models for studying indications such as cancers.

In one embodiment of the invention, a Fus1, 101F6, Gene 21, Gene 26, Beta*, Luca1, Luca2, PL6, 123F2, or SEM A3 transgene is introduced into a non-human host to produce a transgenic animal expressing a human or murine Fus1, 101F6, Gene 21, Gene 26, Beta*, Luca1, Luca2, PL6, 123F2, or SEM A3 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous Fus1, 101F6, Gene 21, Gene 26, Beta*, Luca1, Luca2, PL6, 123F2, or SEM A3 by homologous recombination between the transgene and the endogenous gene; or the endogenous gene may be eliminated by deletion as in the preparation of "knock-out" animals. Typically, a Fus1, 101F6, Gene 21, Gene 26, Beta*, Luca1, Luca2, PL6, 123F2, or SEM A3 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particular embodiment, transgenic mice are generated which overexpress Fus1, 101F6, Gene 21, Gene 26, Beta*, Luca1, Luca2, PL6, 123F2, or SEM A3 or express a mutant form of the polypeptide. Alternatively, the absence of a Fus1, 101F6, Gene 21, Gene 26, Beta*, Luca1, Luca2, PL6, 123F2, or SEM A3 in "knock-out" mice permits the study of the effects that loss of Fus1, 101F6, Gene 21, Gene 26, Beta*, Luca1, Luca2, PL6, 123F2, or SEM A3 protein has on a cell in vivo. Knock-out mice also provide a model for the development of Fus1, 101F6, Gene 21, Gene 26, Beta*, Luca1, Luca2, PL6, 123F2, or SEM A3-related cancers.

As noted above, transgenic animals and cell lines derived from such animals may find use in certain testing experiments. In this regard, transgenic animals and cell lines capable of expressing wild-type or mutant Fus1, 101F6, Gene 21, Gene 26, Beta*, Luca1, Luca2, PL6, 123F2, or SEM A3 may be exposed to test substances. These test substances can be screened for the ability to enhance wild-type Fus1, 101F6, Gene 21, Gene 26, Beta*, Luca1, Luca2, PL6, 123F2, or SEM A3 expression and or function or impair the expression or function of mutant Fus1, 101F6, Gene 21, Gene 26, Beta*, Luca1, Luca2, PL6, 123F2, or SEM A3.

Promoter sequences mentioned within this document may be used to drive β-galactosidase expression. The use of a β-galactosidase reporter construct in transgenic mice may be used to identify factors which regulate Fus1, 101F6, Gene 21, Gene 26, Beta*, Luca1, Luca2, PL6, 123F2, or SEM A3 expression.

T. Methods for Treating Cancers Using Fus1, 101F6, Gene 21, Gene 26, Beta*, Luca1, Luca2, PL6, 123F2, or SEM A3

The present invention also involves, in another embodiment, the treatment of cancer. The types of cancer that may be treated, according to the present invention, is limited only by the involvement of Fus1, 101F6, Gene 21, Gene 26, Beta*, Luca1, Luca2, PL6, 123F2, or SEM A3. By involvement, it is not even a requirement that Fus1, 101F6, Gene 21, Gene 26, Beta*, Luca1, Luca2, PL6, 123F2, or SEM A3 be mutated or abnormal—the overexpression of Fus1, 101F6, Gene 21, Gene 26, Beta*, Luca1, Luca2, PL6, 123F2, or SEM A3 may actually overcome other lesions within the cell. Thus, it is contemplated that a wide variety of cancer cells may be treated using Fus1, 101F6, Gene 21, Gene 26, Beta*, Luca1, Luca2, PL6, 123F2, or SEM A3 therapy, including brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue.

In many contexts, it is not necessary that the cancer cell be killed or induced to undergo normal cell death or "apoptosis." Rather, to accomplish a meaningful treatment, all that is required is that the tumor growth be slowed to some degree. It may be that the tumor growth is partially or completely blocked, however, or that some tumor regression is achieved. Clinical terminology such as "remission" and "reduction of tumor" burden also are contemplated given their normal usage.

1. Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an expression cassette capable of providing Fus1, 101F6, Gene 21, Gene 26, Beta*, Luca1, Luca2, PL6, 123F2, or SEM A3 to that cell. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

2. Protein Therapy

Another therapy approach is the provision, to a subject, of Fus1, 101F6, Gene 21, Gene 26, Beta*, Luca1, Luca2, PL6, 123F2, or SEM A3 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

3. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that Fus1, 101F6, Gene 21, Gene 26, Beta*, Luca1, Luca2, PL6, 123F2, or SEM A3 replacement therapy could be used similarly in conjunction with chemo- or radiotherapeutic intervention. It also may prove effective to combine Fus1, 101F6, Gene 21, Gene 26, Beta*, Luca1, Luca2, PL6, 123F2, or SEM A3 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a Fus1, 101F6, Gene 21, Gene 26, Beta*, Luca1, Luca2, PL6, 123F2, or SEM A3 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either Fus1, 101F6, Gene 21, Gene 26, Beta*, Luca1, Luca2, PL6, 123F2, or SEM A3 or the other agent will be desired. Various combinations may be employed, where Fus1, 101F6, Gene 21, Gene 26, Beta*, Luca1, Luca2, PL6, 123F2, or SEM A3 is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, accelerated protons, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, Vincristin, vinblastin and methotrexate and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Fus1, 101F6, Gene 21, Gene 26, Beta*, Luca1, Luca2, PL6, 123F2, or SEM A3 expression construct is particularly preferred as this compound.

In treating cancer according to the invention, one would contact the tumor cells with an agent in addition to the expression construct. This may be achieved by irradiating the localized tumor site with radiation such as X-rays, accelerated protons, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a Fus1, 101F6, Gene 21, Gene 26, Beta*, Luca1, Luca2, PL6, 123F2, or SEM A3 expression construct, as described above.

Agents that directly cross-link nucleic acids, specifically DNA, are envisaged to facilitate DNA damage leading to a synergistic, antineoplastic combination with Fus1, 101F6, Gene 21, Gene 26, Beta*, Luca1, Luca2, PL6, 123F2, or SEM A3. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays; X-rays, accelerated protons, and/or the directed delivery of radioisotopes to tumor cells. Other forms of DNA damaging factors are also contemplated such as microwaves, and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

The inventors propose that the regional delivery of Fus1, 101F6, Gene 21, Gene 26, Beta*, Luca1, Luca2, PL6, 123F2, or SEM A3 expression constructs to patients with 3p21.3-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining Fus1, 101F6, Gene 21, Gene 26, Beta*, Luca1, Luca2, PL6, 123F2, or SEM A3-targeted therapies with chemo- and radiotherapies, it also is contemplated that combination with other gene therapies will be advantageous. For example, targeting of Fus1, 101F6, Gene 21, Gene 26, Beta*, Luca1, Luca2, PL6, 123F2, or SEM A3 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FRIT, WT-1, MEN-I, MEN-II, BRCA1, VHL, FCC, MCC, ras, myc, new, raf, erb, src, fms, jun, trk, ret, gsp, list, bcl and abl.

It also should be pointed out that any of the foregoing therapies may prove useful by themselves in treating a Fus1, 101F6, Gene 21, Gene 26, Beta*, Luca1, Luca2, PL6, 123F2, or SEM A3-related disorder. In this regard, reference to chemotherapeutics and non-Fus1, 101F6; Gene 21, Gene 26, Beta*, Luca1, Luca2, PL6, 123F2, or SEM A3 gene therapy in combination should also be read as a contemplation that these approaches may be employed separately.

4. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions. Upon formulation, solutions will be administered in a manner compatible with the dosage formulation and in such amount as is therapeutically effective.

EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Figures 1, 9A:
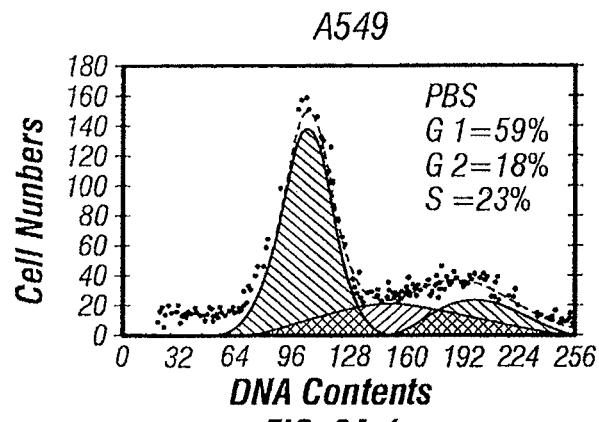
Figures 2, 9A:
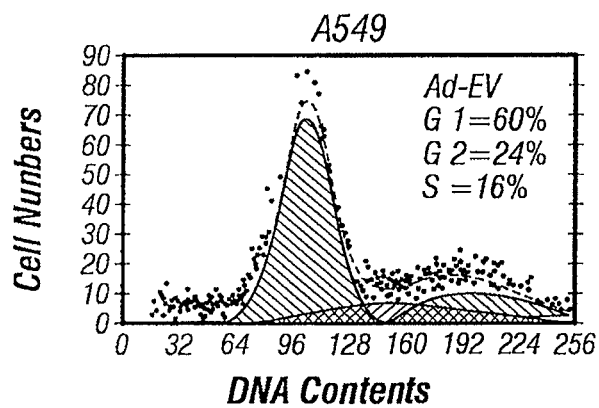
Figures 3, 9A:
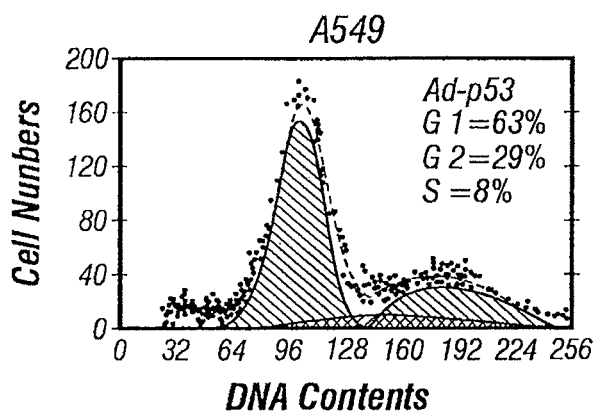
Figures 4, 9A:
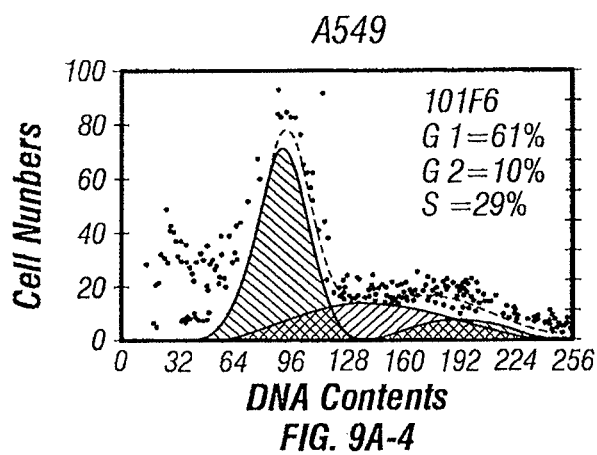
Figures 5, 9A:
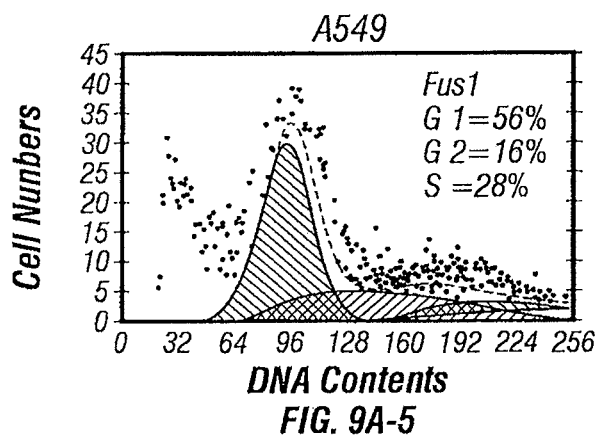

Example 1. Identification of 3p Genes in 3p21.3 Critical Region and Isolation of cDNA of 3p Genes The 3p tumor suppressor region was identified by allelotyping designed to search for areas of LOH in matched tumor/normal tissue pairs, and examine uncommon examples of homozygous deletions (FIG. 4). The most frequently involved region showing allele loss in lung cancer was mapped to the 3p21.3 region. Furthermore, multiple overlapping homozygous deletions have been found in the 3p21.3 chromosome region in SCLC lines H740 and H1450, which narrowed down the search for the tumor suppressor genes flanking about 750 kb in 3p21.3 region. Nine genes, Fus1, 101F6, NPRL2 (Gene 21), CACNA2D2 (Gene 26), HYAL1 (Luca 1), HYAL2 (Luca 2), PL6, 123F2, and Beta*, were either disrupted or immediately flanking a ~35 kb homozygous deletion found in the 3p21.3 region. SEM A3 is also present in the 3p21.3 region. The cDNAs of these genes were isolated and cloned, and mutations in these genes were determined in various tumor and tumor cell lines by single strand conformation polymorphism (SSCP) and DNA sequencing analysis (Table 4). Some of the cDNA clones showed ~50% amino acid homologies to known genes in the GeneBank, some demonstrated complete DNA sequence homology to random sequence tagged sites in the GeneBank, and one gene, Beta*, was previously unknown (Table 4).

TABLE 4

Genes Identified in the 125 kb 3p21.3 Critical Region and Status of Their cDNA Sequencing and Mutation Analysis

| Gene* | GenBAnk Number | CDNA Sequence (bp) (aa) | Mutation Analysis (Numbers) | Mutations** |
|---|---|---|---|---|
| CACNA2D2 (Gene 26) | AF040709 | 5,482 bp (1,205 aa) | Yes (60) | none |
| PL6 | U09584 | 1,860 bp (351 aa) | Yes (38) | none |
| 101F6 | AF040709 | 1,117 bp (222 aa) | Yes (38) | none |
| NPRL2 (Gene 21) | AF040707, AF040708 | 1,696 bp (203 aa) | Yes (38) | 1 stop |
| Beta* (BLU) | none | 1,739 bp (440 aa) | Yes (61) | 3 missense |
| 123F2 (RASSF1) | AF040703 | 1,502 bp (431 aa) | Yes (37) | none |
| FUS-1 | AF055479 | 1,696 bp (161 aa) | Yes (79) | 2 stop |
| HYAL2 (LUCA-2) | U09577 | 1,783 bp (473 aa) | Yes (40) | none |
| HYAL1 (LUCA-1) | U03056 | 2,565 bp (435 aa) | Yes (40) | 2 missense |

*The predicted amino acid sequence homologies to other known genes include: CACNA2D2 (Gene 26), voltage gated $Ca^{2+}$ channel alpha 2 delta regulatory subunit; NPRL2 (Gene 21), nitrogen permease regulator; 123F2, Maxp1/Norel homologue of a Ras binding protein; HYAL2 (LUCA-2) and HYAL1 (LUCA-1), a family of hyaluronidases.
**Only mutations altering the amio acid sequence are shown. In addition, polymorphisms found in more than one tumor and that did not alter the amino acid sequence are not given.

Example 2. Construction of Recombinant Adenoviral Vectors of 3p Genes

Adenoviral vectors have been widely used for gene delivery in vitro, in animal Models, preclinical research, and human clinical gene therapy trials. The high efficiency of transduction and high-level expression of transgenes mediated by adenovirus vectors in various cell types are reasons why the recombinant adenoviral vectors expressing the 3p genes (Ad-3ps) are effective tools for introduction of the functional wild-type 3p genes into tumors or tumor cell lines with abnormalities of 3p or 3p genes.

Recombinant adenoviral vectors of 3p21 genes, including Gene21, Fus1, 101F6, Gene 26, 123F2S, Luca1, and Beta*, have been constructed using the inventors' recently developed ligation-mediated plasmid-adenovirus vector construction system, pAd-RAP and pAd-RAP-Shuttle. The inventors have successfully and rapidly constructed recombinant adenoviral vectors for all ten genes in the 3p21.3 region and many other recombinant vectors using this system. Recombinant Ad-3ps can efficiently deliver 3p genes into and express them in various cell types in vitro by directly infecting target cells and in vivo by intravenous or local injection of vectors. The relative genomic locations of the tumor suppressor 3p21.3 genes in chromosome 3p and the structure of the recombinant adenoviral vectors of 3p genes are schematically demonstrated (FIG. 5).

Figure 1:
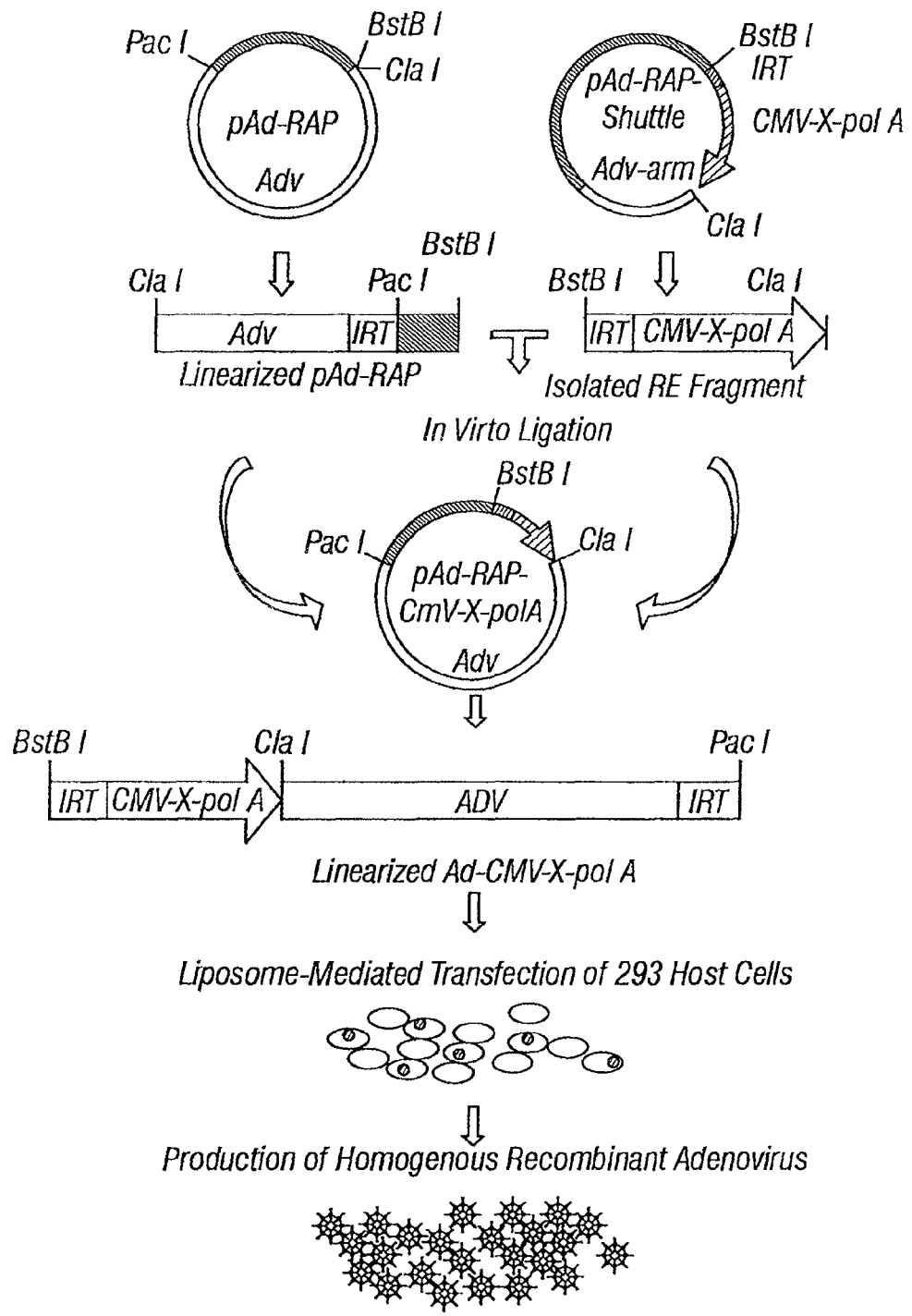
FIG. 1. Scheme of construction and production of recombinant adenovirus using pAd-RAP and pAd-RAP-Shuttle system.

The inventors have developed a novel ligation-mediated plasmid-adenovirus vector construction system, named pAd-RAP and pAd-RAP-Shuttle. This system can be used to rapidly construct recombinant adenovirus-containing plasmids in bacterial *Escherichia coli*, and then successfully produce homogeneous adenovirus in mammalian host 293 cells (FIG. 1). In this system, the transgene (X) is first placed in a plasmid shuttle vector, pAd-RAP-Shuttle, containing the adenoviral inverted repeated terminal (IRT) sequence, an expression cassette of a cytomegalovirus (CMV) promoter and bovine growth hormone (BGH) poly (A) signal sequence, and two unique restriction sites BstBI and ClaI at the 5' and 3' ends of the IRT-CMV-multiple cloning sites-BGH sequence, respectively. The BstBI/ClaI-released DNA fragment containing IRT-CMV-X-BGH is then inserted into an adenoviral plasmid vector, pAd-RAP, which contains a complete E1 and E3-deleted adenovirus type 5 genome and three unique restriction sites (PacI, BstBI, and ClaI), by in vitro ligation using BstBI and ClaI sites. After transformation into *Escherichia coli*, 90% of the transformants have the correct insert. Finally, PacI/BstBI digestion of the resulting plasmid allows release of the entire adenovirus genome-containing the 3p gene. The recombinant Ad-X DNA is then transfected into 293 cells, resulting in a homogeneous population of recombinant Ad-X.

Other promoters, poly A sequences, and restriction sites can be used. This system can be used to rapidly construct a recombinant adenovirus within 2-4 weeks. By comparison, the conventional methods, such as that using homologous recombination in mammalian cells, will usually take 3-12 months.

Figure 2:
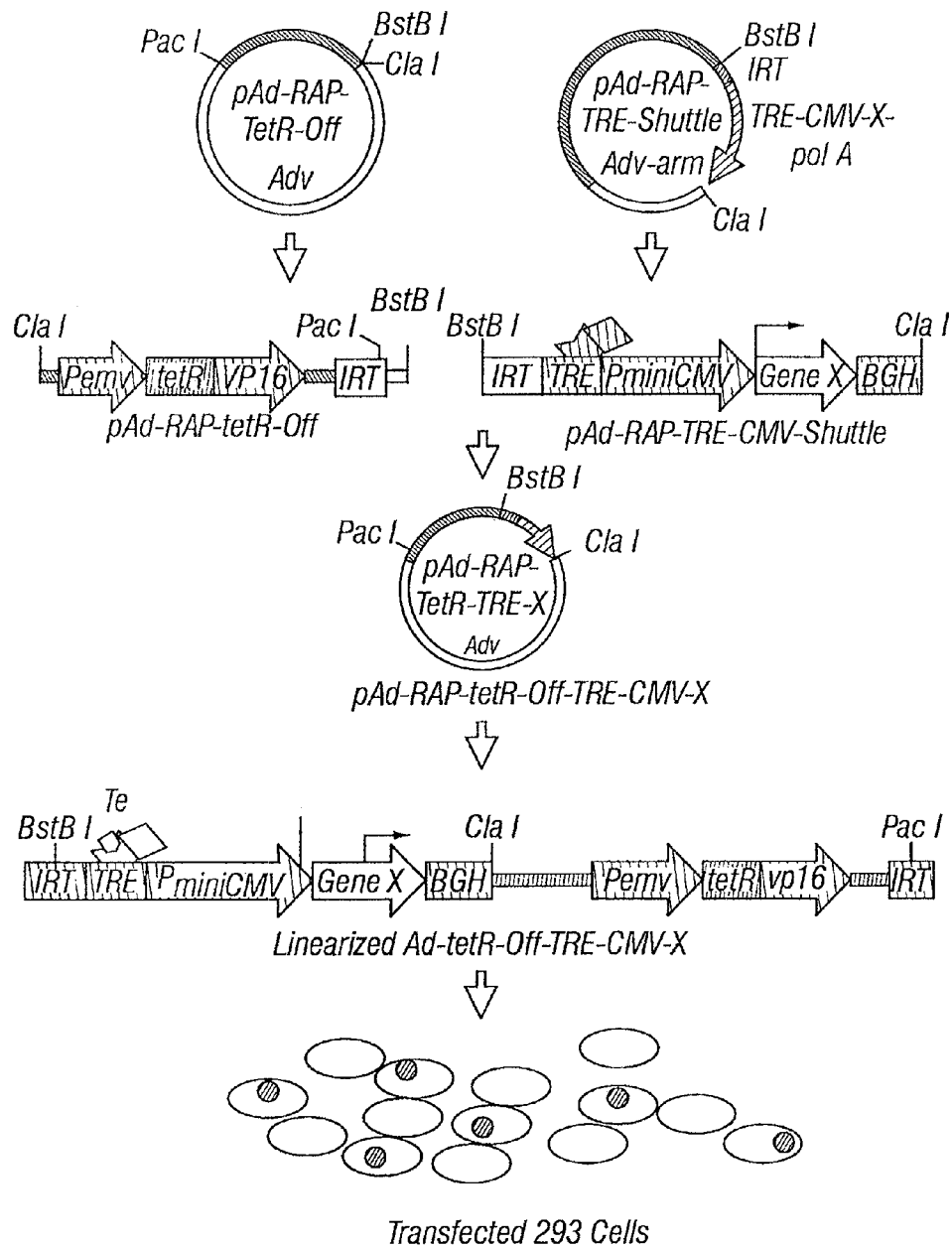
FIG. 2. Scheme of construction of recombinant adenovirus using pAd-RAP-Tet-Off and pAd-RAP-TRE-CMV-Shuttle. TetR-Off=tetracyclin resistant-off transactivator gene, TRE=TetR-Off responsive elements.

In case of failure to produce a specific recombinant Adenovirus due to the possible cytotoxicity of the transgenes in the host 293 cells, a similar system named pAd-RAP-TetR-Off and pAd-RAP-TRE-CMV-Shuttle, as, demonstrated in FIG. 2, with tetracycline regulatory elements (TRE) that can turn off transgene expression in the presence of tetracycline has been developed and can be used for the production of such vectors.

The Ad-CMV-GFP (Ad-GFP) and Ad-CMV-LacZ vectors were used to monitor transduction efficiency by the viral vectors and as nonspecific transgene expression controls. Ad-E1-(Ad-EV), an empty E1-vector, is used as a negative control. Viral titers were determined by both optical density measurement and plaque assay. Potential contamination of the viral preparation by the wild-type virus was monitored by polymerase chain reaction (PCR) analysis. Sequences of 3p genes in the viral vectors were confirmed by automated DNA sequencing. The resulting Ad-3ps are named, Ad-101F6, Ad-Gene26, Ad-Gene21, Ad-Fus1, Ad-PL6, Ad-Luca1, Ad-Luca2, Ad-123F2S, Ad-Beta*, and Ad-SEM A3, respectively.

Example 3. Preparation of PAD3ps

The preparation of protamine-adenovirus (PAD) complexes and enhancement of transduction efficiency by PADs in vitro and in vivo have been reported[47,48]. The protamine-adenovirus complexes were prepared by simply mixing $1 \times 10^{10}$ viral particles with 50 μg of protamine sulfate (10 mg/ml). The complexes were incubated for 10 min at room temperature, and then the complexed adenovirus were diluted in an appropriate volume of PBS for designated in vitro or in vivo experiments.

Example 4. Preparations of LDC3ps and LPD3ps

The liposome (DOTAP:Cholesterol) (LDC), plasmid DNA, and LDC-3p DNA complexes (LDC3ps) were prepared as described by Templeten et al.[49]. LDC3ps were formulated as 80 nmol liposome:50 μg DNA in 5% Dextral water (D5W) at a total volume of 100 μl for intravenous injection to one mouse. Liposome (DOTAP:Cholesterol):Protamine:DNA (LPD) were prepared based on the method of Hung[50].

Example 5. Effects of Overexpression of 3p Genes on Tumor Cell Growth

To study biological function of new tumor suppressor genes, experiments are conventionally performed in tumor cell lines either transiently or stably transfected by wild type gene-expressing plasmids. The Ad-3p vectors can offer several advantages over plasmids for 3p gene delivery in vitro and in vivo: 1) high efficiency (>80%) of transduction and high level of 3p gene expression can be easily achieved in a wide spectrum of cell types by simply adjusting the multiplicity of infection (MOI) of viral particles to target cells, consequently, the Ad-3ps can be used to evaluate effects of 3p genes as a individual or as a whole region 2) Ad-3ps-transduction can be directly applied to tumor cells to study their effect on tumorigenicity in animals without selection of stably transduced colonies, by which problems associated with colony selection process and unknown effectors or factors generated in resulting cell colonies can be avoided; and 3) Ad-3ps can be directly used to evaluate the role of 3p genes as a tumor suppressor gene region in vivo by either intravenous or intratumoral injection of animals with the individual or combined Ad-3p vectors.

The biological function of these newly isolated 3p genes is characterized in this invention by liposome- and recombinant adenoviral vector-mediated gene transfer both in vitro and in vivo. Human lung cancer cell lines (H1299, H358, H460, and A549), with varied status of chromosome 3p or individual 3p genes and a normal human bronchial epithelial cell (HBEC) line were used to evaluate the effects of 3p genes on cell growth arrest, proliferation, apoptosis, and cell cycle kinetics in vitro and on growth of the primary and metastatic tumors in animal models.

To test the hypothesis that the 3p genes function as tumor suppressors in vitro, the inventors performed a series of experiments to study the effects of overexpression of the 3p genes on cell proliferation in various human non-small cell lung cancer cells and a normal human bronchial epithelial cell line (HBEC) varying in status of 3p chromosomal structure or genes and gene products (Table 5) by liposome- or adenoviral vector-mediated 3p gene transfer. One of these lines is H1299, a NSCLC cell line that contains an internal homozygous deletion of p53, and has no normal copy of chromosome 3 with LOH of 3p alleles and has very high levels of telomerase expression and activity. A549, is a lung carcinoma cell line that contains wild-type p53 with abnormal 3p alleles; H358 is a lung cancer cell line that contains wild-type p53 with two 3p alleles; and H460 is, a lung cancer cell line that contains wild-type p53 with loss of noe allele of the 3p21.3 region (Table 5). Normal HBECs or fibroblast cells (Clonetics Inc., Walkersville, Md.) were also used to evaluate the general toxicity of the 3p genes and Ad-3ps. The 293 cell line was used in the construction, amplification, and titration of adenoviral vectors. The cells were maintained in Dulbecco's Modified Eagle Medium (DMEM) containing 4.5 g/l of glucose with 10% FBS.

TABLE 5

Status of 3p Genes in Human Lung Cancer Cell Lines and Normal HBEC*

| Cell Line | Origin | 3p Genes | P53 | hTERT |
|---|---|---|---|---|
| H1299 | Lung, large | LOH | Deletion | High Activity |
| A549 | NSCL | LOH | WT | Active |
| H460 | Lung, Large | LOH | WT | Active |
| H358 | NSCL | WT | Deletion | Active |
| HBEC | Bronchial Epithelia | Normal | Normal | undetected |

*Abbreviation: HBEC, human bronchial epithelia cell, NSCL, non-small cell lung cancer, LOH, loss of heterozygosity, WT, wild type.

The Ad-3p vectors, protamine-Ad-3p complexes (PAD3ps) or liposome (DOTAP)-3p plasmid DNA complexes (LPD3ps) developed in this invention can be used to deliver 3p genes efficiently to the tumor cells in vitro by direct transduction and to the primary and distant lung or other metastatic tumor sites in vivo by systemic administration. The spontaneous or experimental pulmonary metastasis models of human lung cancers H1299 and A549, as well as other cancers, can be used to study the effects of 3p genes on tumor progression and metastasis by systemic treatment of lung metastatic tumors in mice through intravenous injection of either PAD3p or LPD3p complexes.

In experiments with liposome-mediated 3p gene transfer in H1299 cells, six genes out of the nine, Fus1, 101F6, Luca1, 123F2S, Beta*, and Gene 21, demonstrated varied degrees (20-65%) of cell growth inhibition in H1299 transfectants after 48 hr of transfection, compared to untransfected and empty CMV vector-transfected controls. Three other genes Gene 26, PL6, and Luca 2 showed no significant effects on H1299 cell growth under the same experimental condition (Table 6). The observed inhibitory effect of Fus1, Beta*, 123F2S, and Gene 21 on H1299 cell growth were comparable to that of highly cytotoxic gene Bak under the same experiment conditions (Table 6). The three other genes Gene 26, PL6, and Luca 2 showed no significant effects on H1299 cell growth under the same experimental conditions. Varied degrees (10-40%) of induction of apoptosis and altered cell cycle kinetics (changes of cell populations at G0, G1 and S phases) were observed in H1299 cells transfected with plasmids containing genes Fus1, 101F6, 123F2S, Luca, and Beta* by FACS analysis with TUNEL reaction and PI staining.

TABLE 6

Effects of DOTAP-mediated 3p Gene Expression on Growth of H1299 Cells (48 h)

| | Data from MDACC (Transfection) (% Cell Viability ± STDEV) | Data from UTSMC (Colony Formation)[†] (% Cell Viability ± STDEV) |
|---|---|---|
| PBS | 100 | ND |
| CMV-EV | 85 ± 9.5 | 100 |
| GFP | 84 ± 7.2 | ND |
| Bak | 54 ± 5.1 | ND |
| 101F6 | 76 ± 3.5 | 52 ± 10.0 |
| Fus1 | 78 ± 2.1 | 49 ± 14.0 |
| Gene 21 | 45 ± 6.5 | 83.7 ± 17.7 |
| Gene 26 | 88 ± 12.5 | 40 ± 0.00 |
| Luca 1 | 81 ± 2.8 | 66 ± 27.2 |
| Luca 2 | 100 ± 9.8 | 80 ± 27.6 |
| PL6 | 100 ± 13.6 | 95 ± 53.8 |
| 123F2S | 67 ± 3.8 | 58 ± 0.0 |
| Beta* | 35 ± 2.3 | 51 ± 8.5 |

[†]Data from colony formation assay in 3p gene-expressing plasmid DNA-tranfected cells, relative to that of empty plasmid-transfected cells. ND, undetermined; STDEV, standard deviation from the mean of the repeated experiments.

Figures 6, 9A:
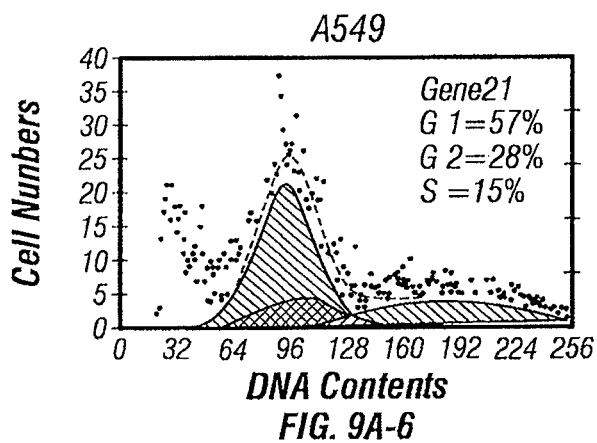
Figures 1, 9B:
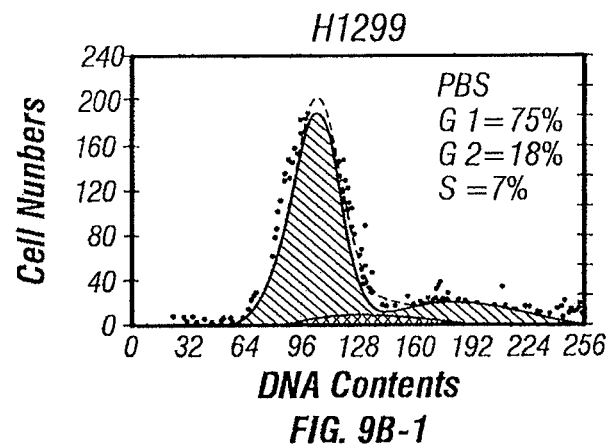
Figures 2, 9B:
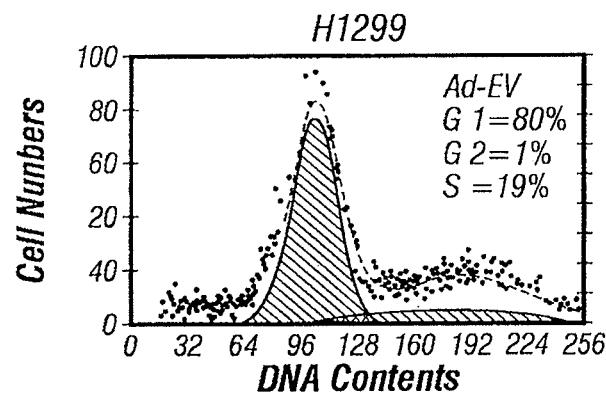
Figures 3, 9B:
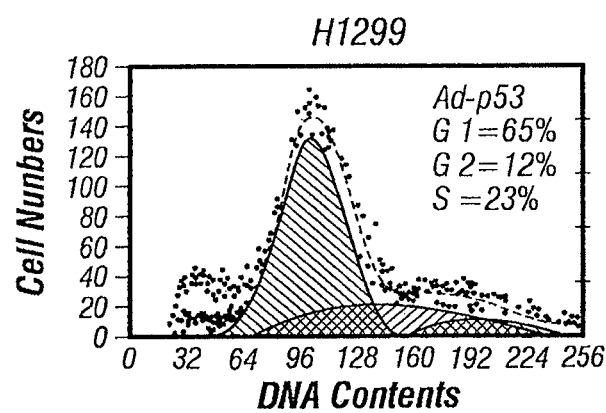
Figures 4, 9B:
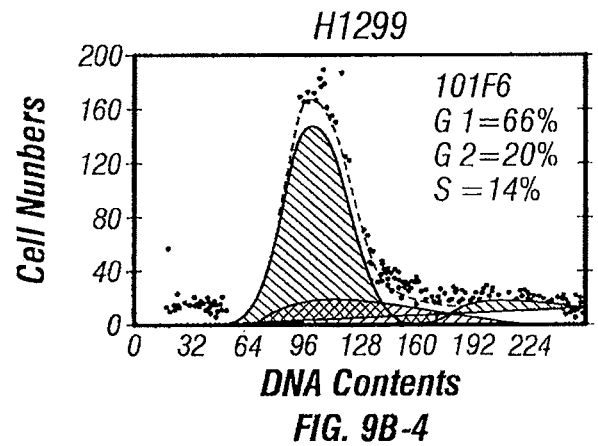
Figures 5, 9B:
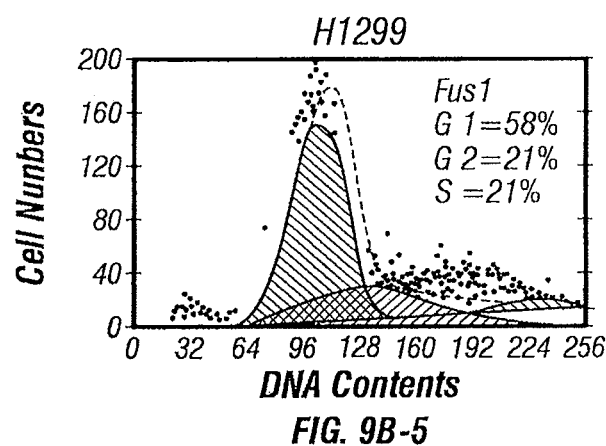
Figures 6, 9B:
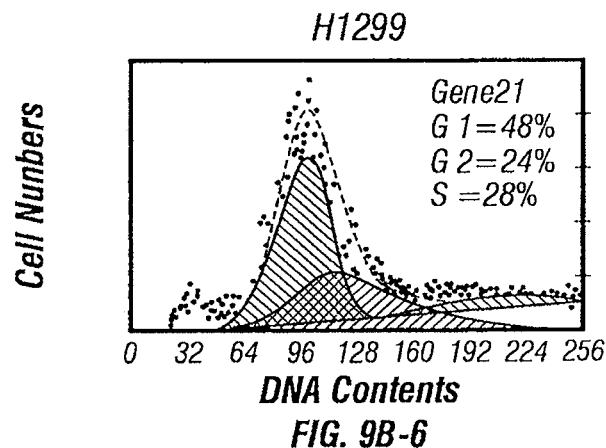

Effects of 3p genes on tumor cell growth were further characterized by recombinant-adenoviral vector-mediated 3p gene transfer in various lung cancer cell lines and a normal HBEC line. To test the specificity of the observed inhibitory effects of 101F6, Fus1, and Gene21 overexpression on tumor cell proliferation and the potential cytotoxicity of the overexpressed 3p genes, the inventors analyzed the effect of these 3p genes on cell proliferation in Ad-3p-transduced wild type 3p-containing H358 cells and normal HBEC cells (FIG. 6). Cells in each line were transduced in vitro by Ad-101F6, Ad-fus1 and Ad-Gene21 vectors administered at various multiplicity of infections (MOIs) in viral particles/cell (vp/c); cells treated with PBS were used as mock, empty vector Ad-EV as negative, Ad-LacZ as non-specific, and Ad-p53 as positive controls, respectively. A less than 10% loss of cell viability in Ad-3p-transduced hBEC and a less than 20% loss in H358 cells at various MOIs, were observed when compared with that in untransduced control cells. Similar losses were also observed in Ad-EV- and Ad-LacZ transduced cells and slightly higher loses in Ad-p53-transduced cells throughout the posttransduction time course, suggesting that no generalized cytotoxicity was associated with overexpression of these 3p genes. The transduction efficiency was determined by examining the GFP-expressing cells in the Ad-GFP transduced cell population under a fluorescence microscope.

The transduction efficiency of the adenoviral vectors was greater than 80% at the highest MOI applied for each cell line. Cell proliferation was analyzed by determining the viability of cells at 1, 3 and 5 days posttransduction, respectively. Cell viability was significantly reduced in Ad-101F6, Ad-Fus1, and Ad-Gene21 transduced A549 and H460 cells which exhibit LOH in 3p region but contain wild-type p53 and H1299 cells which contains homozygous deletions of 3p region and p53 (FIG. 6). In all cases, the viability of transduced cells was compared with that of untransduced (PBS-treated) control cells (whose viability was set at 100%).

The overexpression of 3p genes in these Ad-3p tranfectants was verified by a quantitative Real Time RT-PCR, and known concentrations of human total RNA, primers, and TaqMan probes for β-actin DNA were used as standards and as a internal control (FIG. 7). TaqMan probes and primers of 3p genes were designed using a Primerexpress software (Perkin Elmer Applied Biosystems, Foster City, Calif.). Human genomic DNA or total RNAs were used as template standards and human β-actin or glyceraldehyde-3-phosphate dehydrogenase (GAPDH) TaqMan probes and primers as controls. Total RNA was isolated from Ad-3p transduced tumor cells or tumor specimen using TRIZOL. Real time RT-PCR and quantification of RT-PCR products were performed and analyzed using a TaqMan Gold RT-PCR Kit, an ABI Prism 7700 Sequence Detection System and equipped software. These results show that overexpression of these 3p genes can inhibit tumor cell growth in vitro.

Example 6. Effects of 3p Genes on Tumor Cell Growth and Proliferation

To test whether the growth properties of various lung cancer cells with abnormalities of 3p or 3p genes could be altered by the introduction of wild-type 3p genes, cell viability in Ad-3p-transduced tumor cells at varied MOIs at designated posttransduction time intervals are assayed by XTT staining as described previously,[44] and the untransduced and Ad-EV-, Ad-GFP-, or Ad-LacZ-transduced cells were used as controls. Each experiment was repeated at least three times, with each treatment given in duplicate or triplicate. Proliferation of the Ad-3p-transduced cells were analyzed by an immunofluorescence-enzyme-linked immunosorbent assay for incorporation of bromodeoxyuridine (BrdU) into cellular. Ad-3p-transduced normal HBECs were used to evaluate the possible general toxicity of the 3p genes and Ad-3ps in vitro. Transcription and expression of 3p genes in Ad-3p-transduced cells were examined by reverse transcriptase-polymerase chain reaction or Northern- and Western-blot analysis with anti-3p protein polyclonal antibodies.

Example 7. Western Blot Analysis of Expression of 3p Genes in Ad-3p-Transduced Cells Expression of 3p genes in Ad-3p-transduced cells was analysed by Western blot, using polyclonal antibodies against polypeptides derived from predicted 3p amino acid sequences or monoclonal antibodies against c-myc of FLAG tags in 3p fusion proteins. Cells grown in 60 mm-dishes ($1-5 \times 10^6$/well) were treated with Ad-3ps, and PBS alone was used as a control. Proteins were separated by SDS-PAGE. Each lane was loaded with about 60 μg cell lysate protein and electrophoresed at 100 V for 1-2 h. Proteins were then transferred from gels to Hybond-ECL™ membranes. Membranes were blocked in blocking solution (3% dry milk, 0.1% Tween 20 in PBS) for 1 h at room temperature. Membranes were then incubated with 1:1000 dilution of rabbit anti-human 3p peptides or anti-myc or FLAG monocolonal antibodies, and 1:1000 dilution of mouse anti-β-actin monocolonal antibodies. Immunocomplexes were detected with secondary HRP-labeled rabit anti-mouse IgG or goat anti-rabit IgG antibodies using an ECL™ kit (Amersham International).

Example 8. Induction of Apoptosis by 3p Genes in Ad-3p-Transduced Tumor Cells

The ability of exogenous 3p genes to induce apoptosis and their impact on cell-cycle processes in the Ad-3p-transduced H1299, A549, H460, H358, and HBEC cells were analyzed by FACS using the terminal deoxynucleotidyl transferase-mediated dUTP nick end labeling (TUNEL) reaction (FIG. 8). Induction of apoptosis was detected in Ad-3p-transduced H1299 (FIG. 8A), A549 (FIG. 8B), and H460 (FIG. 8C) cells, but not in H358 (FIG. 8D) and HBEC (FIG. 8E) cells. More than 15-20%, 40-65%, and 75% of cells were apoptotic at day 5 after transduction with Ad-101F6, Ad-Fus1, and Ad-Gene21 in the transduced H1299, A549, and H460 cells, respectively, whereas only about 7% and 10% of cells treated with PBS alone and transduced with Ad-EV vector, respectively, were TUNEL-positive at the same time periods. The level of induction of apoptosis in the Ad-3p-transduced cells increased with time posttransduction and correlated with the viability of cells (FIG. 6). The inhibition of tumor cell proliferation by 3p genes are mediated directly or indirectly through induction of apoptosis.

Example 9. Induction of Apoptosis and Alteration of Cell Cycle Kinetics Ad-3p-Transduced Cells Inhibition of tumor cell growth and proliferation by tumor suppressor genes is usually characterized by induction of apoptosis and alteration of cell cycle processes. Thus, 3p gene-induced apoptosis and cell cycle kinetics were analyzed by flow cytometry using the terminal deoxy transferase deoxyuridine triphosphate (dUTP) nick-end labelling (TUNEL) reaction with fluorescein isothiocyanate-labeled dUTP (Roche Molecular Biochemicals) and propidium iodide staining, respectively. In brief, cells ($1 \times 10^6$/well) are seeded on six-well plates and transduced with Ad-3p constructs; untreated and Ad-EV-, Ad-GFP-, or Ad-LacZ-transduced cells were used as controls. Cells were harvested at designated posttransduction times and then analyzed for DNA fragmentation and apoptosis by TUNEL reaction and for DNA content and cell cycle status by propidium iodide staining using flow cytometry, respectively, as described previously. The cell-cycle profiles in the Ad-101F6, Ad-Fus1, and Ad-Gene21-transduced cells appeared to be significantly affected by overexpression of these genes at later G2 and S phases stages compared to those in the untransduced and Ad-EV-transduced controls at 3 days posttransduction (FIG. 9).

Example 10. Suppression of Tumor Growth by Overexpression of 3p Genes In Vivo

Figure 10:
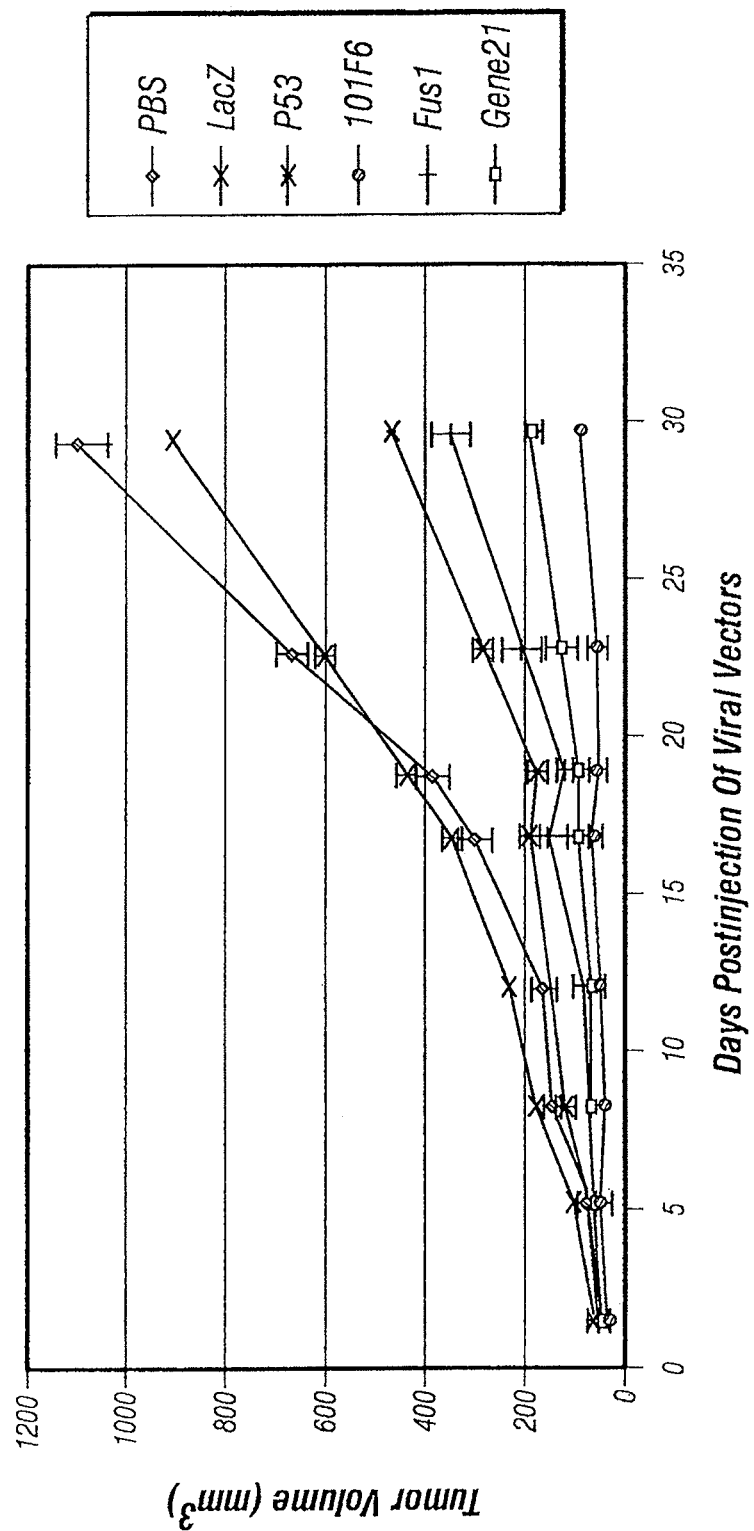
FIG. 10. Effect of overexpression of 3p genes on A549 tumor growth by intratumoral injection of Ad-3p vectors in nude mice.

The tumor suppressor function of 3p genes, 101F6, Fus1, and Gene21 were evaluated in vivo by direct intratumoral injection of these. Ad-3p vectors into the A549 subcutaneous tumors in nude mice (FIG. 10). The growth of tumors was recorded from first injection until 20 days after last injection. All of the tumors in the mice treated with Ad-101F6, Ad-Fus1, and Ad-Gene21 showed significantly suppressed growth compared with tumors.

Example 11. Effects of 3p Gene Expression on Tumorigenicity and Tumor Growth In Vivo For the tumorigenicity study, H1299 or A549 cells were transduced in vitro with Ad-3p at an appropriate MOI with phosphate-buffered saline (PBS) alone as a mock control, Ad-EV as a negative control, and Ad-LacZ as a nonspecific control. The transduced cells were harvested at 24 h and 48 h posttransduction, respectively. The viability of the cells was determined by trypan blue exclusion staining. Viable cells ($1 \times 10^7$) were then injected subcutaneously into the right flank of 6- to 8-week-old female nude mice. Tumor formation in mice was observed two or three times weekly for up to 3 months. Tumor dimensions were measured every 2 or 3 days.

To study the effect of 3p genes on tumor growth, H1299 or A549 cells were used to establish subcutaneous tumors in nude mice. Briefly, $1 \times 10^7$ cells were injected into the right flank of 6- to 8-week-old female nude mice. When the tumors reached 5 to 10 mm in diameter (at about 2 weeks postinjection), the animals were intratumorally injected with Ad-3p and control vectors, respectively, 4 to 5 times within 10 to 12 days for at a total dose of 3 to $5 \times 10^{10}$ pfu per tumor. Tumor size was measured and calculated as described above. At the end of the experiment, the animals were killed and the tumors were excised and processed for pathological and immunohistochemical analysis.

Figure 11:
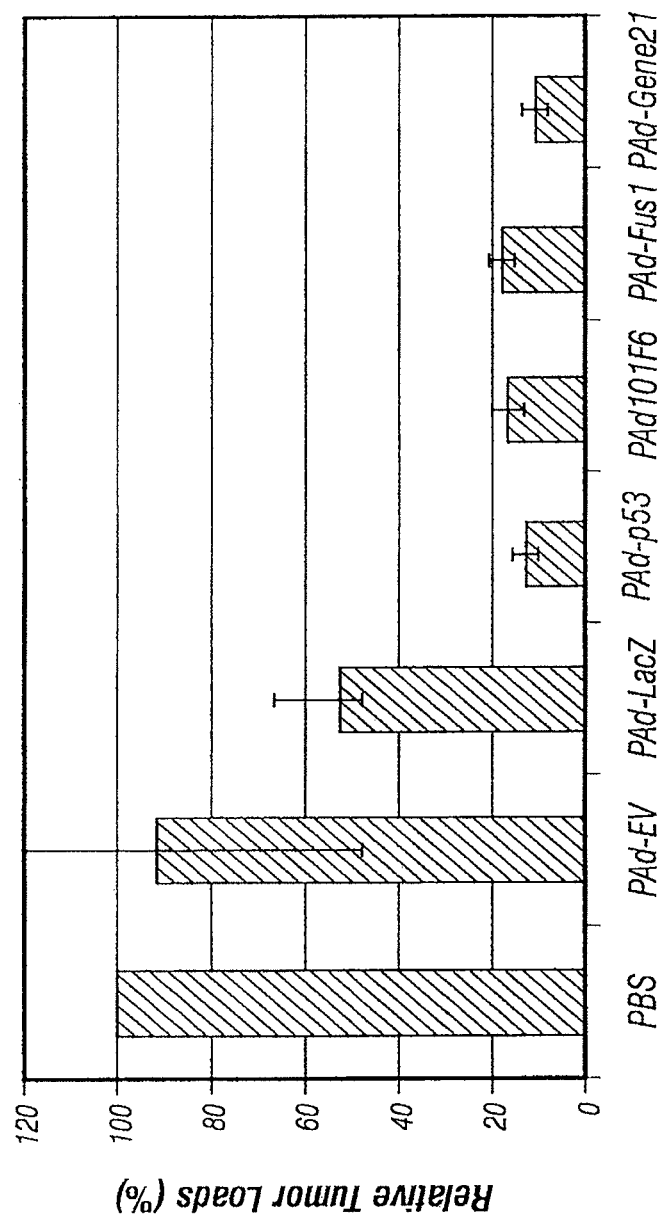
FIG. 11. Effect of overexpression of 3p genes on A549 lung metastatic tumor growth by systemic injection of protamine-Ad-3p vector complexes in nude mice.

Example 12. Inhibition of Lung Metastatic Tumor Growth by Protamine-Adenovirus Complex-Mediated 3p Gene Transfer In Vivo The inventors have developed a novel Protamine/Adenovirus complex for enhancement of the efficiency of adenovirus-mediated gene transfer in vitro and for systemic delivery of recombinant adenovirus to lung and other organs in vivo by intravenous injection of the complex. The Protemine-Ad-3p complexes (PAd3ps) were used to study the effects of overexpression of 3p genes on pulmonary metastatic tumor growth in A549 experimental lung metastasis model in nude mice (FIG. 11). The metastatic tumor growth was significantly inhibited in PAd-101F6, PAd-Fus1, and PAd-Gene21-treated mice, compared with those in control groups. These data are consistent with results obtained from Ad-3p-treated subcutaneous tumors. Therefore, the 3p genes play a role in suppression of tumor growth and inhibition of tumor progression in vivo.

Example 13. Effect of 3p Genes on Metastatic Tumor Growth by LPD3p- or PAD3p-Mediated 3p Genes Transfer In Vivo The experimental lung metastasis models of H1299 and A549 cells were used to study the effects of 3p genes on tumor progression and metastasis by systematic treatment of lung metastatic tumors through intravenous injection of either PAD3p or LPD3p complexes. A549 cells ($1-2 \times 10^6$) in 200 μl PBS were intra venially inoculated with nude mice and H1299 cells ($1-2 \times 10^6$) with SCID mice, respectively. Experimental metastatic tumor colonies were formed 7-10 days post-inoculation. PAD3ps and control complexes were administered to animals by intravenous injection every other two days for 3 times each at a dose of $2-5 \times 10^{10}$ viral particles/200-500 μg protamine, in a total volume of 200 μl per animal. Alternatively, LPD3ps were applied by intravenous injection every day for 6 times each at a dose of 120 nmol liposome:6 μg protamine:50 μg DNA, in a total volume of 200 μl per animal. Animals were killed two weeks post last injection. Lung metastasis tumors were stained with Indian ink[51], tumor colonies on the surfaces of lung were counted under an anatomic microscope, and then the lung tissue were sectioned for further pathologic and immunohistochemical analysis.

Example 14. Analysis of Telomerase Activity and Cellular Immortality

Activation of the enzyme telomerase, which has been associated with cellular immortality, may constitute a key step in the development of human cancer. Because of the nearly universal deregulated expression of telomerase in lung cancer cells and the evidence for involvement of 3p genes in the telomerase repression regulatory pathway, it will be important to study whether the alteration of tumor cell growth and proliferation implied by the introduction of wild-type 3p21.3 genes is associated with repressed telomerase activity in Ad-3p transductants. To assay telomerase activity, untransduced and Ad-3p- and control vector-transduced cells ($10^5$) are harvested and prepared as described previously.[31] The cell extract equivalent to approximately $10^3$, $10^2$, or $10^1$ cells is used for each telomerase assay. A standard telomeric repeat amplification protocol procedure, which is capable of detecting telomerase activity in as few as 10 to 100 lung cancer cells, is performed with modifications as described.[32,45,46]

Example 15. 123F2 (RASSF1A) in Lung and Breast Cancers and Malignant Phenotype Suppression[339]

I. Characterization of the 123F2 (RASSF1) Gene

Figure 12C:
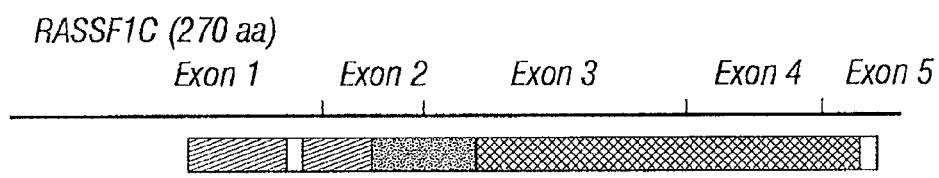
Figure 12D:
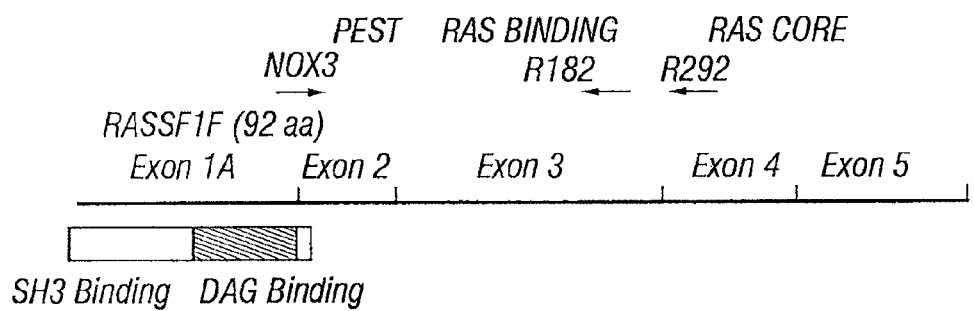

To determine if the 123F2 (RASSF1A) gene was mutated in lung and breast cancers, the inventors performed extensive mutational analysis of the RASSF1A isoform with the use of single-strand conformation polymorphism assays on genomic DNA. The inventors had previously found no RASSF1C mutations in 77 lung cancer cell line samples[346]. By use of the RASSFIA sequence as a reference, the inventors, found several polymorphisms, including the following: codon 21 (AAG to CAG), Lys to Gln; codon 28 (CGT to CGA), no amino acid change; codon 49 (GGC to GGT), no amino acid change; codon 53 (CGC to TGC), Arg to Cys; codon 129 (GAC to GAG), Asp to Glu; codon 133 (GCT to TCT), Ala to Ser; and codon 325 (TAT to TGT), Tyr to Cys. The 123F2 (RASSF1) gene is shown in FIG. 12.

II. Expression of RASSFIA and RASSF1C in Lung and Breast Cancer Cell Lines

123F2 (RASSF1) is located within a region frequently affected by allele loss during growth of lung, breast, head and neck, kidney, and cervical tumors[341-345]. The inventors investigated whether 123F2 (RASSF1A) and RASSF1C are expressed in lung and breast cancer cell lines. The inventors used isoform-specific RT-PCR to examine the expression of 123F2 (RASSF1A) and RASSF1C in lung and breast tumor cell lines and in normal lung and breast epithelial cultures (FIG. 13).

Isoform-specific RT-PCR assays were used for analysis of RASSF1A and RASSF1C expression. Primers for RASSFIC were Nox3 (5'-CTGCAGCCAAGAGGACTCGG-3') (SEQ ID NO: 3) and R182 and for RASSF1A were either PKCDF or NF (5'-TGCAAGTTCACCTGCCAC-3') (SEQ ID NO: 4) and R182 (FIG. 12. C). Total RNA was isolated from previously described lung and breast cancer cell lines grown in RPMI-1640 medium supplemented with 5% fetal bovine serum (complete medium) by Trizol extraction. Four micrograms of total RNA was reverse transcribed by use of GIBCO-BRL Superscript First Strand cDNA Kit. All cDNA preparations were tested for the ability to amplify a non-transcribed genomic sequence immediately upstream of the first exon of the RASSF1A transcript. Any cDNAs that produced a product from this sequence were discarded because they were contaminated with genomic DNA.

The inventors also assessed the expression of RASSF1A after exposure to 5-aza-2'-deoxycytidine, a drug that inhibits DNA methylation. The inventors exposed subconfluent cultures of the RASSF1A-nonexpressing NSCLC line NCI- H157 to 0.5 p.M 5-aza-2'-deoxycytidine for 48 hours, after which the inventors isolated total RNA and performed RT-PCR for RASSF1A, RASSF1C, and glyceraldehyde-3-phosphate dehydrogenase (GAPDH). RT-PCR of GAPDH transcripts was performed with the use of forward primer GAPDH-C (5'-CATGACAACTTTGGTATCGTG-3') (SEQ ID NO: 5) and reverse primer GAPDH-D (5'-GTGTCGCT-GTTGAAGTCAGA-3') (SEQ ID NO: 6). RTPCR products were separated by agarose gel electrophoresis and visualized after staining with ethidium bromide.

123F2 (RASSF1A) was expressed in normal lung epithelial cultures (NHBE and SAB cultures), in a normal breast epithelial culture (FIG. 13, C), but not in 32 (100%) of 32 SCLC lines, in 17 (65%) of 26 NSCLC cell lines, and in 15 (60%) of 25 (60%) breast cancer cell lines. Representative data are shown in FIG. 13. By contrast, RASSF1C was expressed in nearly all of the lung and breast cancer cell lines tested, with the exceptions of several lung and breast cancer lines with known homozygous deletions that include the 123F2 (RASSF1) locus. In resected lung adenocarcinomas, 123F2 (RASSF1A) was expressed in only two of five cancers, while RASSF1C was expressed in all cancers (FIG. 13, C).

During RT-PCR analysis for 123F2 (RASSF1A), the inventors frequently noted two closely spaced bands in RASSF1A-expressing tumors and in NHBE cultures (FIG. 13). The inventors sequenced these RT-PCR products and found that the larger band corresponded to 123F2 (RASSF1A), while the smaller product represented a different transcript, RASSF1F (GenBank Accession #AF286217). This transcript skips exon 1C to produce an mRNA encoding a predicted truncated peptide of 92 amino acids ending within the DAG-binding domain (FIG. 12. D). In nearly all of the samples, RASSF1F is expressed when 123F2 (RASSF1A) is expressed. However, in some breast cancers and normal breast epithelial cultures (FIG. 13), 123F2 (RASSF1A) is expressed without RASSF1F expression.

III. Methylation Status of the 123F2 (RASSF1A) Promoter Region

Aberrant promoter methylation in tumors has been found to lead to the loss of gene expression of several tumor suppressor genes in human cancers[348]. To assess whether the loss of 123F2 (RASSF1A) expression in lung cancer was the result of promoter hypermethylation, the inventors determined the CpG methylation status in the 5' region of 123F2 (RASSF1A) (from −800 to +600 bp of the predicted 123F2 (RASSF1A) transcript start site) by sequencing sodium bisulfate-modified DNA from eight lung cancer cell lines.

The methylation status of the presumed RASSF1A and RASSF1C promoter regions was determined by methylation-specific PCR. Genomic DNAs from lung cancer cell lines not expressing RASSF1A (NCI lines H1299, H1184, H1304, H841, H2108, and H128) or expressing RASSF1A (H1792 and H2009) were modified by sodium bisulfate treatment[352,353]. Bisulfite treatment converts cytosine bases to uracil bases but has no effect on methylcytosine bases. PCR amplification followed by sequencing of the PCR fragments identifies specific CpG dinucleotides in the promoter region that are modified by methylation[352, 354, 355]. PCR primers were designed to amplify genomic sequences in the presumed promoter regions of RASSF1A (cosmid Luca12; GenBank Accession #AC002481 nucleotides 17730-18370) and RASSF1C (GenBank Accession #AC002481 nucleotides 21022-21152 and 21194-21332).

The resulting PCR fragments were sequenced by automated fluorescence-based DNA sequencing to determine the methylation status.

The data on CpG methylation in RASSF1A-nonexpressing lung cancer cell lines were used to design methylation-specific PCR.sup.352 primers for the RASSF1A 5' promoter region: The primers to detect the methylated form were 5'-GGGTTTTGCGAGAGCGCG-3' (forward; SEQ ID NO: 7) and 5'-GCTAACAAACGCGAACCG-3' (reverse; SEQ ID NO: 8), and the primers to detect the unmethylated form were 5'-GGTTTTGTGAGAGTGTGTTTAG-3' (forward; SEQ ID NO: 9) and 5'-CACTAACAAACACAAAC-CAAAC-3' (reverse; SEQ ID NO: 10). Each primer set generated a 169-base-pair (bp) product. Methylation-specific PCR cycling conditions consisted of one incubation of 15 minutes at 95° C., followed by 40 cycles of a 30-second denaturation at 94° C., 50 seconds at an annealing temperature (64° C. for methylation-specific and 59° C. for unmethylated-specific primers), a 30-second extension at 72° C., and a final extension at 72° C. for 10 minutes. PCR products were separated in 2% agarose gels. Lymphocyte DNA, methylated in vitro by CpG (SssI) methylase (New England Biolabs, Inc., Beverly, Mass.) following the manufacturer's directions, was used as a positive control. A water blank was used as a negative control.

All of the six lung cancer cell lines not expressing 123F2 (RASSF1A) exhibited methylation of almost all CpG dinucleotide, sites in the putative promoter region. The two lung cancer cell lines that did express 123F2 (RASSF1A either were not methylated at these CpG sites or showed limited methylation. By contrast, no methylation was found in CpG sites in the presumed RASSF1C promoter region of these eight cell lines.

To confirm that promoter hypermethylation contributes to the lack of expression of 123F2 (RASSF1A) in the lung cancer cell lines, the inventors assessed the effect of 5-aza-2'-deoxycytidine, a drug that inhibits DNA methylase, on 123F2 (RASSF1A) expression. The inventors exposed the RASSFIA-nonexpressing NSCLC line NCI-H157 to 5-aza-2'-deoxycytidine and found re-expression of 123F2 (RASSF1A) by this cell line but little or no change in the expression of the housekeeping gene GAPDH or in the expression of RASSF1C (FIG. 14).

IV. Methylation-Specific PCR Analysis of the Promoter Region of 123F2 (RASSF1A) in Lung and Breast Cancers To determine the methylation status of the promoter region of RASSEIA in primary lung and breast cancers, the inventors used methylation-specific PCR analysis. Genomic DNA from a large number of primary resected NSCLCs, paired lung tissues resected from the same patients but not involved with the cancer, primary resected breast cancers, and a large panel of lung and breast cancer cell lines were treated with sodium bisulfite and tested for the presence of methylated and unmethylated CpG dinucleotides in the promoter region of 123F2 (RASSF1A) (FIG. 15). All of the primary resected NSCLCs and non-tumor-paired samples contained unmethylated promoter sequences, which were expected because these resected tumors were not microdissected and were contaminated with stromal cells. However, 32 (30%) of 107 primary NSCLCs, 47 (100%) of 47 SCLC lines, and 19(49%) of 39 primary breast cancers exhibited the methylated RASSFIA allele (FIG. 15; Table 7). By contrast, no methylated alleles were detected in 104 paired resected nonmalignant lung tissues (FIG. 15; Table 7).

TABLE 7

Frequency of methylation-specific polymerase chain reaction assay for detection of RASSF1A CpU island-methylated alleles in lung and breast cancers

| DNA sample source* | No. tested | No. of methylation alleles (positive) (%) |
|---|---|---|
| Primary resected NSCLCs | 107 | 32 (30%) |
| Corresponding nonmalignant lung | 104 | 0 (0%) |
| NSCLC lines | 27 | 17 (63%) |
| SCLC lines | 47 | 47 (100%) |
| Primary resected breast cancers | 39 | 19 (49%) |
| Breast cancer lines | 22 | 14 (64%) |

*NSCLC = non-small-cell lung carcinoma; SCLC = small-cell lung carcinoma.

The inventors found a high frequency of methylated 123F2 (RASSF1A) alleles in the panel of lung and breast cell cancer lines (Table 7). Because the lung and breast cancer cell lines represent essentially clonal populations of cancer cells without contaminating normal cells the inventors tabulated the frequency of the methylated and unmethylated 123F2 (RASSF1A) alleles (Table 8). While the lung and breast cancer lines often derive from clinically more aggressive lesions than the average population of tumors', the inventors previous studies[350, 351] have shown that cancer cell lines continue to retain the genetic alterations found in the uncultured cancer specimens from which they were derived. The presence of only the methylated allele is consistent with either the methylation of both parental alleles or the retention of the methylated allele and the loss of the unmethylated 3p allele. All of the SCLC cell lines howed only the methylated allele or lacked 123F2 (RASSF1A) entirely because of a homozygous deletion, consistent with the nearly universal 3p21.3 allele loss in SCLC[341, 350, 356]. Of the NSCLC cell lines, 13 (48%) of 27 (Table 8) had only the methylated 123F2 (RASSF1A) allele, and 10 (37%) of 27 had only the unmethylated allele, Consistent with a lower rate of 3p21.3 allele loss in this tumor type[341]. Likewise, 10 (45%) of 22 samples (Table 8) of breast cancer cell lines had only the methylated allele, and seven (32%) of 22 had only the unmethylated allele, again consistent with the rate of 3p21.3 allele loss found in breast cancer[351]. As expected, two tumor lines shown previously to have homozygous deletions involving the 3p21.3 region were negative for both the methylated and the unmethylated allele (Table 8)[346, 347].

TABLE 8

Presence of methylated and unmethylated RASSF1A alleles in 97 lung and breast cancer cell lines*

| RASSF1A CpG genotype | | | | | |
|---|---|---|---|---|---|
| Methylated allele | Unmethylated allele | SCLC | NSCLC | BCCL | Total |
| + | + | 0 | 4 | 4 | 8 |
| + | − | 47 | 13 | 10 | 70 |
| − | + | 0 | 10 | 7 | 17 |
| − | − | 1 | 0 | 1 | 2† |
| Total | | 48 | 27 | 22 | 97 |

*SCLC = small-cell lung cancer; NSCLC = non-small-cell lung cancer; BCCL = breast cancer cell lines.
†The two tumor cell lines with methylation-specific polymerase chain reaction genotypes lacking both methylated and unmethylated alleles (SCLC line NCIH740 and breast cancer line 11CC 1500) were known to have homozygous deletions including the RASSF1 locus in chromosome region 3p21.3.

For a subset of 61 lung and breast cancer cell lines, the inventors performed both expression and methylation analysis and found a statistically significant association (P<0.001, Fisher's exact test) between the presence of methylated RASSF1A alleles and the loss of 123F2 (RASSF1A) expression. In 12 samples, 123F2 (RASSF1A) was expressed in the absence of a methylated allele; in 44 samples, 123F2 (RASSF1A) was not expressed in the presence of a methylated allele; in four samples, 123F2 (RASSF1A) was not expressed in the absence of methylated allele; and in one sample (a breast cancer cell line), 123F2 (RASSF1A) was expressed in the presence of both a methylated and an unmethylated allele. These data show the critical association of 123F2 (RASSF1A) methylation with loss of 123F2 (RASSF1A) expression.

The inventors next assessed whether there was any association between 123F2 (RASSF1A) promoter methylation and clinical findings in the patients with primary NSCLC. The inventors found no statistically significant association between 123F2 (RASSF1A) methylation and age, sex, tumor-node-metastasis (TNM) pathologic stage, or tumor histology in 107 resected NSCLCs. In addition, the inventors found no statistically significant association between 123F2 (RASSF1A) methylation and age, TNM pathologic stage, tumor histology, estrogen or progesterone receptor status, or HER2/Neu expression in 39 primary resected breast cancers.

Survival among lung cancer patients differed by the methylation status of 123F2 (RASSF1A) (P=0.046) (FIG. 16). Also, by univariate analysis, in this group of 107 patients with NSCLC treated with an attempt at curative surgical resection, tumor (T1, T2, and T3), lymph node stage (N1 and N2), and reported weight loss were statistically significant predictors of adverse survival. Neither smoking history (yes/no or pack-years with 40 pack-year cutoff) nor treatment differences (all patients had surgical resection of lobectomy or pneumonectomy, and only five had prior radiotherapy or chemotherapy) accounted for the adverse survival. Because a multivariate analysis is of limited use with a small sample size, the inventors performed a Cox proportional hazards regression analysis by use of 123F2 (RASSF1A) methylation and the main univariate factors (tumor, lymph node stage, and weight loss). 123F2 (RASSF1A) methylation was not found to be an independent prognostic factor of survival. However, this result could be due to small numbers because even lymph node stage (a known prognostic factor) was also no longer an independent factor in the analysis.

V. Effect of Exogenous Expression of 123F2 (RASSF1A) on Tumor Cell Phenotype

The inventors examined the effect of RASSF1A on the tumor cell phenotype by three methods. The inventors used anchorage-dependent colony formation as a measure of proliferation and anchorage-independent colony formation as a measure of malignant potential. The inventors also directly assessed in vivo tumor formation.

The in vitro growth characteristics of NSCLC NCI-H 1299 clones that express RASSF1A were tested for anchorage-dependent and anchorage-independent (soft agar) growth. After 48 hours of growth in nonselective medium, transiently transfected NSCLC NCI-H 1299 cells were detached with trypsin and diluted, usually 10- to 25-fold, in complete-medium containing 800 µg/mL of G418 and plated into fresh 100-mm dishes. The medium was changed twice weekly. After 14 days, the medium was removed, the plates were washed with phosphate-buffered saline (PBS), and the colonies were stained with 1% methylene blue in 50% (vol/vol) ethanol. For the anchorage-independent, soft agar-growth assays, 1000 RASSF1A-expressing cells were suspended and plated in 0.33% Noble agar (Sigma Chemical Co. St. Louis, Mo.) in complete medium supplemented with 600 μg/mL G418 and layered over a 0.50% agar base in complete medium. After 21 days, colonies greater than 0.2 mm in diameter were counted.

For retrovirally infected cells, anchorage-independent growth assays were performed as follows: 10000 viable selected cells from each infection were plated in 0.33% soft agar over a 0.50% agar base in Dulbecco's modified Eagle medium (Life Technologies, Inc.) with 10% heat-inactivated fetal bovine serum. After 21 days, colonies greater than 0.2 mm in diameter were counted.

The inventors also tested the ability of RASSFIA-infected cells to grow in vivo in nude mice. Male BALB/c nude (nu/nu) 3- to 6-week-old mice were irradiated on day 0 of the experiment in groups of five animals by a 5-minute exposure to 350 cGy from a cesium source. The next day, each mouse was given an injection subcutaneously on its flank with 0.2 mL of sterile PBS containing $10^7$ viable parental, vector control, or RASSF1A retroviral-infected NSCLC NCI-H1299 tumor cells. Mice were monitored every 2-3 days for tumor size; once tumors reached greater than 1500 mm$^3$, the mice were killed.

The inventors first cloned RASSF1A cDNA into pcDNA3.1+, an expression vector that contains a selectable marker, and transfected NCI-H1299 cells, which lack endogenous 123F2 (RASSF1A) expression. After selection for 14-21 days, the inventors determined colony formation of NCI-H1299 cells in both anchorage-dependent and anchorage-independent assays. Expression of 123F2 (RASSF1A) in NCI-H 1299 cells resulted in a 40%-60% decrease in anchorage-dependent colony formation and in an approximate 90% decrease in anchorage-independent colony formation compared with cells transfected with the pcDNA3. 1 vector alone (FIG. 17, A). Because NCI-H1299 cells have an intragenic p53 homozygous deletion, transient expression of wild-type p53 can serve as a positive control for growth inhibition. Indeed, expression of wild-type p53 in NCI-H 1299 cells resulted in a 80% and 95% reduction in colony formation in anchorage-dependent and anchorage-independent assays, respectively (F1G. 17, A). Several clones of NCI-H1299 cells transfected with 123F2 (RASSF1A) were isolated in selective medium and were found to express 123F2 (RASSF1A) by northern blot analysis (FIG. 17, B). Although the clones grew well in vitro, each had reduced anchorage-independent colony formation by approximately 90% compared with the vector-transfected control clones (FIG. 17, C).

To eliminate the possibility that the pcDNA3.1+ vector mediated the growth-suppression effects, the inventors infected NCI-H 1299 cells with retroviral-expression vectors containing 123F2 (RASSF1A) or RASSF1C and tested the ability of these cells to grow in an anchorage-independent manner. Cells expressing 123F2 (RASSF1A) had a marked reduction in the ability to form soft-agar colonies compared with cells infected with the retroviral empty vector or the retroviral vector containing RASSF1C (FIG. 17, D). Cells expressing the retroviral vector formed 3200 colonies per 10000 cells plated. 123F2 (RASSF1A)-expressing cells formed only 19% of the vector control colonies, while RASSF1C formed 108% of the vector control. RASSF1A- and RASSFIC-infected cells grew well in vitro and showed no signs of toxicity or apoptosis.

Finally, the inventors tested the ability of the retrovirally infected NCIH1299 cells to form tumors in nude mice. Cells transfected with the vector (parental cells) formed tumors rapidly (FIG. 17, E). By contrast, cells infected with 123F2 (RASSF1A) retroviral vector and expressing the 123F2 (RASSF1A) protein had much lower tumorigenicity in vivo (FIG. 17, E).

Example 16. Several Genes in the Human Chromosome 3p21.3 Homozygous Deletion Region Exhibit Tumor Suppressor Activities In Vitro and In Vivo I. Effects of Forced Expression of 3p Genes on Tumor Cell Growth.

To test the hypothesis that one or more of the 3p genes function as tumor suppressors in vitro, the inventors performed a series of experiments to study the effects of expression of the 3p21.3 genes on cell proliferation in several types of Ad-3p-transduced human NSCLC cells and a normal HBEC line. Cells in each line were transduced in vitro by Ad-101F6, Ad-FUS1, Ad-NPRL2, Ad-BLU, Ad-RASSF1, Ad-HYAL2 and Ad-HYAL1 vectors at various MOIs in units of vp/c; cells were treated with PBS, Ad-EV, Ad-LacZ, or Ad-p53 as mock, negative, non-specific, or positive controls, respectively. The transduction efficiency was determined by examining GFP-expressing cells in the Ad-GFP-transduced cell population under a fluorescence microscope and was found to be greater than 80% at the highest MOI applied for each cell line.

Cell proliferation was analyzed by using the XTT assay to determine the number of viable cells remained at 1, 2, 3, and 5 days after transduction {only data for day 5 at highest MOIs (5000 vp/c for A549, 1000 vp/c for H1299, 5000 vp/c for H460, 2500 vp/c for H358, and 1000 vp/c for HBE, respectively) are shown} (FIG. 19). In all cases, the viability of transduced cells was compared with that of untransduced (PBS-treated) control cells (whose viability was set at 100%). As can be seen in FIG. 22, cell viability was significantly reduced in Ad-101F6-, Ad-Fus1-, and Ad-NPRL2-transduced A549 and H460 cells, which show homozygousity for multiple 3p21.3 markers and contain wild-type p. 53, and H1299 cells, which exhibit 3p21.3 homozygous but also have a homozygous deletion of p53. A modest reduction of cell viability was shown in Ad-RASSF1C-transduced H1299 cells. However, no significant effect on growth was observed in any of these cells transduced with Ad-HYAL1, Ad-HYAL2, Ad-BLU, Ad-EV or Ad-LacZ. These results suggest that exogenous expression of some wild-type 3p21.3 genes could inhibit 3p-deficient tumor cell growth or restore the tumor suppressor function of these 3p21.3 genes in vitro.

To clarify the specificity of the observed inhibitory effects on tumor cell growth and examine the potential cytotoxicity of the exogenously expressed 3p21.3 genes on normal cells, the inventors analyzed the effects of these 3p21.3 genes on cell proliferation in 3p21.3 heterozygous H358 cells and normal HBECs (FIG. 19). As shown in FIG. 19, HBECs transduced with all Ad-3p genes at highest MOIs had losses of cell viability of less than 10%, while H358 cells transduced with the same vectors had losses of cell viability less than 20% when compared with the untransduced control cells. Similar levels of losses of cell numbers were observed in H358 and HBEC cells transduced with Ad-EV and Ad-LacZ. H358 cells which are deleted for p53 showed reduced cell viability when transduced with the Ad-p53 control. These results couple with the lack of effect with Ad-LacZ, Ad-HYAL2, Ad-HYAL1, Ad-RASSF1, and Ad-BLU, demonstrate the specificity of the tumor-suppressing function of 3p21.3 genes, FUS1, NPRL2, 101F6 in 3p-deficient tumor cells and indicate that no generalized cytotoxicity was associated with exogenous expression of these wild-type 3p21.3 genes.

Expression of 3p21.3 genes in Ad-3p transfectants was verified by quantitative real-time RT-PCR, and known concentrations of human total RNA and primers and TaqMan probe for β-actin DNA and for GAPDH cDNA were used as standards and internal controls, respectively (FIG. 20). The transcription of FUS1 (FIG. 20A), 101F6 (FIG. 20B), NPRL2 (FIG. 20C), and HYAL1 (FIG. 20D) was demonstrated quantitatively by showing the association between increased levels of expression of these 3p21.3 genes with increased MOIs of the corresponding Ad-3p vectors in transduced 111299 cells. The transcription of other 3p21.3 genes, HYAL2, HYAL1, BLU, and RASSF1, was also detected by real-time RT-PCR. The expression of FUS1 and 101F6 proteins was detected also by western blot analysis using available polyclonal antibodies raised against the oligopeptides derived from their deduced amino acid sequences.

II. Induction of Apoptosis by 3p Genes in Ad-3p-Transduced Tumor Cells.

The ability of exogenously expressed 3p21.3 genes to induce apoptosis in the Ad-3p-transduced H1299, A549, H460, H358, and HBEC cells was analyzed by FACS using the TUNEL reaction (FIG. 21). Induction of apoptosis was detected in Ad-101F6-, Ad-FUS1-, and Ad-NPRL2-transduced A549 (FIG. 21A), H1299 (FIG. 21B), and H460 (FIG. 21C) cells, but not in H358 (FIG. 21D) and HBEC (FIG. 21E) cells. The apoptotic cell populations increased with increased duration of transduction; more than 15-20%, 40-65%, and 75% of cells were apoptotic 5 days after transduction with Ad-101F6, Ad-FUS1, and Ad-NPRL2 in the transduced H1299, A549, and H460 cells, respectively, whereas only about 7% and 10% of cells treated with PBS alone and transduced with Ad-EV vector, respectively, were TUNEL-positive after the same time interval. The levels of apoptosis induction by Ad-101F6, Ad-FUS1, and Ad-NPRL2 appeared 20-50% more significant in A549 and H460 cell lines with wild-type p53 genes (FIGS. 21A and 21C) than that in H1299 cell line deleted for p53 gene (FIG. 21B). Levels of apoptosis in A549 and H460 cells were comparable to those induced by Ad-p53 in p53-deficient H1299 and H358 cells (FIGS. 21B and D). However, no significant induction of apoptosis was observed in any tumor cell line transduced by Ad-BLU, Ad-RASSF1, Ad-HYAL2, and Ad-HYAL1 (FIG. 21). The levels and time of induction of apoptosis in cells transduced by these Ad-3p vectors were well correlated with those of cell proliferation inhibition in cells treated with the same vectors (FIG. 19), suggesting that suppression of tumor cell proliferation by 3p21.3 genes is mediated directly or indirectly through a mechanism of apoptosis induction.

III. Suppression of Tumor Growth by Intratumoral Injection of Ad-3p Vectors.

To determine whether the observed inhibitory effects of these 3p21.3 genes on tumor cell proliferation in vitro could be demonstrated on tumor growth in vivo, the inventors evaluated the efficacy of 3p21.3 genes in suppressing tumor growth by direct intratumoral injection of Ad-3p21.3 gene vectors, along with PBS and Ad-EV, Ad-LacZ, and Ad-p53 vectors as controls, into A549 or H1299 tumor xenografts in nu/nu mice (FIG. 22). The growth of tumors was recorded from the first injection until 20 days after the last injection. Tumor volumes were normalized by calculating the percentage increase in tumor volume after treatment relative to volume at the beginning of treatment in each group. In both A549 (FIG. 22A) and H1299 (FIG. 22B) tumor models, all of the tumors treated with Ad-101F6, Ad-FUS1, or Ad-NPRL2 showed significantly suppressed growth (P<0.001), compared with mouse groups treated with Ad-LacZ or Ad-EV controls, whereas no significant effect was observed in Ad-BLU, Ad-RASSF1, and Ad-HYAL1-treated tumors. H1299 A549 tumor xenografts but not A549 H1299 tumors treated with Ad-HYAL2 showed significant reduction only at the end points of treatment (P=0.036). Moreover, a significantly stronger inhibition of tumor growth was shown in A549 tumors treated with Ad-101F6 and Ad-NPRL2 vectors than in tumors treated with the Ad-p53 vector (FIG. 22A).

IV. Inhibition of Development of Experimental Lung Metastases by Protamine-Adenovirus Complex-Mediated 3p21.3 Gene Transfer.

A novel formulation using protamine/adenovirus complexes (designated P-Ad) for enhanced systemic delivery of recombinant adenovirus in vivo was developed to further explore the potential of 3p21.3 genes in suppressing systemic metastases. An experimental A549 metastatic human lung cancer model was used to study the effects of 3p21.3 gene transfer on the development of lung metastases in nu/nu mice (FIG. 23). The adenoviral 3p21.3 gene vectors were complexed to protamine and delivered via intravenous injection. The development of A549 metastases was significantly inhibited and the formation of metastatic tumor colonies on the surfaces of lungs from mice inoculated with A549 was reduced more than 80% in animals treated with P-Ad-101F6, P-Ad-FUS1, P-Ad-NPRL2, P-Ad-BLU or P-Ad-HYAL2 compared with those in control treatment groups (FIG. 23A). However, no significant reduction of metastatic colony formation was observed in animals treated with P-Ad-HYAL1 and P-Ad-RASSF1P-Ad-BLU. These data are consistent with results obtained from Ad-3p-treated subcutaneous tumors, further supporting the roles of these 3p21.3 genes in suppression of tumor growth and inhibition of tumor progression in vivo.

Example 17. Overexpression of Candidate Tumor Suppressor Gene FUS1 Isolated from the 3p21.3 Homozygous Deletion Region Leads to G1 Arrest and Growth Inhibition of Lung Cancer Cells Very frequent loss of one allele of chromosome arm 3p in both small lung cancer (SCLC) and non-small cell lung cancer (NSCLC) provides strong evidence for the existence of tumor suppressor genes (TSGs) in this chromosome region[363; 364; 367; 371; 372]. Multiple different 3p regions showing isolated allele loss were identified by detailed allelotyping studies suggesting there are several different TSGs located on 3p suggesting there are several different TSGs located on 3p[361; 362; 372]. Nested homozygous deletions in lung cancer and breast cancer cell lines have been found at 3p21.3 that focused our search on a 630 kb region including the identification, annotation, and evaluation of 25 new genes as TSG candidates[357; 365; 366; 368; 369; 370]. A breast cancer deletion narrowed this region further to 120 kb and 9 TSG candidates (CACNA2D2, PL6, 106F6, NPRL2/g21, BLU, RASSF1, FUS1, HYAL2, HYAL1) were located in or bordering this region[369]. One of these candidate TSGs, FUS1 (AF055479), did not show homology with any known genes, was found to have only few mutations in lung cancers, and usually was expressed at the mRNA level in lung cancers[366]. Several NSCLCs (NCI-H322 and NCI-H1334) exhibited the same nonsense mutation, which arose from aberrant mRNA splicing. This aberrant form lacked 28 bp of mRNA at the 3' terminus of FUS1 exon 2 resulting in a truncated predicted protein of 82 amino acids compared to 110 amino acids in the wild-type (FIG. 24). To confirm the inventors mutational analysis, which previously had been conducted on lung cancer cell line DNAs, they searched for other mutations in FUS1 in primary uncultured lung cancers. Single strand conformation polymorphism (SSCP) analysis was performed using genomic DNA of 40 primary uncultured lung cancers (9 SCLCs and 31 NSCLCs) (FIG. 24)[360]. No mutations were detected although the inventors found a single nucleotide polymorphism in intron 2 that did not alter the amino acid sequence of FUS1.

The inventors next considered CpG island promoter region methylation as an epigenetic mechanism leading to TSG inactivation. In fact, such tumor acquired promoter region methylation was found to occur for the RASSF1A mRNA isoform residing immediately centromeric to FUS1[354; 358]. However, FUS1 mRNA was expressed in most lung cancers making such CpG methylation an unlikely method of inactivation of FUS1[366]. In addition, the 5' putative promoter region containing CpG islands of FUS1 was sequenced using sodium bisulfite treated[355] DNA from 6 lung cancers were the inventors did not detect FUS1 protein expression and found no CpG methylation.

The possibility of haploinsufficiency or reduced expression of FUS1 was considered as another mechanism for this gene to participate in lung cancer pathogenesis[356; 359; 373]. The inventors first performed western blot analysis of a panel of lung cancer cell lines using an anti-Fus1 anti peptide antibody which readily detected exogenously expressed Fus1 (FIG. 25) but could not detect any endogenous FUS1 expression in lung cancers (FIG. 25 for H1299 NSCLC given as an example of negative data). This lack of detection could be due to a variety of factors including the quality of the antibodies. Nevertheless, if loss or low levels of FUS1 protein expression was involved in lung cancer pathogenesis the inventors reasoned that exogenous introduction and expression of Fus1 might suppress the malignant phenotype. Colony formation assays were performed after transfection of FUS1 expression vectors. The inventors made a C terminal FLAG-tagged FUS1 construct by PCR and ligated it into expression vector pcDNA3.1 (Invitrogen, Carlsbad Calif.). Empty vector and an expression vector containing wild-type FUS1, FLAG-tagged FUS1, and the 82 aa mutant FUS1 were was transfected into NSCLC NCI-H129.9 cells which has suffered allele loss for the 3p21.3 630 kb region and does not express detectable FUS1 protein (FIG. 25), and NSCLC NCI-H322 cells containing a expressing the endogenoushomozygous nonsense truncation mutation of FUS1 1 and also not expressing detectable FUS1 protein. Expression of the FUS1 constructs in H1299 cells after transient transfection was confirmed by Western blot analysis using anti-Flag and anti-N terminal FUS1 antibodies (FIG. 25). The effect of FUS1 transfection with a neo resistance gene on lung cancer colony formation was tested. The numbers of G418 resistant colonies in the FUS1 transfections were dramatically reduced in comparison with transfection with the empty vector (FIG. 25). By contrast, the number of colonies formed in the mutant FUS1 transfectants was only slightly reduced, suggesting that this lung cancer-associated mutant FUS1 was functionally inactive (FIG. 25).

An ecdysone inducible mammalian expression system in H1299 cells was developed to confirm that overexpression of FUS1 could inhibit tumor cell growth. In this system, FUS1 expression is induced in the presence of Ponasterone A. H1299 parent ECR9 cells with the regulatable hormone receptor vector pVgRXR alone served as an additional control. H1299 ECR9 cells were transfected with pINDsp1-FUS1-FLAG(neo), selected with G418 in the presence or absence of Ponasterone A, and compared the numbers of G418 resistant colonies. The number of colonies formed in cells with induced expression of in the FUS1 induced condition was decreased an average of 75±8% compared with number of colonies in cells under the uninduced condition, providing another confirming action of the growth inhibitory activity of FUS1. Twenty stable G418 resistant clones were isolated in the uninduced condition and, the inducible expression of FUS1-FLAG was examined. Among them, 6 clones showed some FUS1 induction and two stable clones were selected (Cl.13 and Cl.16) in which expression of FUS1-Flag was clearly inducible by Ponasterone A (FIG. 26). However, both cell lines expressed some FUS1 in the uninduced condition, indicating that regulation of FUS1 expression was leaky.

The cell growth rate was examined in induced and uninduced conditions by the MTT assay. Ponasterone A has no effect on the growth of parental cell line H1299 ECR 9 cells, but the growth of Cl. 13 and Cl. 16 cells were inhibited in the presence of Ponasterone A (FIG. 26). The induction of Fus1 expression and inhibition of tumor cell growth appeared to be dependent on the dose of Ponasterone A both increasing with the increased concentrations of Ponasterone A (FIG. 26). With Fus1 induction, the doubling times of the tumor cells were also increased in both clones, from 22 to 46 hrs for Cl. 13 and from 21 to 45 hrs for Cl.16, respectively. These results also indicated that overexpression of Fus1 suppresses H1299 lung cancer cell growth in vitro.

An increase of apoptosis in H1299 cells under induced condition by TUNEL assay was not observed. However, when cells were induced by Ponasterone A to express Fus1 for 48 hrs and analyzed by fluorescent activated cell sorter (FACS) analysis (see legend of FIG. 26 for details) by FACS analysis the inventors found: parental H1299-ECR9 cells to have unchanged cell cycle parameters (G1 51%, S 18%, G2/M 31% uninduced and G1 50%, S 18%, G2/M 32% induced); while Fus1 induced clones showed G1 arrest (H1299 clone13 showed G1 50%, S 17%, G2/M 33% uninduced and G1 65%, S 10%, G2/M 25% induced; and H1299 clone16 G1 56%, S 16%, G2/M 28% uninduced and G1 65%, S 12%, G2/M 23% induced). The increase in G1% was significant (P<0.05, students t test). These results suggest of cell cycle analysis showed that overexpression of FUS1 in H1299 cells is associated with G1 arrest and alteration of cell cycle kinetics.

Lung cancer cell lines do not express detectable endogenous levels of Fus1 protein, and exogenous introduction of Fus1 with overexpression inhibited lung cancer cell growth in vitro. This growth inhibition was seen in a lung cancer line suffering allele loss for the region and in another carrying a homozygous truncating mutation of FUS1. In addition, the inventors found that this truncated Fus1 protein had lost tumor growth suppressing activity. Besides the acute transfection studies, the inventors established, a Fus1 inducible system and showed that tumor growth inhibition was correlated with the level of expression of Fus1 protein. In addition, cell cycle analysis using the same expression-regulatable system showed that the mechanism for the inhibition of cell growth was associated with G1 arrest and not with induction of apoptosis. Finally, the inventors confirmed that somatic mutation of FUS1 was rare in primary lung cancers (0/40), in agreement with previous studies which showed 3/79 lung cancers with alterations in the FUS1 gene (2 nonsense mutations and 1 deletion). In fact the frequency of mutation in any of the 22 out of 25 candidate genes the inventors have studied in detail in this 600 kb 3p21.3 region is low compared to the high frequency LOH at this locus. One possibility to account for the low mutation frequency is loss of expression of FUS1 or other of the 3p21.3 genes by tumor promoter acquired methylation. The expression of RASSF1A mRNA isoform isolated from the same 3p21.3 deletion region and 15.5 kb centromeric of FUS1 was repressed in many lung cancers by acquired CpG island promoter DNA methylation for this gene[354; 358]. Replacement of RASSF1A inhibited tumor cell growth in vitro and in vivo indicating RASSF1A is another candidate tumor suppresser gene in this locus. However the inventors have not found loss of FUS1 mRNA expression[366] or 5' region CpG methylation for FUS1 in lung cancers thus excluding tumor acquired promoter methylation as an inactivating mechanism for the FUS1 gene. FUS1 may act as haploinsufficient tumor suppressor gene[356]. The inventors experiments showed that overexpression of FUS1 caused G1 arrest in H1299. Although some signal or environmental cue may induce the expression of Fus1 and lead to G1 arrest in normal cells, 3p allelic loss and some other alteration of FUS1 in malignant cells may lead to haploinsufficiency and/or loss of expression of FUS1 in lung tumors and escape from cell cycle arrest.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

1. Roth J A. Gene replacement strategies for lung cancer. Curr Opin Oncol 1998; 10:127-132.
2. Roth J A. Restoration of tumour suppressor gene expression for cancer. Forum 1998; 8:368-376.
3. Chengalvala M V, Lubeck M D, Selling B J, et al. Adenovirus vectors for gene expression. Curr. Opin. Biotechnol. 1991; 2:718-722.
4. Adams D H, Hubscher S G, Fisher N C, Williams A, Robinson M. Expression of E-selectin and E-selectin ligands in human liver inflammation. Hepatol 1996; 24:533-8.
5. Ji L, Fang B, Yen N, Fong K, Minna J D, Roth J A. Induction of apoptosis and inhibition of tumorigenicity and tumor growth by adenovirus vector-mediated fragile histidine triad (FHIT) gene overexpression. Cancer Res. 1999; 59:3333-3339.
6. Sekido Y, Fong K M, Minna J D. Progress in understanding the molecular pathogenesis of human lung cancer. Biochimica Biophysica Acta 1998; 1378:F21-F59
7. Virmani A K, Fong K M, Kodagoda D, McIntire D, Hung J, Tonk V, et al. Allelotyping demonstrates common and distinct patterns of chromosomal loss in human lung cancer types. Genes, Chrom Cancer 1998; 21:308-319.
8. Gazdar A F, Bader S, Hung J, Kishimoto. Y, Sekido Y, Sugio K, et al. Molecular genetic changes found in human lung cancer and its precursor lesions. Cold Spring Harbor Sym Quant Biol 1994; 59:565-572.
9. Minna J D. Summary of the role of dominant and recessive oncogenes in the pathogenesis of lung cancer and the application of this knowledge in translational research. In: Pass H, Mitchell 3, Johnson D, Turrisi A, editors. Summary of the role of dominant and recessive oncogenes in the pathogenesis of lung cancer and the application of this knowledge in translational research. Philadelphia: JB Lippincott Co., 1994:
10. Minna J D, Sekido Y, Fong K, Gazdar AF. Molecular Biology of Lung Cancer. In: DeVita V T, Jr., Hellman S, Rosenberg S A, editors. Cancer: Principles and Practice of Oncology. 5 ed. Philadelphia: Lippincott, 1997:849-857.
11. Daly M C, Xiang R H, Buchhagen D, Hensel C H, Garcia D K, Killary A M, et al. A homozygous deletion on chromosome 3 in a small cell lung cancer cell line correlates with a region of tumor suppressor activity. Oncogene 1993; 8:1721-1729.
12. Bermes M, Casadevall C, Miro R, Caballin M R, Gelabert A, Ejarque M J, et al. Analysis of 3p allelic losses in renal cell carcinomas: Comparison with cytogenetic results. Cancer Genet Cytogenet 1998; 107:121-124.
13. Thar B, Brauch H, Talmadge C, Linehan M. Loss of alleles of loci on the short arm of chromosome 3 in renal cell carcinoma. Nature 1987; 327:721-724.
14. Gazdar A F, Kurvari V, Virmani A, Gollahon L, Sakaguchi M, Westerfield M, et al. Characterization of paired tumor and non-tumor cell lines established from patients with breast cancer. Internatl J Cancer 1998; 78:766-774.
15. Sekido Y, Ahmadian M, Wistuba I I, Latif F, Bader S, Wei M H, et al. Cloning of a breast cancer homozygous deletion junction narrows the region of search for a 3p21.3 tumor suppressor gene. Oncogene 1998; 16:3151-3157.
16. Buchhagen D L, Worsham M J, Dyke D L, Carey T E. Two regions of homozygosity on chromosome 3p in squamous cell carcinoma of the head and neck: comparison with cytogenetic analysis. Head & Neck 1996; 18:529-537.
17. Gorunova L, Hoglund M, Andren-Sandberg A, Dawiskiba S, Jin Y S, Mitelman, et al. Cytogenetic analysis of pancreatic carcinomas: Intratumor heterogeneity and nonrandom pattern of chromosome aberrations. Genes Chrom Cancer 1998; 23:81-99.
18. Hughson M D, Dickman K, Bigler S A, Meloni A M, Sandberg A A. Clear-cell and papillary carcinoma of the kidney: An analysis of chromosome 3, 7, and 17 abnormalities by microsatellite amplification, cytogenetics, and fluorescence in situ hybridization. Cancer Genet Cytogenet 1998; 106:93-104.
19. Uzawa N, Yoshida M A, Hosoe S, Oshimura M, Amagasa T, Ikeuchi T. Functional evidence for involvement of multiple putative tumor suppressor genes on the short arm of chromosome 3 in human oral squamous cell carcinogenesis. Cancer Genet Cytogenet 1998; 107:125-131.
20. Kersemaekers A M, Kenter G G, Hermans J, Fleuren G J, van d, V. Allelic loss and prognosis in carcinoma of the uterine cervix. Internatl J Cancer 1998; 79:411-417.
21. Wistuba I I, Montellano F D, Milchgrub S, Virmani A K, Behrens C, Chen H, et al. Deletions of chromosome 3p are frequent and early events in the pathogenesis of uterine cervical carcinoma. Cancer Res 1997; 57:3154-3158.
22. Hung J, Kishimoto Y, Sugio K, Virmani A, McIntire D D, Minna J D, et al. Allele-specific chromosome 3p deletions occur at an early stage in the pathogenesis of lung carcinoma. JAMA 1995; 273:1908
23. Sekido Y, Bader S, Latif F, Chen T Y, Duh F M, Wei M H, et al. Human semaphorins A(V) and IV reside in the 3p21.3 small cell lung cancer deletion region and demonstrate distinct expression patterns. Proc Natl Acad Sci, U.S.A 1996; 93:4120-4125.
24. Wistuba I I, Behrens C, Milchgrub S, Bryant D, Hung J, Minna J D, et al. Sequential molecular abnormalities are involved in the multistage development of squamous cell lung carcinoma. Oncogene 1999; 18:643-650.
25. Kohno H, Hiroshima K, Toyozaki T, Fujisawa T, Ohwada H. p53 mutation and allelic loss of chromosome 3p, 9p of preneoplastic lesions in patients with nonsmall cell lung carcinoma. Cancer 1999; 85:341-347.
26. Wistuba I I, Behrens C, Virmani A K, Milchgrub S, Syed S, Lam S, et al. Allelic losses at chromosome 8p21-23 are early and frequent events in the pathogenesis of lung cancer. Cancer Res 1999; 59:1973-1979.
27. van den Berg A, Dijkhuizen T, Draaijers T G, Hulsbeek M M, Maher E R, van, et al. Analysis of multiple renal cell adenomas and carcinomas suggests allelic loss at 3p21 to be a prerequisite for malignant development. Genes Chrom Cancer 1997; 19:228-232.
28. Shay J W. Telomerase in human development and cancer, J Cell Physiol 1997; 173:266-270.
29. Shay J W. Telomerase in cancer: diagnostic, prognostic, and therapeutic implications. Cancer J Sci American 1998; 4 Suppl 1:S26-S34
30. Sanchez Y, El-Naggar A, Pathak S, Killary A M. A tumor suppressor locus within 3p14-p12 mediates rapid cell death of renal cell carcinoma in vivo. Proc Natl Acad Sci, U.S.A. 1994; 91:3383-3387.
31. Wu X, Zhao Y, Honn S E, Tomlinson G E, Minna J D, Hong W K, et al. Benzo[a]pyrene diol epoxide-induced 3p21.3 aberrations and genetic predisposition to lung cancer. Cancer Res 1998; 58:1605-1608.
32. Pellegata N S, Ranzani G N. The significance of p53 mutations in human cancers. Eur J Histochem 1996; 40:273-282.
33. Polyak K, Waldman T, He T C, Kinzler K W, Vogelstein B. Genetic determinants of p53-induced apoptosis and growth arrest. Genes Devel 1996; 10:
34. Wang X W, Harris C C. Tp53 tumour suppressor gene-clues to molecular carcinogenesis and cancer therapy. Cancer Sury 1996; 28:169-196.
35. Quigley J P, Armstrong P B. Tumor cell intravasation alu-cidated: the chick embryo opens the window. Cell 1998; 94:281-284.
36. Killary A M, Wolf M E, Giambernardi T A, Naylor S L. Definition of a tumor suppressor locus within human chromosome 3p21-p22. Proc Natl Acad Sci, U.S.A. 1992; 89:10877-10881.
37. Killary A M, Fournier R E. Microcell fusion. Methods in Enzymology 1995; 254:133-152.
38. Satoh H, Lamb P W, Dong J T, Everitt J, Boreiko C, Oshimura M, et al. Suppression of tumorigenicity of A549 lung adenocarcinoma cells by human chromosomes 3 and 11 introduced via microcell-mediated chromosome transfer. Mol Carcinogensis 1993; 7:157-164.
39. Berkner K L. Development of adenovirus vectors for the expression of heterologous genes. Biotech 1988; 6:616-629.
40. Bett A J, Haddara W, Prevec L, Graham F L. An efficient and flexible system for construction of adenovirus vectors with insertions or deletions in early regions 1 and 3. Proc. Natl. Acad. Sci. U.S.A. 1994; 91:8802-8806.
41. Ketner G, Spencer F, Tugendreich S, Connelly C, Hieter, P. Efficient manipulation of the human adenovirus genome as an infectious yeast artificial chromosome clone. Proc. Natl. Acad. Sci. U.S.A. 1994; 91:6186-6190.
42. Fu S, Deisseroth A B. Use of the cosmid adenoviral vector cloning system for the in vitro construction of recombinant adenoviral vectors. Human Gene Ther 1997; 8:1321-1330.
43. Chartier, C., Degryse, E., Gantzer, M., Dieterle, A., Pavloff, N., and Meier-Tackmann, D. Efficient generation of recombinant adenovirus vectors by homologous recombination in *Escherichia coli*. J. Virol. 70, 4805-4810. 1996.
44. He T C, Zhou S, da Costa L T, Yu J, Kinzler K W, Vogelstein B. A simplified system for generating recombinant adenoviruses. Proc. Natl. Acad. Sci. U.S.A. 1998; 95:2509-2514.
45. Mizuguchi H, Kay M A. Efficient construction of a recombinant adenovirus vector by an improved in vitro ligation method. Human Gene Ther 1998; 9:2577-2583.
46. Kagawa S, Pearson S A, Ji L, Xu K, McDonnell T J, Swisher S, et al. A binary adenoviral vector for expressing high levels of the proapoptotic gene bax. Gene Ther. 1999;
47. Clark P R, Stopeck A T, Brailey J L, Wang Q, McArthur J, Finer M H, et al. Polycations and cationic lipids enhance adenovirus transduction and transgene expression in tumor cells. Cancer Gene Ther 1999; 6:437-446.
48. Lanuti M, El Kouri C, Force S D, Chang M Y, Amin K, Xu K, et al. Use of protamine to augment adenovirus-mediated cancer gene therapy. Gene Ther 1999; 6:1600-1610.
49. Templeton N S, Lasic D D, Frederik P M, Strey H H, Roberts, D D, et al. Improved DNA: liposome complexes for increased systemic delivery and gene expression. Nat Biotechnol 1997; 15:647-652.
50. Li S, Rizzo M A, Bhattacharya S, Huang. L. Characterization of cationic lipid-protamine-DNA (LPD) complexes for intravenous gene delivery. Gene Ther 1998; 5:930-937.
51. Li S, Rizzo M A, Bhattacharya S, Huang L. Characterization of cationic lipid-protamine-DNA (LPD) complexes for intravenous gene delivery. Gene Ther 1998; 5:930-937.
52. Mabry M, Nelkin B D, Baylin S B. Lung Cancer in *The Genetic Basis of Human Cancer*; (Vogelstein B and Kinzler K W, eds., McGraw Hill 1998) p. 671-679.
53. Baichwal and Sugden, "Vectors for gene transfer derived from animal DNA viruses: Transient and stable expression of transferred genes", In: *Gene Transfer, Kucherlapati R, ed., New York, Plenum Press, pp.* 117-148, 1986.
54. Barany and Merrifield, The Peptides, Gross and Meienhofer, eds., Academic Press, New York, pp. 1-284, 1979.
55. Bellus, *J. Macromol. Sci. Pure Appl. Chem., A*31(1): 1355-1376, 1994.
56. Benvenisty and Neshif, "Direction introduction of genes into rats and expression of the genes", *Proc. Nat. Acad. Sci. USA,* 83:9551-9555, 1986.
57. Bishop, J. M., "Molecular themes in oncogenesis", *Cell,* 64:2351-248, 1991.

58. Boring et al., *Cancer Statistics, 1994 CA*, 43:7-26, 1994.
59. Brinster et al., *Proc. Nat'l Acad. Sci. USA*, 82: 4438-4442, 1985.
60. Capaldi et al., *Biochem. Biophys. Res. Comm.*, 76:425, 1977
61. Chang et al., "Foreign gene delivery and expression in hepatocytes using a hepatitis B virus vector", *Hepatology*, 14:124 A, 1991.
62. Chen and Okayama, "High-efficiency transfection of mammalian cells by plasmid DNA", *Mol. Cell. Biol.*, 7:2745-2752, 1987.
63. Coffin, Retroviridae and Their Replication. In: *Virology*, Fields et al., eds., Raven Press, New York, pp. 1437-1500, 1990.
64. Cohen, P., "The discovery of protein phosphatases: From chaos and confusion to an understanding of their role in cell regulation and human disease", *Bioessays*, 61-583-588, 1994.
65. Collet et al., "Protein kinase activity associated with the avian sarcoma virus src gene product", *Proc. Natl. Acad. Sci. USA*, 75:2021-2024, 1978.
66. Cook et al., "In vitro splicing of the ribosomal RNA precursor of *Tetrahymena*: involvement of a guanosine nucleotide in the excision of the intervening sequence," *Cell*, 27:487-496, 1981.
67. Couch et al., "Immunization with types 4 and 7 adenovirus by selective infection of the intestinal tract," *Am. Rev. Resp. Dis.*, 88:394-403, 1963.
68. Coupar et al., "A general method for the construction of recombinant vaccinia virus expressing multiple foreign genes", *Gene*, 68:1-10, 1988.
69. Culver et al., In vivo gene transfer with retroviral vector-producer cells for treatment of experimental brain tumors. *Science*, 256:1550-1552, 1992.
70. Daly et al., "A homozygous deletion on chromosome 3 in small cell lung cancer cell line correlates with a region of tumor suppressive activity", *Oncogene* 8:1721-1729, 1993.
71. Davey et al., EPO No. 329 822.
72. Denu et al., "Form and function in protein dephosphorylation", *Cell* 87:361-364, 1996.
73. Dubensky et al., "Direct transfection of viral and plasmid DNA into the liver or spleen of mice", *Proc. Nat. Acad. Sci. USA*, 81:7529-7533, 1984.
74. EP 329 822, Davey et al.
75. Fanning and Anderson, "Protein-protein interactions: PDZ domain networks.", *Curr Biol*, 6:(11)1385-1388, 1996.
76. Fechheimer et al., "Transfection of mammalian cells with plasmid DNA by scrape loading and sonication loading", *Proc. Natl. Acad. Sci. USA*, 84:8463-8467, 1987.
77. Ferkol et al., "Regulation of the phosphoenolpyruvate carboxykinase/human factor IX gene introduced into the livers of adult rats by receptor-mediated gene transfer", *FASEB J.*, 7:1081-1091, 1993.
78. Fodor et al., "Light-directed, spatially addressable parallel chemical synthesis", *Science*, 251:767-773, 1991.
79. Forster & Symons, "Self-cleavage of plus and minus RNAs of a virusoid and a structural model for the active sites," *Cell*, 49:211-220, 1987.
80. Foulds, The natural history of cancer. *J. Chronic Dis.*, 8:2-37, 1958.
81. Fraley et al., "Entrapment of a bacterial plasmid in phospholipid vesicles: Potential for gene transfer", *Proc. Natl. Acad. Sci. USA*, 76:3348-3352, 1979.
82. Freifelder, *Physical Biochemistry Applications to Biochemistry and Molecular Biology*, 2nd ed. Wm. Freeman and Co., New York, N.Y., 1982.
83. Freshner, Animal Cell Culture: A Practical Approach, 2nd ed., Oxford/New York, IRL Press, Oxford University Press, 1992.
84. Friedmann, "Progress toward human gene therapy", *Science*, 244:1275-1281, 1989.
85. Frohman, In: *PCR™ Protocols: A Guide To Methods And Applications*, Academic Press, N.Y., 1990.
86. Gefter et al., *Somatic Cell Genet.*, 3: 231-236, 1977.
87. Gerlach et al., "Construction of a plant disease resistance gene from the satellite RNA of tobacco rinspot virus," *Nature (London)*, 328:802-805, 1987.
88. Ghosh-Choudhury et al., *EMBO J.*, 6:1733-1739, 1987.
89. Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87-104, 1991.
90. Goding, 1986, In: *Monoclonal Antibodies: Principles and Practice*, 2d ed., Academic Press, Orlando, Fla., pp. 60-61, and 71-74, 1986.
91. Gomez-Foix et al., *J. Biol. Chem.*, 267:25129-25134, 1992.
92. Gopal, "Gene transfer method for transient gene expression, stable transfection, and cotransfection of suspension cell cultures", *Mol. Cell. Biol.*, 5:1188-1190, 1985.
93. Graham and Prevec, In: *Methods in Molecular Biology: Gene Transfer and Expression Protocol*, E. J. Murray, ed., Humana Press, Clifton, N.J., 7:109-128, 1991.
94. Graham and van der Eb, "A new technique for the assay of infectivity of human adenovirus 5 DNA", *Virology*, 52:456-467, 1973.
95. Graham et al., "Characteristics of a human cell line transformed by DNA from human adenovirus type 5", *J. Gen. Virol.*, 36:59-72, 1977.
96. Grunhaus and Horwitz, "Adenovirus as cloning vector", *Seminar in Virology*, 3:237-252, 1992.
97. Hardie and Hanks, In: The Protein Kinase Facts Book, 1995
98. Harland and Weintraub, "Translation of mammalian mRNA injected into *Xenopus* oocytes is specifically inhibited by antisense RNA", *J. Cell Biol.*, 101:1094-1099, 1985.
99. Harlow and Lane, Antibodies: A Laboratory manual, Cold Spring Harbor Laboratory, 1988.
100. Hermonat and Muzycska, "Use of adenoassociated virus as a mammalian DNA cloning vector: Transduction of neomycin resistance into mammalian tissue culture cells", *Proc. Nat. Acad. Sci. USA*, 81:6466-6470, 1984.
101. Hersdorffer et al., *DNA Cell Biol.*, 9:713-723, 1990.
102. Herz and Gerard, *Proc. Nat'l Acad. Sci. USA*, 90:2812-2816, 1993.
103. Horwich, et al., "Synthesis of hepadnavirus particles that contain replication-defective duck hepatitis B virus genomes in cultured HuH7 cells", *J. Virol.*, 64:642-650, 1990.
104. Hunter, T., "Cooperation between oncogenes", *Cell*, 64-249-270, 1991.
105. Innis et al., *PCR™ Protocols*, Academic Press, Inc., San Diego Calif., 1990.
106. Johnson et al., Peptide Turn Mimetics" IN: *Biotechnology And Pharmacy*, Pezzuto et al., eds., Chapman and Hall, New York, 1993.
107. Jones and Shenk, *Cell*, 13:181-188, 1978.

108. Kaneda et al., "Increased expression of DNA cointroduced with nuclear protein in adult rat liver", *Science*, 243:375-378, 1989.
109. Karlsson et al., *EMBO* 1, 5:2377-2385, 1986.
110. Kato et al., "Expression of hepatitis B virus surface antigen in adult rat liver", *J. Biol. Chem.*, 266:3361-3364, 1991.
111. Kim & Cook, "Three dimensional model of the active site of the self-splicing rRNA precursor or Tetrahymena," *Proc. Natl. Acad. Sci. USA*, 84:8788-8792, 1987.
112. Klein et al., "High-velocity microprojectiles for delivering nucleic acids into living cells", *Nature*, 327:70-73, 1987.
113. Kohler and Milstein, *Eur. J. Immunol.*, 6:511-519, 1976.
114. Kohler and Milstein, *Nature*, 256:495-497, 1975.
115. Kok et al., "A homozygous deletion in a small cell lung cancer cell line involving a 3p21 region with a marked instability in yeast artificial chromosomes", *Cancer Res.* 54:4183-4187, 1994.
116. Komiya et al., "Allelic losses at loci on chromosome 10 are associated with metastasis and progression of human prostate cancer", *Genes Chromo. Cancer.* 17:245-253, 1996.
117. Kruglyak, et al., "Parametric and nonparametric linkage analysis: a unified multipoint approach," *Am. J. Hum. Genet.*, 58:347-1363, 1996.
118. Kwoh et al., *Proc. Nat. Acad. Sci. USA*, 86: 1173, 1989.
119. Kyte and Doolittle, *J. Mol. Biol.*, 157(1):105-132, 1982.
120. Lathrop, et al., "Strategies for multilocus, linkage analysis in humans," *Proc. Natl. Acad. Sci. USA*, 81:3443-3446, 1984.
121. Le Gal La Salle et al., *Science*, 259:988-990, 1993.
122. Lee et al., "Human retinoblastoma susceptibility gene: cloning, identification, and sequence", *Science*, 235:1394-1399, 1987.
123. Levrero et al., *Gene*, 101:195-202, 1991.
124. Macejak and Sarnow, *Nature*, 353:90-94, 1991.
125. Manipulating the Mouse Embryo: A Laboratory Manual, 2nd ed., Hogan et al., eds., Cold Spring Harbor Laboratory Press, 1994.
126. Mann et al., "Construction of a retrovirus packaging mutant and its use to produce helper-free defective retrovirus", *Cell*, 33:153-159, 1983.
127. Markowitz et al., *J. Virol.*, 62:1120-1124, 1988.
128. Merrifield, *Science*, 232: 341-347, 1986.
129. Michel & Westhof, "Modeling of the three-dimensional architecture of group I catalytic introns based on comparative sequence analysis," *J. Mol. Biol.*, 216:585-610, 1990.
130. Mulligan, *Science*, 260:926-932, 1993.
131. Myers, EP 0273085
132. Nicolas and Rubinstein, In: *Vectors: A survey of molecular cloning vectors and their uses*, Rodriguez and Denhardt, eds., Stoneham: Butterworth, pp. 494-513, 1988.
133. Nicolau and Sene, "Liposome-mediated DNA transfer in eukaryotic cells", *Biochim. Biophys. Acta*, 721:185-190, 1982.
134. Nicolau et al., "Liposomes as carriers for in vivo gene transfer and expression," *Methods Enzymol.*, 149:157-176, 1987.
135. Ohara et al., *Proc. Nat'l Acad. Sci. USA*, 86: 5673-5677, 1989.
136. PCT/US87/00880
137. PCT/US89/01025
138. Pease et al., "Light-generated oligonucleotide arrays for rapid DNA sequence analysis", *Proc. Natl. Acad. Sci. USA*, 91:5022-5026, 1994.
139. Pelletier and Sonenberg, *Nature*, 334:320-325, 1988.
140. Perales et al., "Gene transfer in vivo: Sustained expression and regulation of genes introduced into the liver by receptor-targeted uptake", *Proc. Natl. Acad. Sci.* 91:4086-4090, 1994.
141. Petersen et al., "Small-cell lung cancer is characterized by a high incidence of deletions on chromosomes 3p, 4q, 5q, 13q, and 17p", *Brit. J. Cancer* 75:79-86, 1997.
142. Pignon et al., *Hum. Mutat.*, 3: 126-132, 1994.
143. Potter et al., "Enhancer-dependent expression of human k immunoglobulin genes introduced into mouse pre-B lymphocytes by electroporation," *Proc. Nat. Acad. Sci. USA*, 81:7161-7165, 1984.
144. Racher et al., *Biotechnology Techniques*, 9:169-174, 1995.
145. Ragot et al., *Nature*, 361:647-650, 1993.
146. Ransom et al., "Correlation of cytogenetic analysis and loss of heterozygosity studies in human diffuse astrocytomas and mixed oligo-astrocytomas", *Genes Chromosom. Cancer* 5:357-374, 1992.
147. Rasheed et al., *Oncogene*, 11:2243-2246, 1995.
148. Reinhold-Hurek & Shub, "Self-splicing introns in tRNA genes of widely divergent bacteria," *Nature*, 357: 173-176, 1992.
149. Remington's Pharmaceutical Sciences, 15th ed., pp. 1035-1038 and 1570-1580.
150. Renan, "Cancer genes: Current status, future prospects and applications in radiotherapy/oncology," *Radiother. Oncol.*, 19:197-218, 1990.
151. Rich et al., *Hum. Gene Ther.*, 4:461-476, 1993.
152. Ridgeway, Mammalian Expression *Vectors, In: Vectors: A Survey of Molecular Cloning Vectors and Their Uses*, Rodriguez et al., eds., Stoneham: Butterworth, pp. 467-492, 1988.
153. Rippe et al., "DNA-mediated gene transfer into adult rat hepatocytes in primary culture," *Mol. Cell. Biol.*, 10:689-695, 1990.
154. Rosenfeld et al., In vivo transfer of the human cystic fibrosis transmembrane conductance regulator gene to the airway epithelium. *Cell*, 68:143-155, 1992.
155. Rosenfeld et al., *Science*, 252:431-434, 1991.
156. Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA*, 86:9079-9083, 1989.
157. Sambrook et al., In: *Molecular Cloning: A Laboratory Manual*, 2d Ed., Cold Spring Harbor Laboratory Press, Cold Spring Harbor, N.Y., 1989.
158. Sanchez, et al., "Microparticle immunoenzymatic assay for detection of prostate specific antigen: characterization of the technique and comparative analysis with a monoclonal immunoradiometric assay", *Mil Med.*, 160:(8)416-419, 1995.
159. Saras and Heldin CH "PDZ domains bind carboxyterminal sequences of target proteins", *Trends Biochem Sci.* 21 (12) 455-458, 1996.
160. Sarver et al., "Ribozymes as potential anti-HIV-1 therapeutic agents," *Science*, 247:1222-1225, 1990.

161. Scanlon et al., "Ribozyme-mediated cleavages of c-fos mRNA reduce gene expression of DNA synthesis enzymes and metallothionein," *Proc Natl Acad Sci USA*, 88:10591-10595, 1991.
162. Shoemaker et al., "Quantitative phenotypic analysis of yeast deletion mutants using a highly parallel molecular bar-coding strategy", *Nature Genetics* 14:450-456, 1996.
163. Sonoda et al., *Cancer Res.*, 55:2166-2168, 1995.
164. Spruck, et al., "p16 gene in uncultured tumours [letter] [see comments]"*Nature*, 370:(6486)183-184, (see also Comment in Nature 1994 Jul. 21; 370(6486):180 1994
165. Stewart and Young, Solid Phase Peptide Synthesis, 2d. ed., Pierce Chemical Co., 1984.
166. Stratford-Perricaudet and Perricaudet, Gene transfer into animals: the promise of adenovirus. In: *Human Gene Transfer*, O. Cohen-Haguenauer et al., eds., John Libbey Eurotext, France, pp. 51-61, 1991.
167. Stratford-Perricaudet et al., "Evaluation of the transfer and expression in mice of an enzyme-encoding gene using a human adenovirus vector", *Hum. Gene. Ther.*, 1:241-256, 1990.
168. Tam et al., *J. Am. Chem. Soc.*, 105:6442, 1983.
169. Temin, Retrovirus vectors for gene transfer: Efficient integration into and expression of exogenous DNA in vertebrate cell genome. In: *Gene Transfer*, Kucherlapati R, ed., New York, Plenum Press, pp. 149-188, 1986.
170. Tonics and Neel, "From form to function: signaling by protein tyrosine phosphatases" *Cell* 87:(3)365-368, (see also Comment in Cell 1996 Nov. 1; 87(3):361-4) 1996.
171. Top et al., "Immunization with live types 7 and 4 adenovirus vaccines. II. Antibody response and protective effect against acute respiratory disease due to adenovirus type 7," *J. Infect. Dis.*, 124:155-160, 1971.
172. Tur-Kaspa et al., "Use of electroporation to introduce biologically active foreign genes into primary rat hepatocytes", *Mol. Cell. Biol.*, 6:716-718, 1986.
173. U.S. Pat. No. 4,873,191, Wagner and Hoppe
174. U.S. Pat. No. 5,279,721
175. Varmus et al., *Cell*, 25:23-36, 1981.
176. Vogelstein, et al., "RAS gene mutations in childhood acute myeloid leukemia: a Pediatric Oncology Group study", *Genes Chromosomes Cancer*, 2:(2)159-162, 1990.
177. Wagner et al., *Proc. Natl. Acad. Sci.* 87(9):3410-3414, 1990.
178. Wagner et al., *Science*, 260:1510-1513, 1993.
179. Walker et al., *Proc. Nat'l Acad. Sci. USA*, 89:392-396 1992.
180. Wei et al., "Construction of a 600-kilobase cosmid clone contig and generation of a transcriptional map surrounding the lung cancer tumor suppressor gene (TSG) locus on human chromosome 3p21.3: progress toward the isolation of a lung cancer TSG", *Cancer Res.* 56:1487-1494, 1996.
181. Weinberg, "Positive and negative controls on cell growth", Biochemistry, 28:8263-8269, 1989.
182. WO 88/10351, Gingeras et al.
183. WO 89/06700, Miller et al.
184. WO 90/07641, filed Dec. 21, 1990.
185. Wong et al., "Appearance of b-lactamase activity in animal cells upon liposome mediated gene transfer", *Gene*, 10:87-94, 1980.
186. Wu and Wu, Adv. Drug Delivery Rev., 12:159-167, 1993.
187. Wu and Wu, "Evidence for targeted gene delivery to HepG2 hepatoma cells in vitro" *Biochemistry*, 27:887-892, 1988.
188. Wu and Wu, "Receptor-mediated in vitro gene transfections by a soluble DNA carrier system", *J. Biol. Chem.*, 262:4429-4432, 1987.
189. Wu et al., *Genomics*, 4:560, 1989.
190. Yang et al., In vivo and in vitro gene transfer to mammalian somatic cells by particle bombardment. *Proc. Natl. Acad. Sci. USA*, 87:9568-9572, 1990.
191. Zelenin et al., "High-velocity mechanical DNA transfer of the chloramphenicol acetyltransferase gene into rodent liver, kidney and mammary gland cells in organ explants and in vivo", *FEBS Lett.*, 280:94-96, 1991.
192. Abbondanzo et al., Breast Cancer Res. Treat., 16: 182(#151), 1990.
193. Alfthan et al., Cancer Res., 52:4628-4633, 1992.
194. Allred et al., Breast Cancer Res. Treat., 16: 182(#149), 1990.
195. Altschul et al., J. Mol. Biol., 215:403-410, 1990.
196. Ando et al., Int. J. Cancer, 40:12-17, 1987.
197. Antibodies: A Laboratory Manual, Cold Spring Harbor Laboratory, Cold Spring Harbor Press, Cold Spring Harbor, N.Y., 1988.
198. Ausubel, Brent, Kingston, Moore, Seidman, Smith, Struhl, eds., Current Protocols in Molecular Biology (Wiley, New York), 1994.
199. Barany and Merrifield, "The Peptides, Gross and Meienhofer, eds", Academic Press, New York, 1-284, 1979
200. Basombrio, Cancer Res., 30:2458-2462, 1970.
201. Bittner et al., Methods in Enzymol, 153:516-544, 1987.
202. Boel et al., Immunity, 2(2):167-75, 1995.
203. Boon et al., J. Exp. Med., 152:1184-1193, 1980.
204. Boring et al., Cancer Statistics, 1994.
205. Brown et al., Breast Cancer Res. Treat., 16: 192(#191), 1990.
206. Brunner et al., J. Immunol., 124:1627-1634, 1980.
207. Bystryn et al., Cancer Res., 45:5603-5607, 1985.
208. Campbell, In: Monoclonal Antibody Technology, Laboratory Techniques in Biochemistry and Molecular Biology, Vol. 13, Burden & Von Knippenberg (Eds.), Elseview, Amsterdam, pp. 71-74; 75-83, 1984.
209. Capaldi et al., Biochem. Biophys. Res. Comm., 76:425, 1977.
210. Carubia et al., Biochem. Biophys. Res. Commun., 120:500-504, 1984.
211. Chen et al., Proc. Am. Urol. Assn., 153: 267A, 1995.
212. Chien et al., Proc. Nat. Acad. Sci. USA, 88:9578-9582, 1991.
213. Chinault and Carbon, Gene, 5:111-126, 1979.
214. Chomczynski and Mackey, Anal. Biochem., 225:163-164, 1995.
215. Cohen, Science, 259:1691-1692, 1993
216. Cole et al., Endocrinology, 113:1176-1178, 1983.
217. Cox et al., S. Virol., 67(9):5664-5667, 1993.
218. Datta et al., J. Clin. Oncol., 12:475-482, 1994.
219. Denton et al., J Pathol, 167(2):187-91, 1992.
220. Diamond et al., J. Urol., 128:729-734, 1982.
221. Donahue et al., J. Biol. Chem., 269: 8604-8609, 1994
222. Dzau et al., Proc. Natl. Acad. Sci. USA, 93:11421-11425, 1996.
223. Elder et al., Cancer Res., 49:5091-5096, 1989.
224. EP 431,523
225. EPO 329,822
226. Fearon et al., Am J Clin Nutr, 47 (1):42-48, 1988.
227. Fidler and Hart, Science, 217:998-1001, 1982.
228. Fidler, et al., Res Immunol., 144:(4)284-7; discussion 294-8, 1983.

229. Fitzpatrick, T. B., In The American Cancer Society Cancer Handbook. Ch. 30, pp. 532-547, Doubleday & Co., Garden City, N.Y. (Arthur I. Holleb, M. D., ed.) 1986.
230. Forrest, A. P., J. Natl. Cancer Inst., 82:1525, 1990.
231. Frohman, In: PCR Protocols: A Guide To Methods And Applications, Academic Press, N.Y., 1990.
232. Furukawa et al., Proc. Natl. Acad. Sci. (USA), 90:1972-1976, 1993.
233. Fynan et al., Proc. Natl. Acad. Sci. USA, 90:11478-11482, 1993.
234. Gal et. al., Lab. Invest., 68(1):18, 1993.
235. Gaugler et al., J. Exper. Med., 179:921-930, 1994.
236. GB 2,202,328
237. Gefter et al., Somatic Cell Genet., 3: 231-236, 1977
238. Goding, In: Monoclonal Antibodies: Principles and Practice, 2d ed., Academic Press, Orlando, Fla., pp. 65-66, and 71-74, 1986.
239. Gomella et al., J. Urolology, 158:326-337, 1997.
240. Gross, Cancer Res., 3:326-333, 1943.
241. Hess et al., J. Adv. Enzyme Reg., 7:149, 1968.
242. Hewitt et al., Br J Cancer, 33 (3) p 241-59, 1976.
243. Hewitt et al., Br Med J, 2 (6033):477, 1976.
244. Hitzeman et al., J. Biol. Chem., 255:2073, 1980.
245. Holland et al., Biochemistry, 17:4900, 1978
246. Hollingsworth et al., Int J Cancer, 57(2):198-203, 1994.
247. Hoon et al., Int J Cancer, 69(5):369-74, 1996.
248. Hoon et al., J. Immunol., 154:730-737, 1995.
249. Hoon et al., J. Urol., 150(6):2013-2018, 1993.
250. Hoon et al., Int. J. Cancer, 43:857-862, 1989.
251. Innis et al., PCR Protocols, Academic Press, Inc., San Diego Calif., 1990.
252. Inouye et al., Nucleic Acids Res., 13: 3101-3109, 1985.
253. Irie, In: M. Torisu and T. Yoshida (eds), Basic mechanisms and clinical treatment of tumor metastasis, pp. 371-384, Academic Press, Tokyo, 1985.
254. Johnson et al., Peptide Turn Mimetics" IN: Biotechnology And Pharmacy, Pezzuto et al., eds., Chapman and Hall, New York, 1993.
255. Jones, Genetics, 85: 12, 1977.
256. Kingsman et al., Gene, 7: 141, 1979.
257. Klein et al., Cancer Res., 20:1561-1572, 1960.
258. Kohler and Milstein, Eur. J. Immunol. 6:511-519, 1976.
259. Kohler and Milstein, Nature, 256:495-497, 1975
260. Kripke, J. Natl. Canc. Inst., 53:333-1336, 1974.
261. Kwoh et al., Proc. Nat. Acad. Sci. USA, 86: 1173, 1989.
262. Kwon, B. S, J. Invest. Dermatol., 100(2 Suppl):134S-140S, 1993.
263. Kyte and Doolittle, J. Mol. Biol., 157:105-132, 1982.
264. Lehmann et al., Proc. Nat'l Acad. Sci. USA, 86:9891-9895, 1989.
265. Lehmann, et al., Cancer Res., 47:841-845, 1987.
266. Levy et al., Adv. Cancer Res., 24:1-59, 1977.
267. Liang and Pardee, Science, 257: 967-971, 1992.
268. Liang et al., Cancer Res., 52:6966-6968, 1992.
269. Lin and Guidotti, J. Biol. Chem., 264:14408-14414, 1989.
270. Lowy et al., Cell, 22: 17, 1980.
271. Madersbacher et al., Cancer Res., 54:5096-5100, 1994.
272. Marcillac et al., Cancer Res., 52:3901-3907, 1992.
273. Maryanski et al., Eur. J. Immunol., 124:1627-1634, 1980.
274. Maryanski et al., Eur. J. Immunol., 12:406-412, 1982.
275. McManus et al., Cancer Res., 36:3476-3481, 1976.
276. Melcher and Johnson, Mol. Cell. Biol., 15:2839-2848, 1995.
277. Merrifield, Science, 232: 341-347, 1986.
278. Mok et al., Gynecol. Oncol., 52: 247-252, 1994.
279. Morton et al., Cancer, 71:3737-3743, 1993.
280. Mosmann, J. Immunol. Methods, 65:55-63, 1983.
281. Mulligan, Science, 260:926-932, 1993.
282. Nagata et al., J. Biol. Chem., 267:12082-12089, 1992.
283. Nakamura et al., In: Handbook of Experimental Immunology (4th Ed.), Weir, E., Herzenberg, L. A., Blackwell, C., Herzenberg, L. (eds). Vol. 1, Chapter 27, Blackwell Scientific Publ., Oxford, 1987.
284. Natali et al., Cancer, 59:55-63, 1987.
285. Nordlund et al., J. Invest. Dermatol, 92:53 S-60S, 1989.
286. Nowell, P. C. Genetic instability in cancer cells: relationship to tumor cell heterogeneity. TUMOR CELL HETEROGENEITY, Owens, A. H., Coffey, D. S., Baylin, S. B. (eds.). New York, Academic Press (1982) pp. 351-365.
287. O'Hare et al., Proc. Nat'l Acad. Sci. USA, 78: 1527, 1981.
288. Ohara et al., Proc. Nat'l Acad. Sci. USA, 86: 5673-5677, 1989.
289. Palladino et al., Canc. Res., 47:5074-5079, 1987.
290. PCT/US87/00880
291. PCT/US89/01025
292. Pinkel, et al., Proc Natl Acad Sci USA, 83(9):2934-8, 1986.
293. Prehn, et al., J. Natl. Canc. Inst., 18:769-778, 1957.
294. Remington's Pharmaceutical Sciences, 15th ed., pp. 1035-1038 and 1570-1580; 624-652.
295. Robbins et al., Cancer Res, 54(12):3124-6, 1994.
296. Robzyk and Kassir, "A simple and highly efficient procedure for rescuing autonomous plasmids from yeast," Nucl. Acids Res., 20:3790, 1992.
297. Rubinstein et al., J. Natl. Cancer Inst., 82:1113-1120, 1990.
298. Sager et al., FASEB J., 7: 964-970, 1993.
299. Sambrook et al., Molecular Cloning, 2nd ed., Cold Spring Harbor Laboratory Press, CSH, 1.38-1.39, 1989.
300. Santerre et al., Gene, 30:147, 1984.
301. Sarantou et al., Cancer Res, 57(7):1371-6, 1997.
302. See Hewitt, et al., Brit. J. Cancer, 33:241-259, 1976.
303. Serrano et al., Nature, 366:704-707, 1993,
304. Serrano et al., Science, 267:249-252, 1995.
305. Smith and Johnson, "Single-step purification of polypeptides expressed in Escherichia Coli as fusions with glutathione S-transferase," Gene, 67:31-40, 1988.
306. Stewart and Young, Solid Phase Peptide Synthesis, 2d. ed., Pierce Chemical Co., 1984.
307. Stinchcomb et al., Nature, 282: 39, 1979.
308. Sun and Cohen, Gene, 137:127-132, 1993.
309. Szybalska et al., Proc. Nat'l Acad. Sci. USA, 48: 2026, 1962.
310. Talmadge et al., Nature, 307:37-40, 1984.
311. Tam et al., 3. Am. Chem. Soc., 105:6442, 1983.
312. Tang et al., Nature, 356:152-154, 1992.
313. Traversari et al., Immunogenetics, 35(3):145-52, 1992.
314. Traversari et al, J Exp Med., 176(5):1453-7, 1992.
315. Tschemper et al., Gene, 10: 157, 1980.
316. Tsuchida et al., J. Natl. Cancer Inst., 78:45-54, 1987a.
317. Tsuchida et al., J. Natl. Cancer Inst., 78:55-60, 1987b.
318. Ulmer et al., Science, 259:1745-1749, 1993.
319. Van den Eynde, et al., Biochem Soc Trans, 23(3):681-6, 1995.
320. Van den Eynde et al, J Exp Med, 182(3):689-98, 1995.
321. Van Der Bruggen, Traversari, Chomez, Lurquin, De Plaen, Van Den Eynde, Knuth, Boon, "A gene encoding an antigen recognized by cytolytic T lymphocytes on a human melanoma," Science, 254:1643-1647, 1991.

322. Van Pel et al., J. Exp. Med., 157:1992-2001, 1983.
323. Vijayasardahi et al., J. Experimental Medicine, 171(4): 1375-1380, 1990.
324. Visualization of Nucleic Acids" Gerad Morell Ed., CRC publ., 1995.
325. Wagner et al., Science, 260:1510-1513, 1993.
326. Walker et al., Proc. Nat'l Acad. Sci. USA, 89:392-396 1992.
327. Wang et al., In: Animal Cell Technology: Basic & Applied Aspects, S. Kaminogawa et al., (Cds), vol. 5, pp 463-469, Kluwer Academic Publishers, Netherlands, 1993.
328. Watson et al., Cancer Res., 54: 4598-4602, 1994.
329. Weitzel and Patel, GATA, 11(5-6) 165-170, 1994.
330. Weitzel et al., Genomics, 14:309-319, 1992.
331. Welsh et al., Nucleic Acids Res., 20: 4965-4970, 1992.
332. Whitton et al., J. Virol., 67:(1)348-352, 1993.
333. Wigler et al., Cell, 11: 223, 1977.
334. Wigler et al., Proc. Nat'l Acad. Sci. USA, 77: 3567, 1980.
335. Wong et al., Int. J. Oncol., 3: 13-17, 1993.
336. Wu et al., Genomics, 4:560, 1989
337. Yamaguchi et al., Br. J. Cancer, 60:382-384, 1989.
338. Yoshimura et al., Cancer, 73:2745-2752, 1994.
339. Burbee et al., J. Natl. Cancer Inst., 93: 691-699, 2001.340. Gao et al., J. Biol. Chem., 275: 12237-12242, 2000.
341. Wistuba 1. Bebrens C, Vinnani A, Mele 0, Milchgrub 5, Girard L. et al. High resolution chromosome 3p allelotyping of human lung cancer and preneoplastic/preinvasive bronchial epithelium reveals multiple, discontinuous sites of 3p allele loss and three regions of frequent breakpoints. Cancer Res 2000; 60:1949-60.
342. Sekido Y, Fong K M. Minna J D. Progress in understanding the molecular pathogenesis of human lung cancer. Biochim Biophys Acts 1998; 1378:F21-59.
343. Wistuba 11, Lam 5, Behrens C, Virmani A K, Fong K M. LeRiche 3, et al. Molecular damage in the bronchial epithelium of current and former smokers. J Nati Cancer Inst 1997; 89:1366-73.
344. Wistuba 11, Behrens C, Milchgrub 5, Bryant D, Hung J, Minna iD. et al. Sequential molecular abnormalities are involved in the multistage development of squamous cell lung carcinoma. Oncogene 1999; 18:643-50.
345. Kok K, Naylor S L, Buys C H. Deletions of the short arm of chromosome 3 in solid tumors and the search for suppressor genes. Adv Cancer Res 1997; 71:27-92.
346. Lerman M 1, Minna I D. The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium. Cancer Res 2000; 60:61 16-33.
347. Sekido Y, Ahmadian M, Wistuba I 1, Latif F, Bader 5, Wei M H, et al. Cloning of a breast cancer homozygous deletion junction narrows the region of search for a 3p21.3 tumor suppressorgene. Oncogene 1998; 16:3151-7.
348. Baylin S B, Herman J O, Graff J R. Vertino P M, Issa J P. Alterations in DNA methylation: a fundamental aspect of neoplasia. Adv Cancer Res 1998; 72:141-96.
349. Phelps R M, Johnson B E, Ibde D C, Oazdar A F, Carbone D P, McClintock P R, et al. NCI-Navy Medical Oncology Branch cell line database. J Cell Biochem Suppi 1996; 24:32-91.
350. Wistuba I I. Bryant D, Behrens C, Milchgrub S, Virmani A K, Ashfaq R, et al. Comparison of features of human lung cancer cell lines and their corresponding tumors. Chin Cancer Res 1999; 5:991-1000.
351. Gazdar A F, Kurvari V, Virmani A, Gollal~on L, Sakaguchi M, Westerfield M, et al. Characterization of paired tumor and non-tumor cell lines established from patients with breast cancer. Int 3 Cancer 1998; 78:766-74.
352. Herman J O, Graff J R, Myohanen 5, Nelkin B D, Baylin S B. Methylation specific PCR: a novel PCR assay for methylation status of CpO islands. Proc Natl Acad Sci USA 1996; 93:9821-6.
353. Zochbauer-Muller 5, Fong K M, Virmani A K, Geradts 3, Gazdar A F, Minna 3D. Aberrant promoter methylation of multiple genes in non-small cell lung cancers. Cancer Res 2001; 61:249-55.
354. Burbee, D., Forgacs, E., Zöchbauer-Müller, S., Shivakuma, L., Fong, K., Gao, B., Randle, D., Virmani, A., Bader, S., Sekido, Y., Latif, F., Milchgrub, S., Gazdar, A., Lerman, M., Zabarovsky, E., White, M. & Minna, J. (2001). *J Natl Cancer Inst*, (In Press).
355. Clark, S. J., Harrison, J., Paul, C. L. & Frommer, M. (1994). *Nucleic Acids Res*, 22, 2990-7.
356. Cook, W. D. & McCaw, B. J. (2000). *Oncogene*, 19, 3434-8.
357. Daly, M. C., Xiang, R. H., Buchhagen, D., Hensel, C. H., Garcia, D. K., Killary, A. M., Minna, J. D: & Naylor, S. L. (1993). Oncogene, 8, 1721-9.
358. Dammann, R., Li, C., Yoon, J. H., Chin, P. L., Bates, S. & Pfeifer, G. P. (2000). *Nat Genet*, 25, 315-9.
359. Di Cristofano, A., Pesce, B., Cordon-Cardo, C. & Pandolfi, P. P. (1998). *Nat Genet*, 19, 348-55.
360. Forgacs, E., Biesterveld, E. J., Sekido, Y., Fong, K., Muneer, S., Wistuba, I I, Milchgrub, S., Brezinschek, R., Virmani, A., Gazdar, A. F. & Minna, J. D. (1998). *Oncogene*, 17, 1557-65.
361. Hibi, K., Takahashi, T., Yamakawa, K., Ueda, R., Sekido, Y., Ariyoshi, Y., Suyaxna, M., Takagi, H., Nakamura, Y. & Takahashi, T. (1992). *Oncogene*, 7, 445-449.
362. Killary, A. M., Wolf, M. E., Giambemardi, T. A. & Naylor, S. L. (1992). *Proc Natl Acad Sci USA*, 89, 10877-81.
363. Kok, K., Naylor, S. L. & Buys, C. H. (1997). *Adv Cancer Res*, 71, 27-92.
364. Kok, K., Osing a, J., Carritt, B., Davis, M., van der Hout, A., van der Veen, A., Landsvater, R., de Leij, L., Berendsen, H., Postmus, P., Poppema, S. & Buys, C. (1987). *Nature (London)*, 330, 578-581.
365. Kok, K., van den Berg, A., Veldhuis, P., van der Veen, A., Franke, M., Schoenmakers, E., Hulsbeek, M., van der Hout, A., de Leij, L., van de Ven, W. & Buys, C. (1994). *Cancer Res*, 54, 4183-4187.
366. Lerman, M. & Minna, 3. (2000). *Cancer Res*, 60, 6116-6133.
367. Naylor, S. L., Johnson, B. E., Minna, J. D. & Sakaguchi, A. Y. (1987). *Nature*, 329, 451-4.
368. Roche, J., Boldog, F., Robinson, M., Robinson, L., Varella-Garcia, M., Swanton, M., Waggoner, B., Fishel, R., Franklin, W., Gemmill, R. & Drabkin, H. (1996). *Oncogene*, 12, 1289-97.
369. Sekido, Y., Ahmadian, M., Wistuba, I I, Latif, F., Bader, S., Wei, M. H., Duh, F. M., Gazdar, A. F., Lerman, M. I. & Minna, J. D. (1998). *Oncogene*, 16, 3151-7.
370. Wei, M. H., Latif, F., Bader, S., Kashuba, V., Chen, J. Y., Duh, F. M., Sekido, Y., Lee, C. C., Geil, L., Kuzmin, I., Zabarovsky, E., Klein, G., Zbar, B., Minna, J. D. & Lerman, M. I. (1996). *Cancer Res*, 56, 1487-92.

371. Whang-Peng, J., Bunn, P. J., Kao, S. C., Lee, E. C., Carney, D. N., Gazdar, A. & Minna, J. D. (1982). *Cancer Genet Cytogenet,* 6, 119-134.
372. Wistuba, I I, Behrens, C., Virmani, A. K., Mele, G., Milchgrub, S., Girard, L., Fondon, J. W., 3rd, Garner, H. R., McKay, B., Latif, F., Lerman, M. I., Lam, S., Gazdar, A. F. & Minna, J. D. (2000). *Cancer Res,* 60, 1949-60.
373. Xu, X., Brodie, S. G., Yang, X., Im, Y. H., Parks, W. T., Chen, L., Zhou, Y. X., Weinstein, M., Kim, S. J. & Deng, C. X. (2000). *Oncogene,* 19, 1868-74.
374. Zöchbauer-Müller, S., Fong, K., Virmani, A., Geradts, J., Gazdar, A. & Minna, J. (2001). *Cancer Res,* 61, 249-255.

We claim:

1. A method of altering the phenotype of a lung tumor cell comprising contacting said cell with an expression cassette comprising:
   (a) an isolated polynucleotide encoding a human FUS1 polypeptide; and
   (b) a heterologous promoter active in said tumor cell, under conditions permitting the uptake of said polynucleotide by said tumor cell.

2. The method of claim 1, wherein the phenotype is selected from the group consisting of proliferation, migration, contact inhibition, soft agar growth, cell cycling, invasiveness, tumorigenesis, and metastatic potential.

3. The method of claim 1, wherein said promoter is a cytomegalovirus (CMV) promoter.

4. The method of claim 1, wherein said expression cassette is contained in a lipid preparation.

* * * * *

UNITED STATES PATENT AND TRADEMARK OFFICE
CERTIFICATE OF CORRECTION

PATENT NO. : 9,944,951 B2
APPLICATION NO. : 13/114921
DATED : April 17, 2018
INVENTOR(S) : Ji et al.

It is certified that error appears in the above-identified patent and that said Letters Patent is hereby corrected as shown below:

In the Specification

In Column 1, Lines 12-14, delete paragraph and insert --This invention was made with government support under grant number CA070907 awarded by the National Institutes of Health. The government has certain rights in the invention.-- therefor.

Signed and Sealed this
Twenty-fourth Day of July, 2018

Andrei Iancu
*Director of the United States Patent and Trademark Office*

SEQUENCE LISTING

<160> NUMBER OF SEQ ID NOS: 17

<210> SEQ ID NO 1
<211> LENGTH: 1746
<212> TYPE: DNA
<213> ORGANISM: Homo sapiens

<400> SEQUENCE: 1

```
gatccccaac cgtcccgcaa ctgtcctgtc ccagactttg gcaccgtcgg ggtccgtcgt      60
ccccgaatgt gacagcatcc ccaccccggc tgctgcccag gatccgccgg accccggcct     120
cgatatggga gacctggaac tgctgctgcc cggggaagct gaagtgctgg tgcgggtct     180
gcgcagcttc ccgctacgcg agatgggctc cgaagggtgg aaccagcagc atgagaacct     240
ggagaagctg aacatgcaag ccatcctcga tgccacagtc agccagggcg agcccattca     300
ggagctgctg gtcacccatg ggaaggtccc aacactggtg gaggagctga tcgcagtgga     360
gatgtggaag cagaaggtgt tccctgtgtt ctgcagggtg gaggacttca gccccagaa     420
caccttcccc atctacatgg tggtgcacca cgaggcctcc atcatcaacc tcttggagac     480
agtgttcttc cacaaggagg tgtgtgagtc agcagaagac actgtcttgg acttggtaga     540
ctattgccac cgcaaactga ccctgctggt ggcccagagt ggctgtggtg gcccccctga     600
gggggaggga tcccaggaca gcaacccat gcaggagctg cagaagcagg cagagctgat      660
ggaatttgag attgcactga aggccctctc agtactacgc tacatcacag actgtgtgga     720
cagcctctct ctcagcacct tgagccgtat gcttagcaca cacaacctgc cctgcctcct     780
ggtggaactg ctggagcata gtccctggag ccggcgggaa ggaggcaagc tgcagcagtt     840
cgagggcagc cgttggcata ctgtggcccc ctcagagcag caaaagctga gcaagttgga     900
cgggcaagtg tggatcgccc tgtacaacct gctgctaagc cctgaggctc aggcgcgcta     960
ctgcctcaca agttttgcca agggacggct actcaagctt cgggccttcc tcacagacac    1020
actgctggac cagctgccca acctggccca cttgcagagt ttcctggccc atctgaccct    1080
aactgaaacc cagcctccta agaaggacct ggtgttggaa cagatcccag aaatctggga    1140
gcggctggag cgagaaaaca gaggcaagtg gcaggcaatt gccaagcacc agctccagca    1200
tgtgttcagc ccctcagagc aggacctgtg gctgcaggcg cgaaggtggg ctgagaccta    1260
caggctggat gtgctagagg cagtggctcc agagcggccc cgctgtgctt actgcagtgc    1320
agaggcttct aagcgctgct cacgatgcca gaatgagtgg tattgctgca gggagtgcca    1380
agtcaagcac tgggaaaagc atggaaagac ttgtgtcctg gcagcccagg gtgacagagc    1440
caaatgaggg ctgcagttgc tgagggccga ccacccatgc caagggaatc cacccagaat    1500
gcacccctga acctcaagat cacggtccag cctctgccgg agcccagtc tccgcagtgg     1560
agagcagagc gggcggtaaa gctgctgacc gatctccctc ctcctcaccc caagtgaagg    1620
ctcgagactt cctgccccac ccagtgggta ggccaagtgt gttgcttcag caaaccggac    1680
caggagggcc agggccggat gtggggaccc tcttcctcta gcacagtaaa gctggcctcc    1740
agatcg                                                              1746
```

```
<210> SEQ ID NO 2
<211> LENGTH: 362
<212> TYPE: PRT
<213> ORGANISM: Homo sapiens

<400> SEQUENCE: 2

Met Gln His Pro His Pro Gly Cys Cys Pro Lys Pro Arg Pro Arg Tyr
1               5                   10                  15

Gly Arg Pro Gly Thr Ala Ala Arg Gly Ser Ser Ala Gly Ala Gly
            20                  25                  30

Ser Ala Gln Leu Pro Ala Thr Arg Arg Val Glu Pro Ala Ala Glu Pro
        35                  40                  45

Gly Glu Ala His Pro Arg Cys His Ser Gln Pro Gly Arg Ala His Ser
    50                  55                  60

Gly Ala Ala Gly His Pro Trp Glu Gly Pro Asn Thr Gly Gly Ala
65                  70                  75                  80

Asp Val Glu Ala Glu Gly Val Pro Cys Val Leu Gln Gly Ala Pro Glu
                85                  90                  95

His Leu Pro His Leu His Gly Gly Ala Pro Arg Gly Leu His His Gln
            100                 105                 110

Pro Leu Gly Asp Ser Val Leu Pro Gln Gly Val Ser Arg Arg His Cys
        115                 120                 125

Leu Gly Leu Gly Arg Leu Leu Pro Pro Ala Gly Gly Pro Glu Trp Leu
    130                 135                 140

Trp Trp Pro Pro Gly Gly Gly Ile Pro Gly Gln Gln Pro His Ala Gly
145                 150                 155                 160

Ala Ala Glu Ala Gly Ile Asp Cys Thr Glu Gly Pro Leu Ser Thr Thr
                165                 170                 175

Leu Cys Gly Gln Pro Leu Ser Gln His Leu Glu Pro Tyr Ala His Thr
            180                 185                 190

Gln Pro Ala Leu Pro Pro Gly Gly Thr Ala Gly Ala Ser Leu Glu Pro
        195                 200                 205

Ala Gly Arg Arg Gln Ala Ala Val Arg Gly Gln Cys Gly Pro Leu
    210                 215                 220

Arg Ala Ala Lys Ala Glu Gln Val Gly Arg Ala Ser Val Asp Arg Pro
225                 230                 235                 240

Val Gln Pro Ala Ala Lys Pro Gly Leu Pro His Lys Phe Cys Gln Gly
                245                 250                 255

Thr Ala Thr Gln Ala His Arg His Thr Ala Gly Pro Ala Ala Gln Pro
            260                 265                 270

Gly Pro Leu Ala Glu Phe Pro Gly Pro Ser Asp Pro Asn Asn Pro Ala
        275                 280                 285

Ser Glu Gly Pro Gly Val Gly Thr Asp Pro Arg Asn Leu Gly Ala Ala
    290                 295                 300

Gly Arg Gln Val Ala Gly Asn Cys Gln Ala Pro Ala Pro Ala Cys Val
305                 310                 315                 320

Gln Pro Leu Arg Ala Gly Pro Val Ala Ala Gly Ala Lys Val Asp Leu
                325                 330                 335

Gln Ala Gly Cys Ala Arg Gly Ser Gly Ser Arg Ala Ala Leu Gln Cys
            340                 345                 350

Arg Gly Phe Ala Leu Leu Thr Met Pro Glu
        355                 360
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ctgcagccaa gaggactcgg                                          20

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
tgcaagttca cctgccac                                            18

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5 catgacaaact ttggtatcgt g                                       21

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
gtgtcgctgt tgaagtcaga                                          20

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
gggttttgcg agagcgcg                                            18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
gctaacaaac gcgaaccg                                            18

<210> SEQ ID NO 9
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 9 ggtttgtga gagtgtgttt ag                                         22

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cactaacaaa cacaaaccaa ac                                        22

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
gttatggtag tgcggactg                                            19

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
ggtggaacca ttgcccttac                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
gacctgtgac atttgccgtg                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
caacagatcc catctgggtc                                           20

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
cctgagctga ccccttaca                                            19
```

-continued

```
<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
tctgtctgcc acctcccag                                                    19

<210> SEQ ID NO 17
<211> LENGTH: 38
<212> TYPE: DNA
<213> ORGANISM: Artificial Sequence
<220> FEATURE:
<223> OTHER INFORMATION: Synthetic primer

<400> SEQUENCE: 17
aggcgagtgc ataagaatct gattcctcag gtacgtga                               38
```